United States Patent
Salamini et al.

(10) Patent No.: US 9,990,859 B2
(45) Date of Patent: *Jun. 5, 2018

(54) INTRAORAL TACTILE BIOFEEDBACK METHODS, DEVICES AND SYSTEMS FOR SPEECH AND LANGUAGE TRAINING

(71) Applicant: ARTICULATE TECHNOLOGIES, INC., San Francisco, CA (US)

(72) Inventors: Alexey Salamini, San Francisco, CA (US); Adrienne E. Penake, San Mateo, CA (US); David A. Penake, San Mateo, CA (US); Gordy T. Rogers, Brooklyn, NY (US)

(73) Assignee: Speech Buddies, Inc., San Francisco, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/475,895

(22) Filed: Mar. 31, 2017

(65) Prior Publication Data

US 2017/0206805 A1 Jul. 20, 2017

Related U.S. Application Data

(63) Continuation-in-part of application No. 14/343,380, filed as application No. PCT/US2012/054114 on Sep.
(Continued)

(51) Int. Cl.
*G09B 19/04* (2006.01)
*A61B 5/00* (2006.01)
(Continued)

(52) U.S. Cl.
CPC .......... *G09B 19/04* (2013.01); *A61B 5/1107* (2013.01); *A61B 5/4803* (2013.01); *A61B 5/486* (2013.01);
(Continued)

(58) Field of Classification Search
CPC .......... A61F 5/58; G09B 19/04; G09B 19/06; A61B 5/228; A61B 5/682; A61B 5/486;
(Continued)

(56) References Cited

U.S. PATENT DOCUMENTS

| 779,360 A | 1/1905 | Grumman |
|---|---|---|
| 1,327,407 A | 1/1920 | Rogers |

(Continued)

FOREIGN PATENT DOCUMENTS

| DE | 202 06 571 U1 | 9/2002 |
|---|---|---|
| JP | 2004-093723 A | 3/2004 |

(Continued)

OTHER PUBLICATIONS

Kaczmarek et al., "Electrotactile and Vibrotactile Displays for Sensory Substitution Systems," IEEE Transactions on Biomedical Engineering, 38(1):1-16 (Jan. 1991).
(Continued)

*Primary Examiner* — Jack Yip
(74) *Attorney, Agent, or Firm* — Winston & Strawn LLP

(57) ABSTRACT

An intraoral method, biofeedback system and kit are provided for supplying intraoral feedback representative of a speaker's pronunciation during sound production, which feedback may be used for training and enhancing a speaker's pronunciation accuracy.

20 Claims, 36 Drawing Sheets

Related U.S. Application Data 7, 2012, application No. 15/475,895, which is a continuation-in-part of application No. 15/046,415, filed on Feb. 17, 2016, which is a continuation of application No. 14/274,223, filed on May 9, 2014, now abandoned, which is a continuation of application No. 12/357,239, filed on Jan. 21, 2009, now Pat. No. 8,740,622.

(60) Provisional application No. 61/011,364, filed on Jan. 17, 2008, provisional application No. 61/533,087, filed on Sep. 9, 2011.

(51) Int. Cl.
*A61F 5/58* (2006.01)
*A61B 5/11* (2006.01)

(52) U.S. Cl.
CPC ............ *A61B 5/4848* (2013.01); *A61B 5/682* (2013.01); *A61B 5/6835* (2013.01); *A61B 5/7455* (2013.01); *A61F 5/58* (2013.01); *A61B 5/1124* (2013.01); *A61B 5/743* (2013.01); *A61B 5/744* (2013.01); *A61B 2503/12* (2013.01); *A61B 2505/09* (2013.01); *A61B 2562/0247* (2013.01); *A61B 2562/04* (2013.01)

(58) Field of Classification Search
CPC .......... A61B 23/032; A61B 2071/0625; A61B 5/6835; A61B 5/743; A61B 5/744; A61B 5/1107; A61B 5/4848; A61B 2503/12; A61B 2562/04; A61B 5/4803; A61B 5/7455; A61B 2505/09; A61B 2562/0247; A61B 5/1124
USPC ................................................. 434/185, 157
See application file for complete search history.

(56) References Cited

U.S. PATENT DOCUMENTS

| | | | |
|---|---|---|---|
| 2,098,867 | A | 11/1937 | Glisson |
| D160,490 | S | 10/1950 | Gee |
| 2,549,398 | A | 4/1951 | Stelz |
| 2,818,065 | A | 12/1957 | Freed |
| 3,014,286 | A | 12/1961 | Hricak |
| 3,401,685 | A | 9/1968 | Staub |
| 3,556,093 | A | 1/1971 | Quick |
| 3,867,770 | A | 2/1975 | Davis |
| 3,983,865 | A | 10/1976 | Shepard |
| 4,112,596 | A | 9/1978 | Fletcher |
| 4,287,895 | A | 9/1981 | Hori |
| 4,310,002 | A | 1/1982 | Takinishi et al. |
| 4,334,542 | A | 6/1982 | Takinishi et al. |
| 4,629,424 | A | 12/1986 | Lauks et al. |
| 4,697,601 | A | 10/1987 | Durkee et al. |
| 4,718,662 | A | 1/1988 | North |
| 4,723,910 | A | 2/1988 | Keller |
| 5,213,553 | A | 5/1993 | Light |
| 5,257,930 | A | 11/1993 | Blakeley |
| 5,401,234 | A | 3/1995 | Libin |
| 5,452,727 | A | 9/1995 | Tura et al. |
| 5,507,648 | A | 4/1996 | Knopf |
| 5,609,161 | A | 3/1997 | Tura et al. |
| 5,689,246 | A | 11/1997 | Dordick et al. |
| 5,735,772 | A | 4/1998 | Schiavoni |
| 5,794,203 | A | 8/1998 | Kehoe |
| 5,954,673 | A | 9/1999 | Stachlin et al. |
| 6,190,335 | B1 | 2/2001 | Howard et al. |
| 6,430,450 | B1 | 8/2002 | Bach-y-Rita et al. |
| 6,511,441 | B1 | 1/2003 | Wakumoto et al. |
| 6,598,006 | B1 | 7/2003 | Honda et al. |
| 6,632,095 | B2 | 10/2003 | Ryan |
| 6,702,765 | B2 | 3/2004 | Robbins et al. |
| 6,971,993 | B2 | 12/2005 | Fletcher |
| 6,974,424 | B2 | 12/2005 | Fletcher |
| 7,083,548 | B1 | 8/2006 | Moore et al. |
| 7,214,064 | B1 | 5/2007 | Hall |
| 7,238,145 | B2 | 7/2007 | Robbins et al. |
| 7,438,667 | B2 | 10/2008 | Robbins et al. |
| 7,676,372 | B1 | 3/2010 | Oba |
| 7,935,065 | B2 | 5/2011 | Martin et al. |
| 7,999,857 | B2 | 8/2011 | Bunn et al. |
| 2002/0087103 | A1 | 7/2002 | Fletcher |
| 2002/0087322 | A1 | 7/2002 | Fletcher |
| 2003/0078521 | A1 | 4/2003 | Robbins et al. |
| 2003/0121521 | A1 | 7/2003 | Hipolito et al. |
| 2004/0038188 | A1 | 2/2004 | Lee |
| 2006/0028556 | A1 | 2/2006 | Bunn et al. |
| 2006/0282010 | A1 | 12/2006 | Martin et al. |
| 2007/0037665 | A1 | 2/2007 | Robbins et al. |
| 2007/0168187 | A1 | 7/2007 | Fletcher et al. |
| 2007/0225122 | A1 | 9/2007 | Robbins et al. |
| 2008/0183107 | A1 | 7/2008 | Miller et al. |
| 2008/0228239 | A1 | 9/2008 | Tyler et al. |
| 2008/0271590 | A1 | 11/2008 | Lemmons |
| 2008/0286731 | A1 | 11/2008 | Rolstone |
| 2009/0138270 | A1 | 5/2009 | Fletcher et al. |
| 2009/0155751 | A1 | 6/2009 | Paul |
| 2009/0186324 | A1 | 7/2009 | Penake et al. |
| 2009/0286199 | A1 | 11/2009 | Creasman et al. |
| 2009/0309747 | A1 | 12/2009 | Ghovanloo et al. |
| 2009/0326604 | A1 | 12/2009 | Tyler et al. |
| 2010/0117837 | A1 | 5/2010 | Stirling et al. |
| 2011/0202111 | A1 | 8/2011 | Dillon et al. |
| 2011/0224287 | A1 | 9/2011 | Rully et al. |
| 2012/0151344 | A1 | 6/2012 | Humphrey |
| 2015/0045698 | A1* | 2/2015 | Gribb .................. A61B 5/4205 600/587 |

FOREIGN PATENT DOCUMENTS

| | | |
|---|---|---|
| JP | 2004-272188 A | 9/2004 |
| KR | 10-2006-0002632 A | 1/2006 |

OTHER PUBLICATIONS

Tiede et al., "A New Approach to Pressure-Sensitive Palatography Using a Capacitive Sensing Device," Proceedings of the 15th International Congress of Phonetic Sciences, Barcelona, Spain (Aug. 3-9, 2003). http://www.haskins.yale.edu/Reprints/HL1312.pdf.
International Search Report and Written Opinion, Appl. No. PCT/US2012/054114, dated Nov. 12, 2012.
International Search Report and Written Opinion, Appl. No. PCT/U52009/031584, dated Sep. 7, 2009.
U.S. Appl. No. 14/343,380, Non-Final Rejection, dated Nov. 27, 2015.
U.S. Appl. No. 14/343,380, Final Rejection, dated May 17, 2016.
U.S. Appl. No. 14/343,380, Advisory Action, dated Jun. 21, 2016.
U.S. Appl. No. 14/343,380, Non-Final Rejection, dated Sep. 8, 2016.
U.S. Appl. No. 14/343,380, Final Rejection, dated Jan. 3, 2017.
U.S. Appl. No. 15/046,415, Non-Final Rejection, dated Aug. 11, 2016.
U.S. Appl. No. 15/046,415, Final Rejection, dated Feb. 22, 2017.
U.S. Appl. No. 14/274,223, Non-Final Rejection, dated May 6, 2015.
U.S. Appl. No. 14/274,223, Final Rejection, dated Nov. 17, 2015.
U.S. Appl. No. 14/274,223, Advisory Action, dated Feb. 8, 2016.
U.S. Appl. No. 12/357,239, Non-Final Rejection, dated Jun. 18, 2012.
U.S. Appl. No. 12/357,239, Final Rejection, dated Nov. 23, 2012.
U.S. Appl. No. 12/357,239, Non-Final Rejection, dated Jun. 27, 2013.
U.S. Appl. No. 12/357,239, Notice of Allowance, dated Feb. 3, 2014.

* cited by examiner

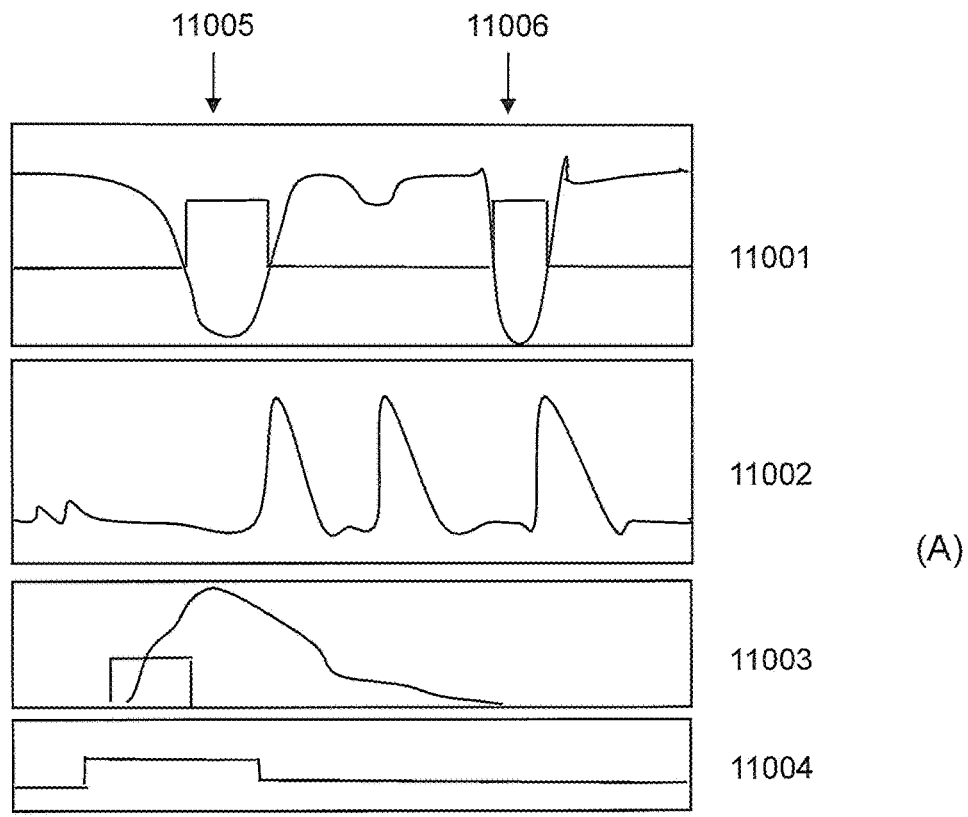
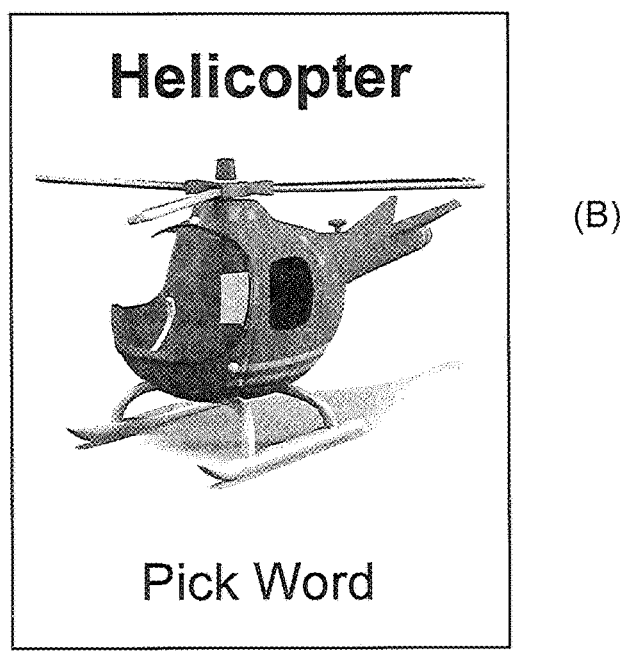
FIG. 36

INTRAORAL TACTILE BIOFEEDBACK METHODS, DEVICES AND SYSTEMS FOR SPEECH AND LANGUAGE TRAINING

CROSS-REFERENCE TO RELATED APPLICATIONS

This application is a continuation-in-part of co-pending U.S. application Ser. No. 14/343,380 filed Mar. 6, 2014, which is the U.S. national phase of International Application No. PCT/US2012/054114 filed Sep. 7, 2012, which in turn claims the benefit of U.S. Application No. 61/533,087 filed on Sep. 9, 2011, the entire disclosure of each of which is hereby incorporated by reference.

This application is also a continuation-in-part of co-pending U.S. application Ser. No. 15/046,415 filed Feb. 17, 2016, which is a continuation of U.S. application Ser. No. 14/274,223 filed May 9, 2014, abandoned, which is a continuation of U.S. application Ser. No. 12/357,239, filed Jan. 21, 2009, now U.S. Pat. No. 8,740,622 B2, which claims the benefit of U.S. Application No. 61/011,364, filed Jan. 17, 2008, the entire disclosures of which are hereby incorporated by reference.

FIELD OF TECHNOLOGY

The present invention relates to the fields of articulation, speech therapy and language learning. More particularly, the present invention relates to interactive methods, devices and systems for providing intraoral feedback for training and enhancing a speaker's pronunciation accuracy by non-invasive interaction with a subject's oral cavity.

BACKGROUND

In order to produce speech sounds that comprise the acoustic signal of human language, a complex set of coordinated muscle movements must be realized. Each speech sound requires that a unique series of movements be performed. For example, the tongue must change shape and/or make contact with various landmarks within the oral cavity, often in a precise sequence of movements with each movement corresponding to at least one ideal pronunciation of a particular speech sound.

Many people, particularly children, experience speech sound disorders in which the speaker may not be able to effect the particular series of movements necessary to produce a particular speech sound. For these individuals, the improper series of tongue movements may result in distorted speech sounds that affect the overall intelligibility of an individual's speech. Some speech sounds (called "phonemes") in a speaker's native language may not be produced, may not be produced correctly or may not be used correctly. Speech sound disorders are typically classified into articulation disorders ("phonetic disorders") and phonemic disorders ("phonological disorders"), although some speakers may suffer from a mixed disorder in which both articulation and phonological problems exist (see http://en.wikipedia.org/wiki/Speech_sound_disorder#Articulation_Disorders).

Errors produced by speakers with speech sound disorders may include omissions (certain sounds are not produced, or entire syllables or classes of sounds may be deleted), additions (extra sounds are added to the intended words), distortions (sounds are changed slightly so that the intended sound may be recognized but sound "wrong", e.g., as in a lisp) and substitutions (one or more sounds are substituted for another, e.g., "wabbit" for "rabbit"). The magnitude of such errors can vary among speakers, and some errors may demonstrate variable magnitude in errors among different sounds. Some speakers may involuntarily demonstrate more than one error during speaking.

Various attempts have been made to diagnose and treat speech sound disorders in a manner that addresses the varying magnitude of speech errors as well as the wide array of possible causes for such errors.

U.S. Pat. No. 4,112,596, for example, is directed to a pseudo palate used for diagnosis and treatment of speech impairments. The disclosed pseudo palate is formed of a thin material sheet shaped to the contour of the patient's palate. An array of electrodes is provided on the lingual surface of the sheet with the electrodes having predetermined spaces therebetween. Conductors attached to the electrodes are embedded in the sheet and grouped together to exit from a posterior portion of the palate for exit from the patient's mouth. With the pseudo palate in place, a small voltage is applied to the patient's body, for example, by securing an electrode to the patient's wrist. The conductors communicate with processing and display equipment that provides visual and/or aural signals corresponding to a position of the tongue when the patient makes, or attempts to make, designated speech sounds.

U.S. Pat. No. 6,974,424 is directed to palatometer and nasometer apparatus. The palatometer includes a flexible printed circuit with electrodes that fits in a patient's mouth. The position and movement of the tongue and lips are indicated on processing and display equipment in communication with the electrodes. The nasometer includes a set of interchangeable sound separator plates to fit patients with different facial curvatures. Microphones are attached to each sound separator plate to measure sound emitted form the nose and mouth for determining the nasality of speech.

U.S. Pat. No. 6,971,993 is directed to a method for providing speech therapy that uses a model representation of a position of contact between a model tongue and mouth during speech. A device is used that includes a sensor plate having sensors for detection of contact with a user's tongue. Representations of contact between the tongue and palate during speech can be viewed and compared with model representations (for example, on a processing and display device having a split screen). The model representations, which may be mimicked for speech enhancement, may be generated by another speaker using a sensor plate or by computer generated representations that have been electronically stored.

U.S. Publication Nos. 2009/0138270 and 2007/0168187 are directed to speech analysis and visualization feedback integrated into speech therapy methods. In U.S. Publication No. 2007/0168187, an audio input of a computing system receives a speech signal that is visually compared with the ideal pronunciation of the speech signal to visualize relative accuracy. In U.S. Publication Nos. 2009/0138270, a sensor plate having a plurality of sensors is disposed against a learner's palate. A set of parameters representing a contact pattern between the learner's tongue and palate during an utterance is ascertained from a speech signal. For each parameter, a deviation is measure is calculated relative to a corresponding set of parameters from an ideal pronunciation of the utterance. An accuracy score is generated from the deviation measure.

U.S. Publication No. 2008/0228239 is directed to systems and methods for sensory substitution and/or enhancement for treatment of multiple conditions that involve the loss or impairment of sensory perception. Some systems may train subjects to correlate tactile information with environmental information to be perceived, thereby improving vestibular function. In one example, tactile stimulation (e.g., electrotactile stimulation of the tongue) is relied upon in applications where deep brain stimulation is used and contemplated for use.

These known methods and devices employ complex visual and verbal cues to indicate correct movement and placement of oral articulators. Speech sounds requiring proper tongue position, shape, and movement are difficult to teach because the required tongue position, shape, and movement take place behind the teeth and are therefore difficult to show to a patient. Consequently, it is difficult for patients to assimilate these types of complex motor patterns when taught with traditional visual and verbal cues. In particular, complex verbal cues used to teach proper tongue shape and movement may be difficult for younger patients to process.

Despite these known methods and devices, a need persisted for improved approaches for the recognition and treatment of different speech pathologies. Applicants addressed this need by providing methods and devices that employ intraoral tactile feedback to train proper tongue positioning corresponding to particular speech sounds (see Applicant's U.S. Pat. No. 8,740,622 B2, the entire disclosure of which is incorporated by reference herein). Applicant's disclosed methods and devices are intuitively used by speakers, therapists and family members (such as parents and other primary caregivers) for use in navigating the speaker's oral cavity and reinforcing proper tongue placement therewithin. Applicants' disclosed methods and devices also promote interchangeability and modularity for creation of multiple speech sounds, and portability for encouragement of use in a variety of environments, thereby leading the speaker to realize beneficial results within a shortened timeframe.

These and additional attributes are provided by methods, devices and systems disclosed herein that provide intraoral biofeedback, both independently and in cooperation with a software platform.

SUMMARY

The presently disclosed invention includes embodiments directed to methods, devices and systems for providing intraoral feedback for training and enhancing a speaker's pronunciation accuracy. In accordance with one aspect of the invention, a speech articulation disorder may be treated by providing tactile feedback to the patient to indicate proper position of the tongue for the production of a target "sound". The term "sound" as used herein includes the phonetic terms phoneme and allophone. "Sound" also refers generally to any sound, sound pattern, word, word pattern, sentence, utterance, lip movement (whether made with or without vocalization), breathing pattern and any complement, equivalent and combination thereof "Pronunciation" refers generally to the production of any sound as contemplated herein, including but not limited to the production of lip movements (whether with or without vocalization), the production of breaths and breathing patterns, the production of tongue clicks and any complement, equivalent and combination thereof.

An intraoral method for providing feedback representative of a speaker's pronunciation during sound production includes locating targets in the speaker's oral cavity to train at least one target sound through tactile feedback to the speaker. Target location is dependent upon the sound being trained. At least one sound training device is provided that includes a head having one or more nodes to provide tactile feedback to the speaker indicating a position of the speaker's tongue for accurate pronunciation of the at least one target sound, a handle for holding and positioning the one or more nodes in the speaker's oral cavity, and at least one sensor at or near at least one node of each device. The at least one sensor is positioned at or near each target in correspondence with proper lingual positions for the production of the target sounds. The sensors are provided at or near at least one node on each device so that insertion of the device in the speaker's oral cavity automatically places the sensors at or near the intended target. The sensor detects pronunciation accuracy of the target sound when the speaker's tongue contacts the intended target during sound production. The sound training device may be a network-connected device in communication with a computing device running a software application, such as a pronunciation evaluation application or a general diagnostic test.

An intraoral biofeedback system for training and enhancing a speaker's pronunciation accuracy includes at least one sound training device having a head with one or more nodes that provide tactile feedback to the speaker. Such feedback indicates an accurate position of the speaker's tongue for the correct pronunciation of at least one target sound. The sound training device also includes a handle for holding and positioning the one or more nodes in the speaker's oral cavity. The sensors are provided at or near at least one node on each device. Each sound training device is preferably configured with registration features for positioning thereof in a location in the speaker's oral cavity, so that the speaker's tongue freely navigates the oral cavity to correctly contact the one or more nodes for properly making the at least one target sound. Also, the insertion of the device in the speaker's oral cavity enables the registration features to automatically place the at least one sensor in correspondence with proper lingual positions for production of the at least one target sound. The sensor thereby detects pronunciation accuracy of the target sound when the speaker's tongue contacts the intended target during sound production.

The sound training device may be a network-connected device in operative communication with a computing device running at least one pronunciation evaluation application thereon. The system may further include a server in communication with the network-connected device. The server is configured to perform actions including accessing the system over a network via a network interface, and performing a method for providing feedback representative of a speaker's pronunciation. The server may also be configured to perform actions including at least one accessing a social networking system over the network; building and accessing a database of profiles of sensor outputs that can be generated for intended target sounds; and uploading at least one of speaker profile data and data corresponding to one or more diagnostic and practice exercises for storage on the database.

A kit for providing intraoral feedback representative of a speaker's pronunciation during sound production includes one or more heads for a sound training device. Each head has one or more nodes to provide tactile feedback to the speaker indicating an accurate position of the speaker's tongue for the correct pronunciation of at least one target sound. At least one sensor is provided at or near each one node such that insertion of a selected device in the speaker's oral cavity automatically places the sensors at or near an intended target corresponding to the target sound. The sensor detects pronunciation accuracy of the target sound when the speaker's tongue contacts the intended target during sound production.

The kit also includes one or more handles for the sound training device, with each handle enabling the speaker (or another user) to hold and position the nodes in the speaker's oral cavity. The heads are selectively interchangeable with the handles to perform a method of for providing feedback representative of a speaker's pronunciation.

The kit may further include one or more interactive software applications loadable onto a computing device. Instructions for use of the software applications may be provided that include instructions for accessing a platform that provide the speaker with an interface for collaboration with others over a social network. The kit may also include a mobile device having the software applications pre-loaded thereon.

Additional aspects of the presently disclosed methods, devices and systems will be made apparent from the following detailed description.

BRIEF DESCRIPTION OF THE DRAWINGS

The nature and various advantages of the present invention will become more apparent upon consideration of the following detailed description, taken in conjunction with the accompanying drawings, in which like reference characters refer to like parts throughout, and in which:

FIG. 36 shows how data from both a microphone and an optical sensor are used to determine correct and incorrect pronunciations on a graphical user interface for a smart phone, wherein A is a graph of the sound spoken by the person and B is a view of a sample card that the person is asked to read.

DETAILED DESCRIPTION OF THE INVENTION

Figure 1:
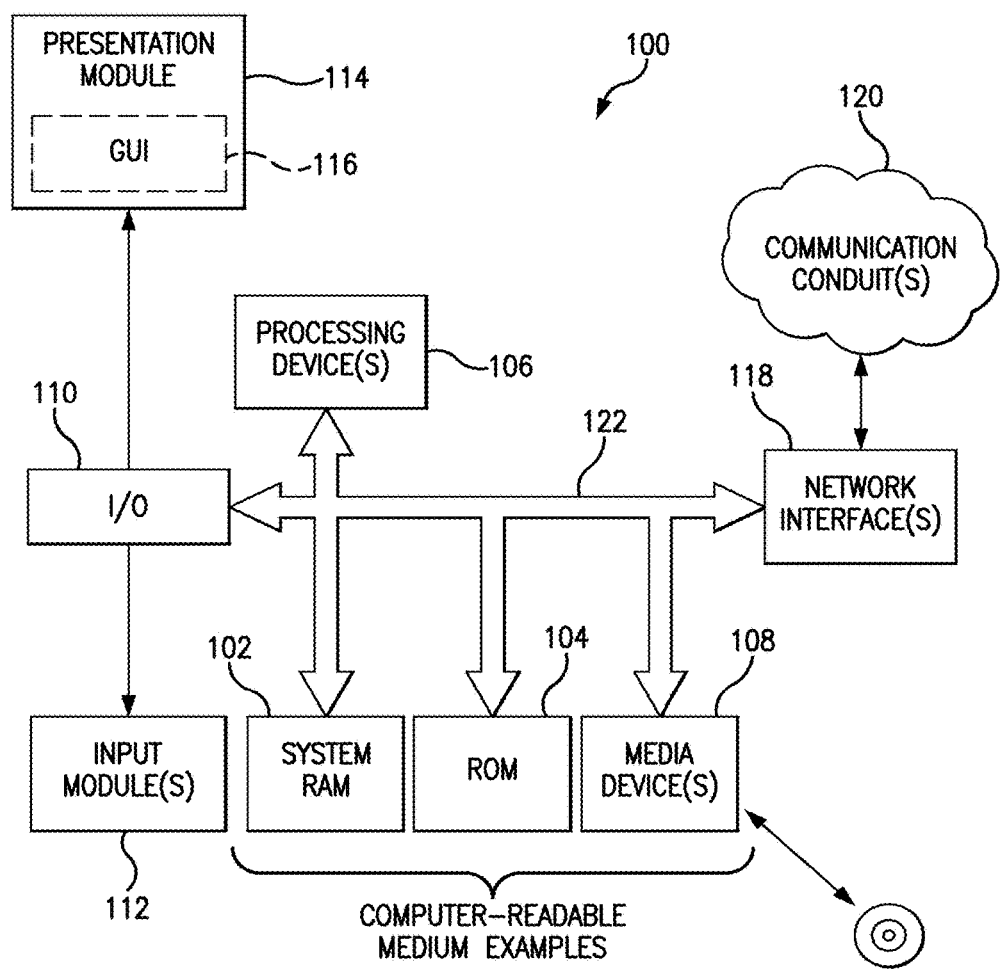
FIG. 1 shows an exemplary computing environment in which embodiments of the presently disclosed methods and systems may be implemented.

Now referring to the figures, wherein like numbers represent like elements, intraoral tactile biofeedback methods, devices and systems as described herein may be implemented in connection with a computing device (including a mobile networking apparatus) that includes hardware, software, or, where appropriate, a combination of both. FIG. 1 sets forth illustrative electrical data processing functionality 100 that can be used to implement aspect of the functions described herein. In one case, the processing functionality 100 may correspond to a computing device that includes one or more processing devices. The computing device can include a computer, computer system or other programmable electronic device, including a client computer, a server computer, a portable computer (including a laptop and a tablet), a handheld computer, a mobile phone (including a smart phone), a gaming device, an embedded controller and any combination and/or equivalent thereof (including touchless devices). Moreover, the computing device may be implemented using one or more networked computers, e.g., in a cluster or other distributed computing system. It is understood that the exemplary environment illustrated in FIG. 1 is not intended to limit the present disclosure, and that other alternative hardware and/or software environments may be used without departing from the scope of this disclosure.

For clarity, as used herein, the term "server" includes one or more servers. A server can include one or more computers that manage access to a centralized resource or service in a network. A server can also include at least one program that manages resources (for example, on a multiprocessing operating system where a single computer can execute several programs at once). Further, the terms "computing device", "computer device", "computer" and "machine" are understood to be interchangeable terms and shall be taken to include any collection of computing devices that individually or jointly execute a set (or multiple sets) of instructions to perform any one or more of the methods discussed herein.

The processing functionality 100 can include volatile memory (such as RAM 102) and/or non-volatile memory (such as ROM 104 as well as any supplemental levels of memory, including but not limited to cache memories, programmable or flash memories and read-only memories). The processing functionality can also include one or more processing devices 106 (e.g., one or more central processing units (CPUs), one or more graphics processing units (GPUs), one or more microprocessors (µP) and similar and complementary devices) and optional media devices 108 (e.g., a hard disk module, an optical disk module, etc.).

The processing functionality 100 can perform various operations identified above with the processing device(s) 106 executing instructions that are maintained by memory (e.g., RAM 102, ROM 104 or elsewhere). The disclosed method and system may also be practiced via communications embodied in the form of program code that is transmitted over some transmission medium, such as over electrical wiring or cabling, through fiber optics, wirelessly or via any other form of transmission, wherein, when the program code is received and loaded into and executed by a machine, such as an EPROM, a gate array, a programmable logic device (PLD), a client computer, or the like, the machine becomes an apparatus for practicing the presently disclosed system and method. When implemented on a general-purpose processor, the program code combines with the processor to provide a unique apparatus that operates to invoke the functionality of the presently disclosed system and method. Additionally, any storage techniques used in connection with the presently disclosed method and/or system may invariably be a combination of hardware and software.

The processing functionality 100 also includes an input/output module 110 for receiving various inputs from a user (via input modules 112) and for providing various outputs to the user. One particular output mechanism may include a presentation module 114 and an associated graphical user interface (GUI) 116 incorporating one or more I/O devices (including but not limited to a display, a keyboard/keypad, a mouse and/or other pointing device, a trackball, a joystick, a haptic feedback device, a motion feedback device, a voice recognition device, a microphone, a speaker, a touch screen, a touchpad, a webcam, 2-D and 3-D cameras, and similar and complementary devices that enable operative response to user commands that are received at a computing device).

Otherwise, user input may be received via a computing device coupled to another computing device over a network. The processing functionality 100 can also include one or more network interfaces 118 for exchanging data with other devices via one or more communication conduits 120. One or more communication buses 122 communicatively couple the above-described components together. Bus 122 may represent one or more bus structures and types, including but not limited to a memory bus or memory controller, a peripheral bus, a serial bus, an accelerated graphics port, a processor or local bus using any of a variety of bus architectures and similar and complementary devices. This configuration may be desirable where a computing device is implemented as a server or other form of multi-user computer, although such computing device may also be implemented as a standalone workstation, desktop, or other single-user computer in some embodiments. In such configuration, the computing device desirably includes a network interface in operative communication with at least one network. The network may be a LAN, a WAN, a SAN, a wireless network, a cellular network, radio links, optical links and/or the Internet, although the network is not limited to these network selections. It will be apparent to those skilled in the art that storage devices utilized to provide computer-readable and computer-executable instructions and data can be distributed over a network.

The computing device can operate under the control of an operating system that executes or otherwise relies upon various computer software applications. For example, a database management system (DBMS) may be resident in the memory to access one or more databases (not shown). The databases may be stored in a separate structure, such as a database server, connected, either directly or through a communication link, with the remainder of the computing device. Moreover, various applications may also execute on one or more processors in another computer coupled to the computing device via a network in a distributed or client-server computing environment.

Figure 2:
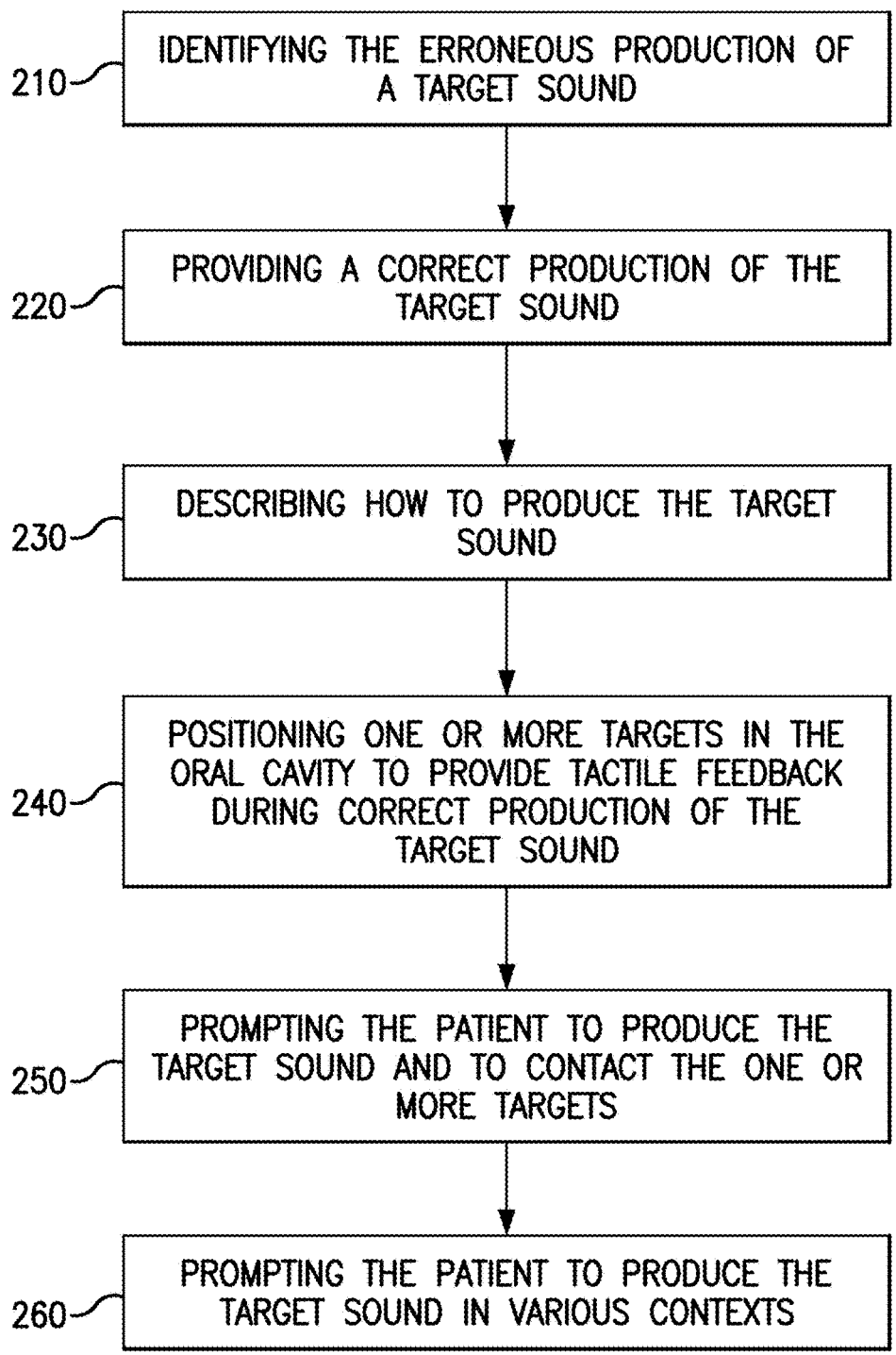
FIGS. 2, 3 and 4 show flowcharts of exemplary implementations of methods for training pronunciation accuracy.

With reference now to FIG. 2, a user can initiate an exemplary intraoral tactile feedback method by initiating process 200 for providing intra-oral feedback in speech training/therapy. As used herein, a "user" may be a single user or a group of users and may include individual speakers, family members, friend, colleagues, medical and therapy personnel and any other person, group of persons or entity engaged in the speaker's speech development. As used herein, the term "user" (or "user device", "client device", "network-connected device" or "device") can refer to any electronic apparatus configured for receiving control input and configured to send commands or data either interactively or automatically to other devices. A user device can be an instance of an online user interface hosted on servers as retrieved by a user. As used herein, the term "process" or "method" may include one or more steps performed at least by one electronic or computer-based apparatus. Any sequence of steps is exemplary and is not intended to limit methods described herein to any particular sequence, nor is it intended to preclude adding steps, omitting steps, repeating steps, or performing steps simultaneously.

A process 200 starts when a user accesses an intraoral tactile feedback system. In the examples below, a user may be a "therapist", which is used herein as an exemplary term, although it is understood that non-therapists can execute process 200. Access may be granted via a network interface that presents a login page (not shown) for the intraoral tactile feedback system. The login page may have a variety of appearances and applications as understood by a person of ordinary skill in the art. In some embodiments, a log-in may not be immediately presented but may be accessible from another web page or from a mobile application.

In step 210, a therapist identifies the erroneous production of a speech sound ("target sound"). It is understood that the target sound may be adjusted as necessary in order to provide tactile feedback of the proper position of the speaker's tongue and thereby achieve proper production of the target sound. In step 220, the therapist provides a correct production of the target sound and an incorrect production of the error target sound and asks the speaker to distinguish which is correct. Step 220 may be repeated as the therapist deems necessary, for example, to acquire an acceptable "correct" target sound as a baseline and/or to provide the speaker with ample opportunity to distinguish between correct and error target sounds. In step 230, the therapist describes to the patient how to configure his tongue to properly create the target sound. In step 240, the therapist positions one or more targets or nodes in the patient's oral cavity to indicate the proper position of the tongue for producing the target sound through tactile feedback to the patient. In step 250, the therapist prompts the patient to produce the target sound and contact the target with his tongue. Steps 230, 240, and 250 may be repeated as necessary until the speaker properly produces the target sound.

In step 260, the therapist prompts the speaker to properly produce the target sound in various contexts. Step 260 may occur after the patient is able to properly produce the target sound, thereby reinforcing the correct production of the target sound in multiple contexts.

Figure 3:
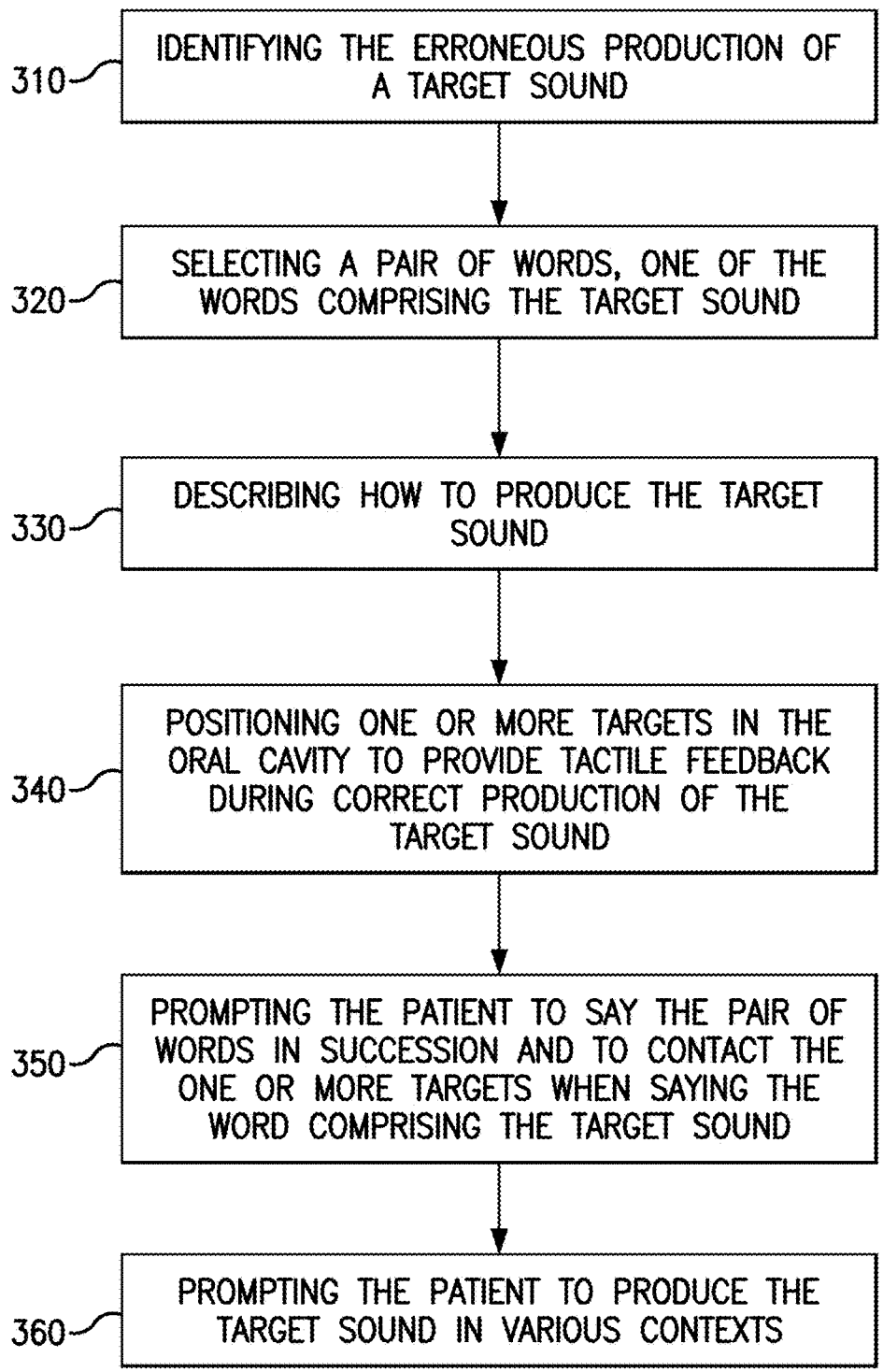

With reference now to FIG. 3, a user can initiate an exemplary intraoral tactile feedback method by initiating an exemplary process 300 for providing intra-oral feedback in speech training/therapy. In step 310, a therapist identifies the erroneous production of a sound ("target sound"). It is understood that the target may be adjusted as necessary in order to provide tactile feedback of the proper position of the speaker's tongue and thereby achieve proper production of the target sound. In step 320, the therapist selects a minimal pair of words that are identical except with respect to the target sound and a sound that the speaker produces correctly. For example, if a speaker incorrectly produces the /s/ sound and correctly produces the sound /t/, the therapist may select the pair of words /sip/ and /tip/. In step 330, the therapist describes to the speaker how to configure his tongue to properly create the target sound. In step 340, the therapist positions one or more targets in the speaker's oral cavity to indicate the proper position of the tongue for producing the target sound through tactile feedback to the speaker. In step 350, the therapist prompts the speaker to say the selected pair of words in succession and to contact the target with his tongue while saying the word containing the target sound. Steps 330, 340, and 350 may be repeated as necessary until the speaker properly produces the target sound. Also, steps 320, 330, 340, and 350 may be repeated by selecting another pair of words.

In step 360, the therapist prompts the speaker to properly produce the target sound in various contexts. Step 360 may occur after speaker is able to properly produce the sound, thereby reinforcing the correct production of the target sound in multiple contexts. The implementation of process 300 shown in FIG. 3 trains the speaker to distinguish the target sound from a sound he already correctly produces by highlighting differences between the sounds in the selected pair of words. Intra-oral tactile feedback allows the speaker to feel the difference between the sounds in the selected pair of words and enhances the contrast between correct and incorrect productions of the target sound. This process allows the speaker to train his somatosensory (i.e., higher level, innate feeling, and understanding of correct versus incorrect production of the target sound) and auditory systems to properly produce the target sound.

Figure 4:
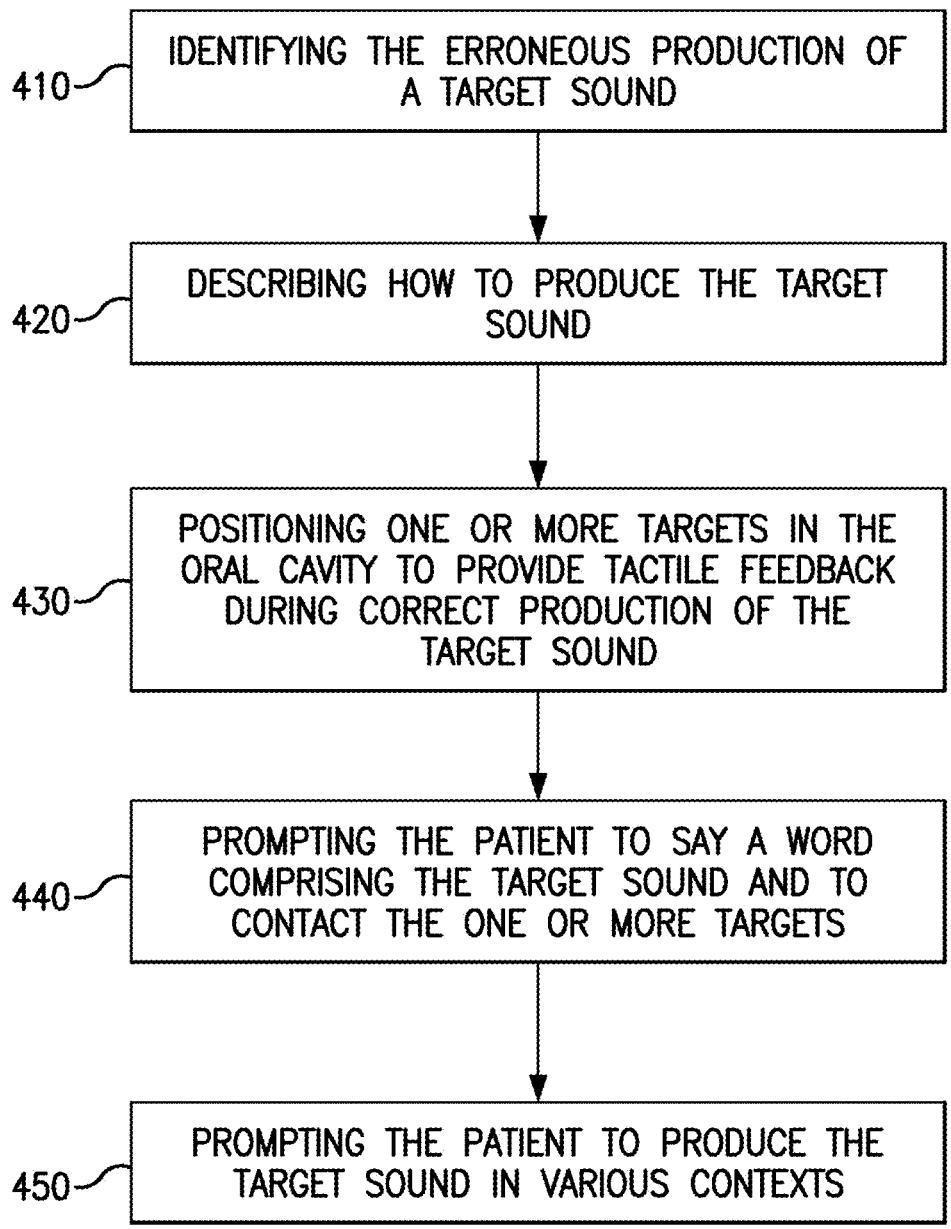

With reference now to FIG. 4, a user can initiate an exemplary intraoral tactile feedback method by initiating an exemplary process 400 for providing intra-oral feedback in speech training/therapy. In step 410, a therapist identifies the erroneous production of a sound ("target sound"). It is understood that the target may be adjusted as necessary in order to provide tactile feedback of the proper position of the tongue and achieve proper production of the target sound. In step 420, the therapist describes to the speaker how to configure his tongue to properly create the target sound. In step 430, the therapist positions one or more targets in the speaker's oral cavity to indicate the proper position of the tongue for producing the target sound through tactile feedback to the speaker. In step 440, the therapist prompts the speaker to say a word containing the target sound and to contact the target with his tongue. Step 440 may be repeated with different words. Also, steps 420, 430 and 440 may be repeated as necessary until the speaker properly produces the target sound.

In step 460, the therapist prompts the speaker to properly produce the target sound in various contexts. Step 460 may occur after the patient is able to properly produce the target sound, thereby reinforcing the correct production of the target sound in multiple contexts. This implementation of process 400 presents the speaker with the target sound in many different co-articulatory contexts so that the speaker is exposed to the target sound opposed with many other sounds. By presenting the target sound in many different contexts, the speaker will more accurately perceive the target sound and will more accurately perceive how to reproduce the target sound. Providing intra-oral tactile feedback during repetitions of words containing the target sound allows the speaker to better physically perceive accurate production of the target sound in various contexts.

Sensors and Features

Sensors and physical nodes that enable tactile feedback can be placed within a speaker's mouth precisely in specific zones. As the oral articulators, particularly the tongue, navigate to this zone, the detection of their proximity, position, and movement can be measured. This measurement can be used as a teaching method which is important for the generation of specific sounds, sound patterns, sound combinations, words, and sentences.

More specifically sensors can be used to determine the difference between a correct and an incorrect pronunciation of a specific sound. Different shaped devices can be used that place these sensors and nodes in various locations within a speaker's oral cavity. These locations can correspond to the following consonant phonemes: /b/, /d/, /f/, /g/, /h/, /j/, /k/, /l/, /m/, /n/, /p/, /r/, /s/, /t/, /v/, /w/, /y/, /z/, /th/, /ng/, /sh/, /ch/, /zh/, /wh/, as well as vowel phonemes /a/, /e/, /i/, /o/, /u/, /ā/, /ē/, /ī/, /ō/, /ū/, /oo/, /ōō/, /ow/, /oy/, /a(r)/, /ā(r)/, /i(r)/, /o(r)/, /u(r)/.

In the methods described above, and in commensurate methods, at least one step includes positioning one or more targets in the speaker's oral cavity to indicate the proper position of the tongue for producing the target sound through tactile feedback to the speaker. Different sounds require different tongue positions, and the target will be positioned in different locations in the speaker's oral cavity depending on the target sound being treated or trained. Sensor placement is therefore imperative in the determination of a correct and an incorrect pronunciation. For each phoneme, the sensor placement and sensitivity is unique.

Correct pronunciation will be detected when the tongue is lightly touching the target. In one form of incorrect pronunciation, the sensor can detect when the speaker's tongue does not move forward enough to touch the target. In another form of incorrect pronunciation, a sensor (such as a force sensor) can detect when the speaker's tongue touches the sensor too hard. In addition, a sensor can be used to detect correct positioning of the device, for example, by determining if the sensor (and thereby the device) is up against the palate properly or not.

Figure 5:
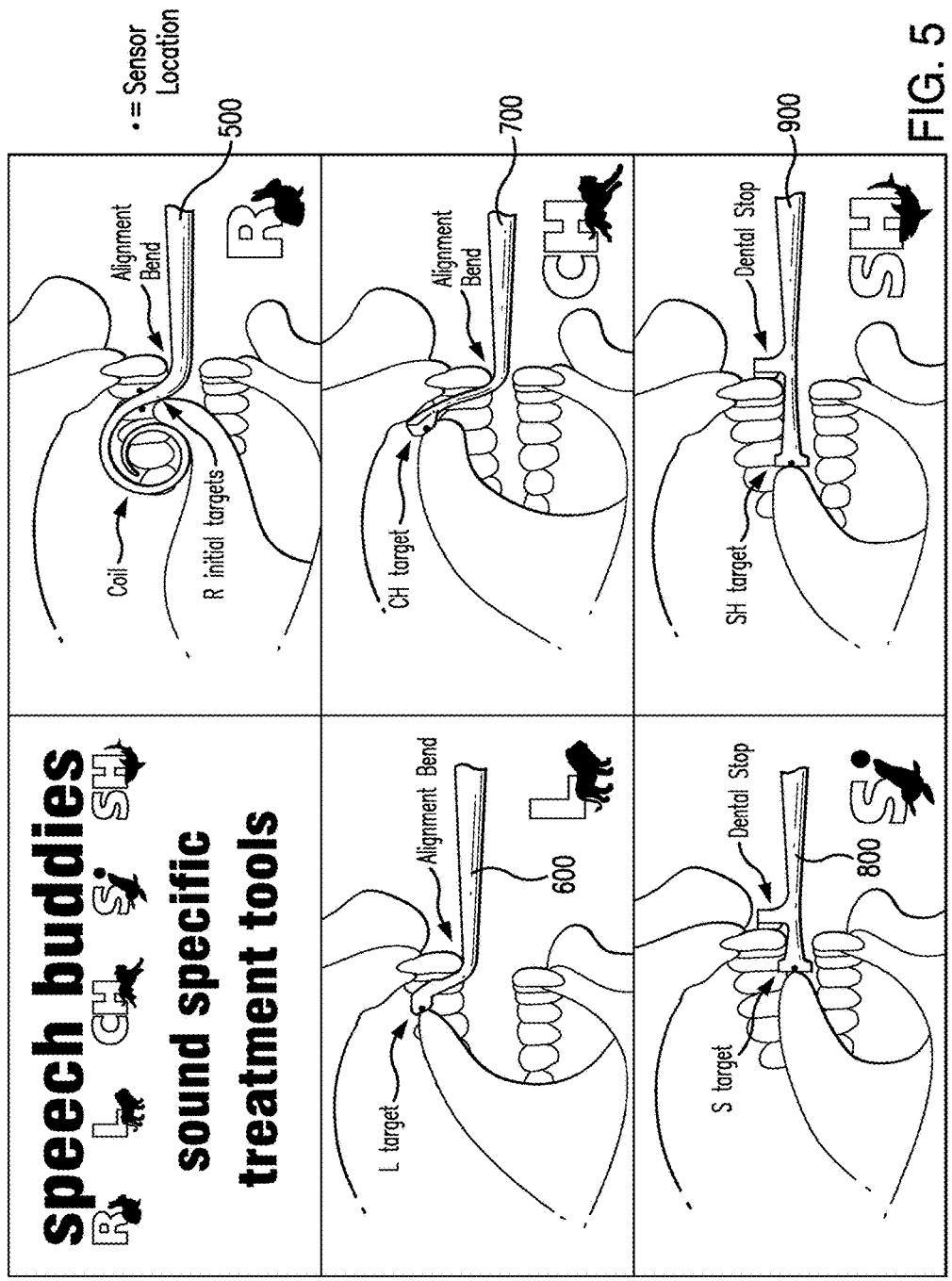
FIG. 5 shows examples of target locations at which sensors can be placed within a speaker's oral cavity, with the target locations corresponding to the proper lingual positions for the production of various speech sounds.

FIG. 5 shows examples of target locations at which sensors can be placed within the oral cavity. These target locations correspond to the proper lingual positions for the production of various speech sounds. For example, a small array of pressure sensors can be attached to devices in a minimally invasive fashion as to not impede speech. Expanded detail on intraoral feedback methods and devices are described hereinbelow with reference to sensors that are placed on exemplary devices 500, 600, 700, 800 and 900.

The successful practice of each device is not limited by the type of sensors used therewith. Therefore, it is contemplated that each device may incorporate at least one of an optical sensor, a force sensing resistor, a bridge sensor (which takes advantage of the fact that there is saliva in the mouth and aids in the process of forming an electrical connection), a capacitive sensor, a strain gauge sensor and any equivalent and combination thereof. In devices employing more than one sensor, or employing a sensor array, more than one type of sensor may be utilized in consideration of the unique sensor placement and sensitivity contemplated by the determination of correct and incorrect pronunciations.

Devices

An intraoral method and system may be realized with one or more intraoral tactile biofeedback devices, including but not limited to exemplary devices 500, 600, 700, 800 and 900 shown in FIG. 5 and discussed further hereinbelow. Each device indicates the proper lingual position corresponding to one or more particular speech sounds by providing intraoral tactile feedback. While the devices are applicable to the methods of treatment/training described above, they may also be applicable to other methods of treatment not described herein. The devices are minimally invasive and sympathetic to the contours of the oral cavity, thereby allowing unimpeded co-articulation (the natural transition of one speech sound or phoneme into another needed for forming words and sentences) while aiding in the exact lingual positioning required for accurate productions of specific speech sounds. These features allow smooth transitions during a therapy regimen and "natural" sounding speech while focusing on specific speech sounds.

Each device includes one or more sensors disposed on a head that is inserted into in a speaker's oral cavity during a treatment or practice session. Sensors on the head can detect correct and incorrect pronunciations as well as a degree of correctness or accuracy (e.g., on a scale of 1-5 or 1-10). The head cooperates with a handle that is gripped by the speaker or by or any other user engaged in a speech practice session with the speaker (e.g., therapist, family member, teacher, etc.). The head and handle may be provided as a co-molded or co-extruded integral member. The head and handle may alternatively be provided as separately fabricated members each including a magnet therein for detachable engagement with one another. Engagement may be effected by other engagement means including, but not limited to, mating notches and recesses, frictional fit members, snap-tight engagement or any other means for detachable engagement of the head and handle relative to one another. These can be used separately or in combination with the magnets.

The sound training device preferably includes fiber optic segments that are operably linked with an optical detector and emitter to assist in placement of the sensor in the speaker's mouth.

When the device is an electromechanical system, the handle houses an onboard computer and communication to a computing device (e.g., a PC, tablet, smartphone, mobile device or any other equivalent device) while the detachable head contains one or more sensors. The connection not only makes a mechanical connection to the device head but also an electrical connection between the sensor(s) and the onboard computer.

The sensor communicates information from each sensor to at least one of the onboard computer and an offboard computer. In the case of an onboard computer, this information is communicated wirelessly to a device (such as a PC, tablet, smartphone, mobile device or other computing device) which then communicates with one or more software applications, including but not limited to lesson and gaming software applications. In the case of an offboard computer, the offboard computer can communicate with a software application running thereon and/or running in cooperation with one or more other software applications.

At least one software application can communicate to the speaker and/or other user(s) information representing the interaction of the device with the speaker's mouth, tongue and/or oral cavity and the accuracy of sound production. This information may be accessible via a platform that supports collaborative therapy-focused social networking over a network. Such networking may take place in a 3-D virtual environment.

The head and handle may be fabricated from a range of suitable materials, including plastics (e.g., elastomers, urethanes, polypropylene, ABS, polycarbonate, polystyrene, PEEK, silicone, etc.), metals (stainless steel, titanium, aluminum, etc.), ceramics, ceramic composites and any equivalent and combination thereof. Each portion may be fabricated from a material that is different than the material composition of the other portion (for example, insertion portion may be fabricated from a plastic composite and handle portion may be fabricated from a metal). For multi-part devices, different parts may exhibit different grades of stiffness. For example, a part may be co-molded to create a soft layer above or below a hard layer, or alternating soft and hard layers may be fabricated into an integral device.

These materials may be disposable, reusable and/or recyclable. Thus, each device may be designed in its entirety as a disposable or re-usable device, or specific components may be designed as disposable or reusable components that may be interchangeable. Detachable heads and handles also lend to the ease of cleaning of each device.

Devices may be provided in exemplary kits in which one or more multiple handles may be interchangeable with one or more heads. Handles adapted to accommodate users of varying ages and abilities may be provided in a kit with one or more heads adapted to address different phonemes. Alternatively, one handle having an onboard computer may be provided in a kit with multiple different heads.

Figure 6:
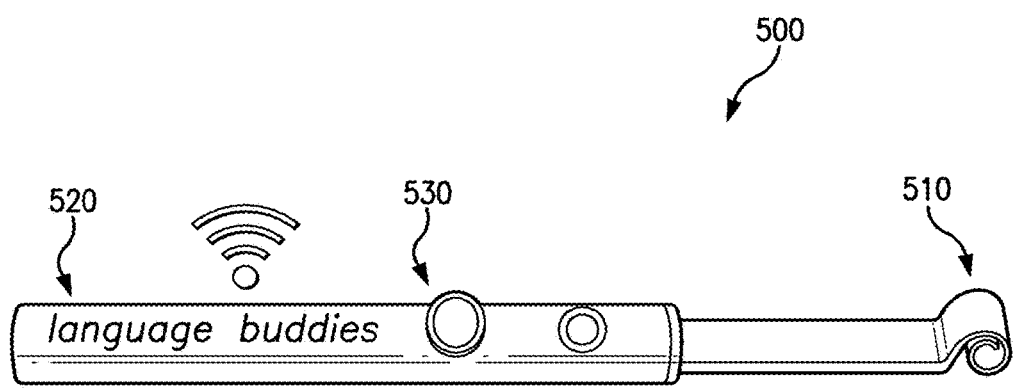
FIG. 6 shows a top perspective view of an exemplary device for teaching retroflection of a speaker's tongue when training the correct production of the /r/ sound.
Figure 6A:
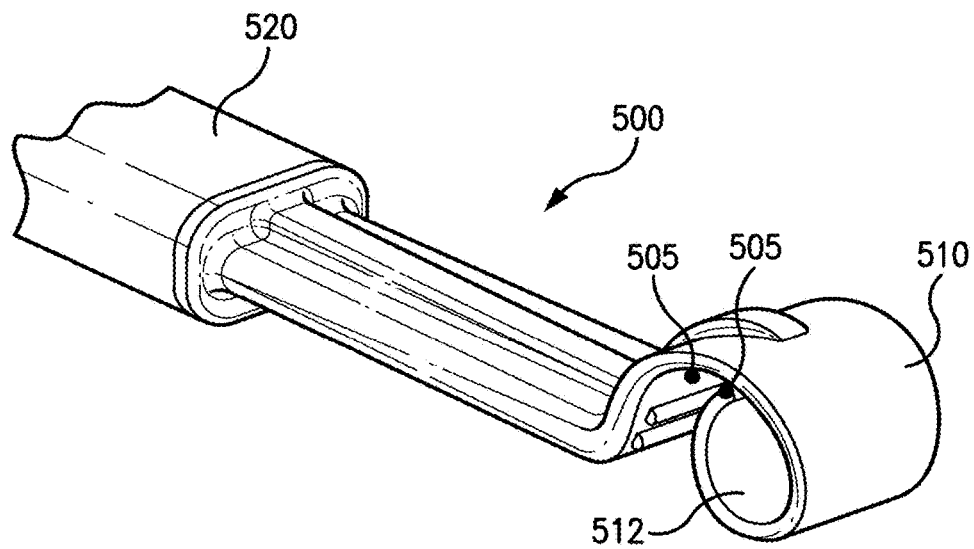
FIG. 6A shows a partial side perspective view of the device of FIG. 6.
Figure 6B:
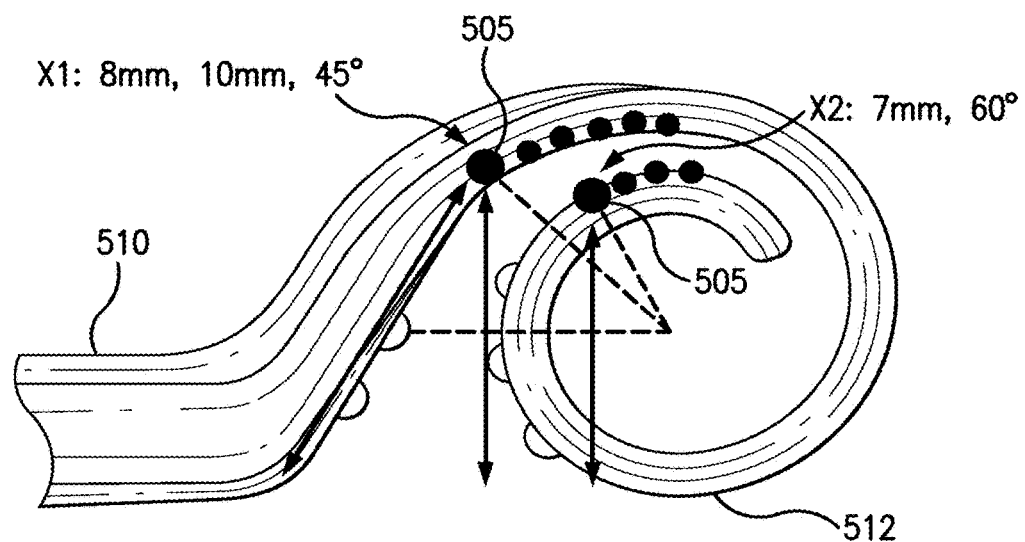
FIG. 6B shows a partial side view of a head of the device of FIG. 6 having sensors strategically disposed thereon.

R Phoneme:

Referring now to FIGS. 6, 6A and 6B, an exemplary device 500 is shown for teaching retroflection of the tongue when training the correct production of the R sound. Device 500 includes a head 510 having one or more sensors 505 strategically disposed thereon (for example, at locations X1 and X2 as seen in FIGS. 6A and 6B). Head 510 includes a coil 512 for training this retroflection. The method of using a coil is a proven method; however, there are many options that can optimize this method and control more precisely the method of training the movement of the oral articulators. For example, a taper may be used on coil 512 to influence the stiffness, and thus the feedback of resistance, that is provided to the tongue. The larger the angle, or taper, the thinner the material section becomes, thus reducing the stiffness of the coil. The thickness of the coil can also influence and change the spring constant of the device and the subsequent feedback that is given. In an exemplary embodiment, the thickness of the coil may desirably be about 2 mm for an elastomeric material but may range between 0.025 m and 8 mm. In addition, the width of the coil, as well as the number of winds or degrees of the coil, may be factors in determining the optimal feedback. In an exemplary embodiment, the coil may have a width of about 12 mm but the width may have a range of between about 2 mm and 40 mm. The number of degrees of arc of the coil may be about 560° but can be in a range about 180° and 2000° of revolution.

Head 510 may be integral with, or detachably engaged with, a handle 520 having an onboard computer (not shown) incorporated in a housing thereof. The onboard computer may establish communication with a computing device or system via a wireless network. Alternatively, handle 520 may include structure for engagement with a computing device or system, for example, via a USB port or other connection. Either this engagement or the wireless communication provides the opportunity for device 500 to interact with various software applications.

Handle 520 may include an on/off button 530 or similar feature for connecting and disconnecting power to/from device 500. Power may be provided by an internal battery which may be rechargeable (for example, via the USB connection to a power source). A remote control may be used to turn device 500 on and off and also to upload and download any information obtained and/or generated by the onboard computer.

The /r/ sound is a difficult sound to produce because it involves a progressive superior and posterior movement of the tongue just below the hard palate. Device 500 functions because the coil is unwound by the user when a correct pronunciation is made, but does not unwind when an incorrect pronunciation is made. The sensor must be placed precisely in a location where it is triggered when the tongue unwinds or is about to unwind the coil, but it is not triggered when the coil is not unwound and an incorrect pronunciation is made. There may be multiple or single sensor locations, as shown by exemplary sensor locations X1 and X2 provided in FIGS. 6A and 6B. One exemplary sensor location X1 may be approximately 8 mm±7 mm above the base of the coil and approximately 10 mm±7 mm along the device above the bend. The location of X1 from the center of the coil is 45°±25° degrees from the base of the device (also measured from the flat resting position of the tongue). Another exemplary location X2 is on the coil itself at about 7 mm±6 mm from the base of the coil. This location is 60°±30° from the base of the device/flat resting position of the tongue. In this example, device 500 may incorporate sensors in one or both of locations X1 and X2.

Sensor sensitivity for the R phoneme is also considered for determining correct or incorrect pronunciations. The sensor could have an binary output, or the sensor (such as a capacitive sensor) can be used, to measure tongue/articulator proximity to the sensor (e.g., touching the sensor, 1 mm away, 2 mm away, 10 mm away, etc.). The sensitivity of the sensor may be dependent on the sensor's current and voltage through the sensor. For a bridge sensor, for example, which is essentially two electrical electrodes that are connected by the tongue, the current may be 5 mA (or within any range from about 0.001 mA to about 100 mA) and the voltage may be 6 Volts (or within any range from about 0.5V to about 400V). For this exemplary sensor configuration, electrode spacing between the positive and negative electrodes may be about 6 mm, or may range from about 2 mm to about 8 mm, or alternatively may range from about 0.05 mm to about 15 mm).

Device 500 is an exemplary embodiment of a device adapted to facilitate proper production of the /r/ sound, whether the patient generally produces /r/ with tongue retroflection or tongue retraction. When head 510 is inserted into the speaker's oral cavity, the sensors supported on coil 512 may be disposed below the palate to cue the progression of the tongue along a path that generates the /r/ sound.

Figure 7:
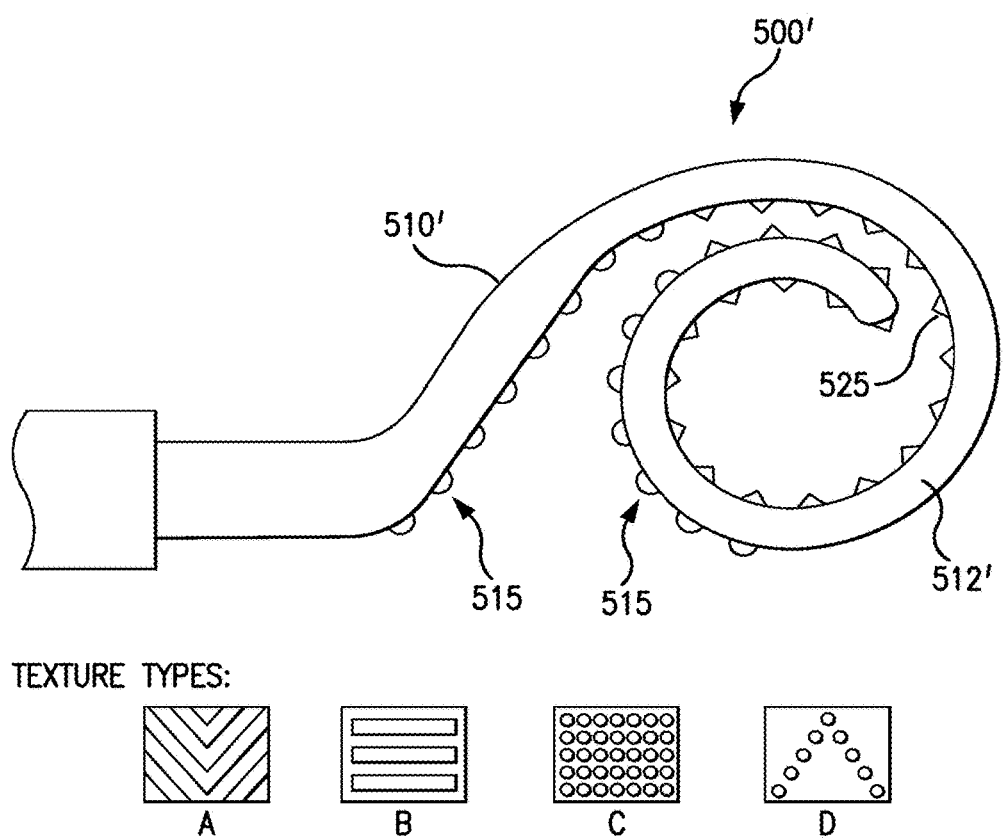
FIG. 7 shows a side view of another exemplary device for training the correct production of the /r/ sound.

FIG. 7 shows another exemplary device 500' having a head 510' and coil 512'. On device 500', one or more textures are added to coil 512' for determining the speaker's current motion of the /r/ production. Device 500' may incorporate textured protrusions 515 of one cross-sectional geometry to guide a specific starting point of the tongue as it initiates movement through the /r/ sound. Device 500' may also incorporate textured protrusions 525 of at least one other cross-sectional geometry that differs from that of protrusions 525. Protrusions 525 can indicate a different phase of movement through the /r/ sound. As an example, protrusions 515 may include semi-circular protrusions that represent the texture from the beginning of the tongue movement while protrusions 525 include triangles that represent the later stage of the tongue movement. Multiple configurations may be employed to enabling the speaker to know where she is within this range of motion. Exemplary textures are shown by texture types A (chevron), B (linear), C and D (dot matrices). It is understood that such textures are not limited to the particular geometries nor the particular numbers of protrusions shown. It is also understood that the protrusions may be provided with or replaced by recesses or other indicia. It is further understood that one or more sensors are easily integrated with such textures as shown with respect to device 500 such that the sensors sense movement throughout the /r/ sound and such movement is indicated via one or more software applications (for example, visually on a computer or mobile device display, aurally a microphone and or via haptic feedback).

Retracted R

Figure 8:
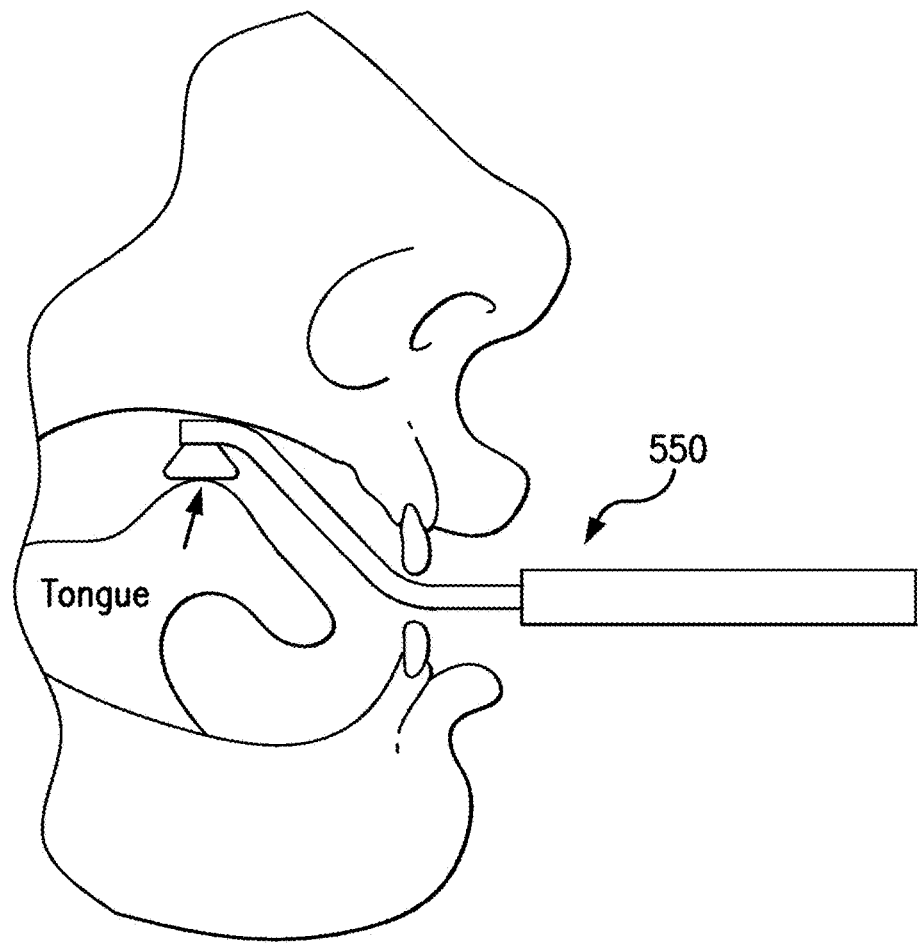
FIG. 8 shows an exemplary device in use for teaching the retracted method when training the correct production of the /r/ sound.

FIG. 8 shows an exemplary device used in an exemplary method often referred to as the "retracted", "bunched", "humpback" or "tongue tip down" method of teaching the R sound (as used herein, "retracted" method shall encompass all of these terms). For this method, a device 500 or 500' is used to teach the speaker to raise the mid-section of the tongue up while lowering the tip of the tongue. In this case, a node can be felt against the mid-section of the tongue, although it may or may not be touching the palate on top of the mouth.

Trilled R

Figure 9:
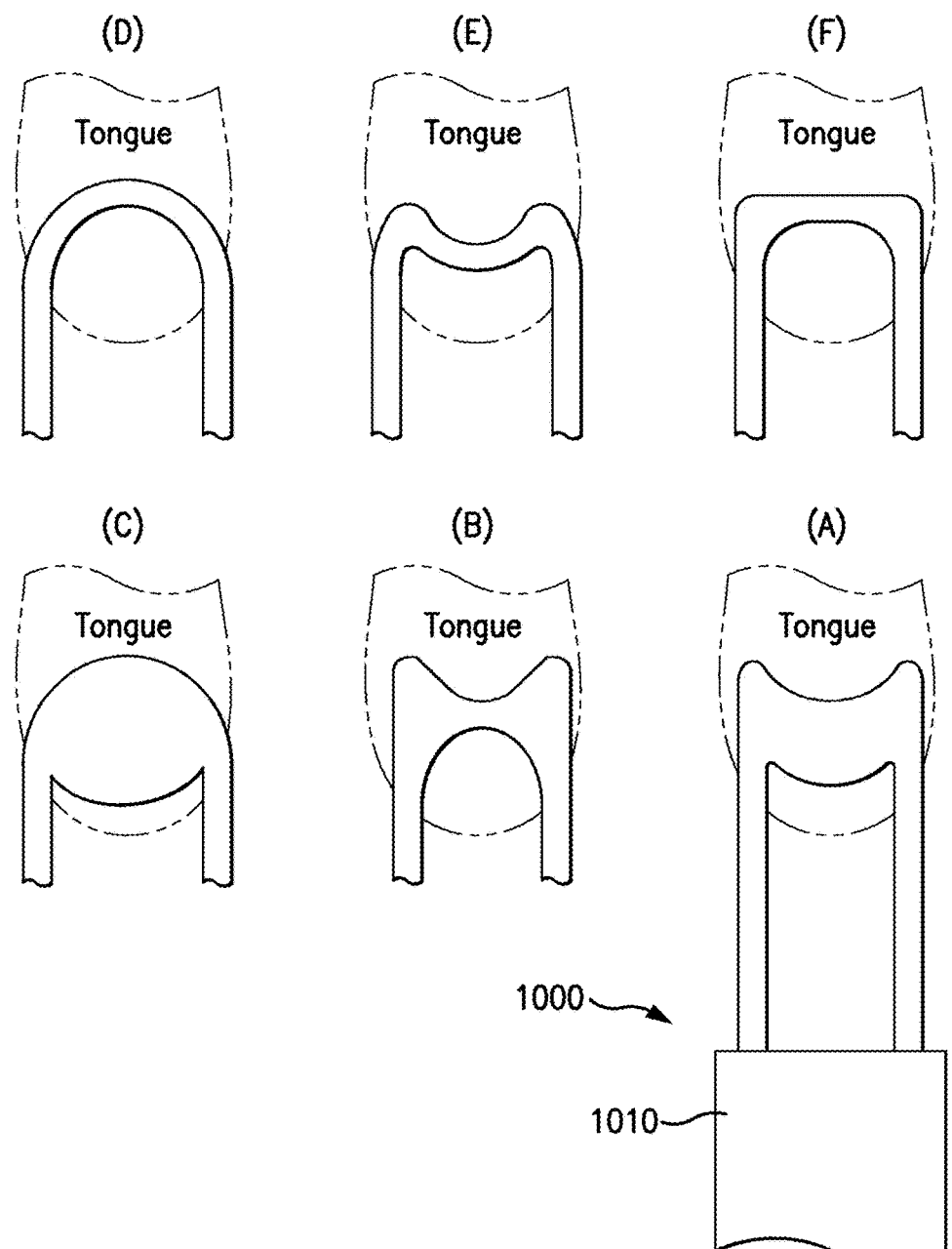
FIG. 9 shows an exemplary device for teaching the trilled R.

FIG. 9 shows an exemplary device 1000 used in an exemplary method for teaching the trilled R. The trilled R is an important sound in many languages, including but not limited to Italian, Spanish, French, German, Portuguese, Russian, and Arabic. FIG. 9 shows device 1000 having a handle 1010 that may include an onboard computer and have features similar to those shown and described with respect to handle 520. Handle 1010 may be interchangeable with one or more heads (A), (B), (C), (D), (E) and (F) to provide a method to stabilize the midsection of the tongue while allowing the very tip of the tongue to vibrate. Often the challenge with those who try and make the trilled R is that they try and vibrate too much of the tongue, including the mid-section. By stabilizing the mid-section of the tongue with the devices shown in FIG. 9, the correct trilled R can be produced. Once it is produced with the device, it can then be produced without the device. One or more sensors may be placed on one or more heads (A), (B), (C), (D), (E) and (F) to indicate the stabilization of the tongue midsection and further indicate the progression of the speaker's trilled R sound when referenced with an accurate trilled R sound.

Figure 10:
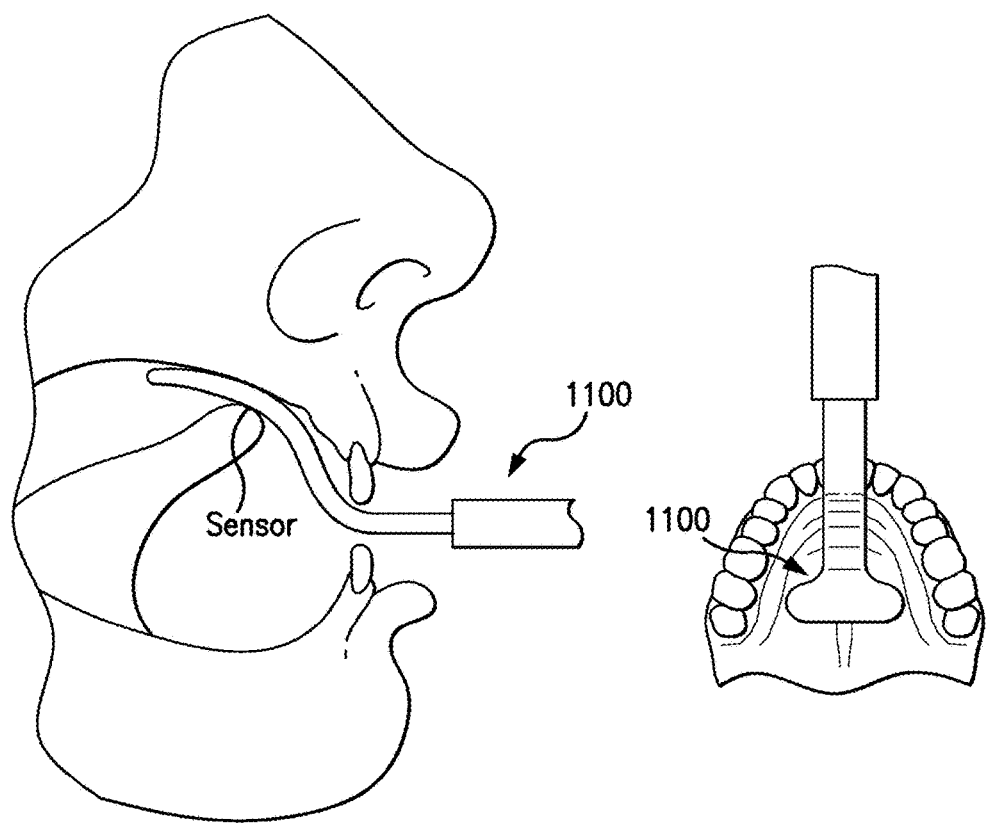
FIG. 10 shows another exemplary device in use for teaching the trilled R.

FIG. 10 shows another exemplary device 1100 used in an exemplary method for teaching the trilled R. When teaching the trilled R for the first time, an important step includes having the speaker start from a position with the speaker's tongue in contact with the palate. This contact then leads to a subsequent pressure build up, and then ultimately to the expulsion of air which allows the tongue tip to vibrate quickly. Device 1100 provides a surface against which the top front of the speaker's tongue contacts the device, thereby promoting a seal between the tongue and the alveolar ridge. The method supported by use of device 1100 verifies full palatal contact as required in preparation for the trilled R sound. This palatal contact is also essential for the American English /t/ sound. One or more sensors may be placed on device 1100 (for example, as indicated in FIG. 10) to indicate the seal and further indicate the progression of the speaker's trilled R sound when referenced with an accurate trilled R sound.

Blended R's

Figure 11:
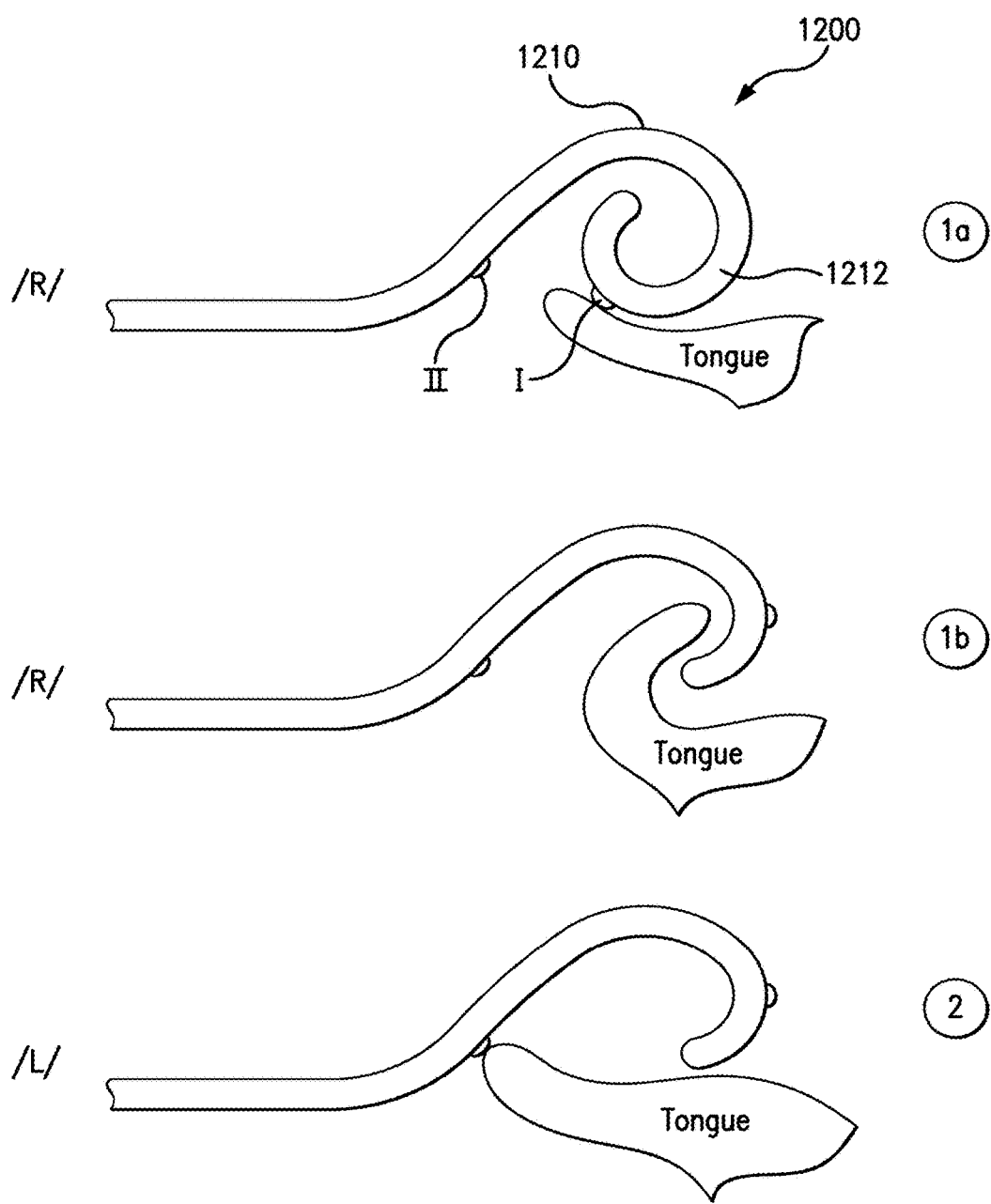
FIG. 11 shows an exemplary device for teaching blends or sequences of specific sounds.

FIG. 11 shows an exemplary device 1200 used in an exemplary method for teaching blends (or sequences) of specific sounds. Device 1200 is employed for the R-L blend, which is needed when pronouncing words like "girl". Device 1200 includes a head 1210 having a coil 1212 upon which a node of contact (I) is provided for the R sound and also a node of contact (II) is provided for the L sound in rapid succession afterwards. In this exemplary device, the coil should be long enough not to fully uncoil and snap back before the tongue is able to return and touch node (II) which prompts the /l/ sound. Sensors may be placed at one or more of nodes (i) and (II) to indicate successful pronunciation of the R-L blend and also to provide timing for the production of each of the /r/ and /l/ sounds. Even though device 1200 is described with respect to reinforcement of the R-L blend, it is understood that device 1200 and complements and equivalents thereof are contemplated, and that various combinations of sounds can be achieved when combining the concepts from multiple phonemes in one phoneme.

Japanese, Korean, Chinese L/R

Figure 12:
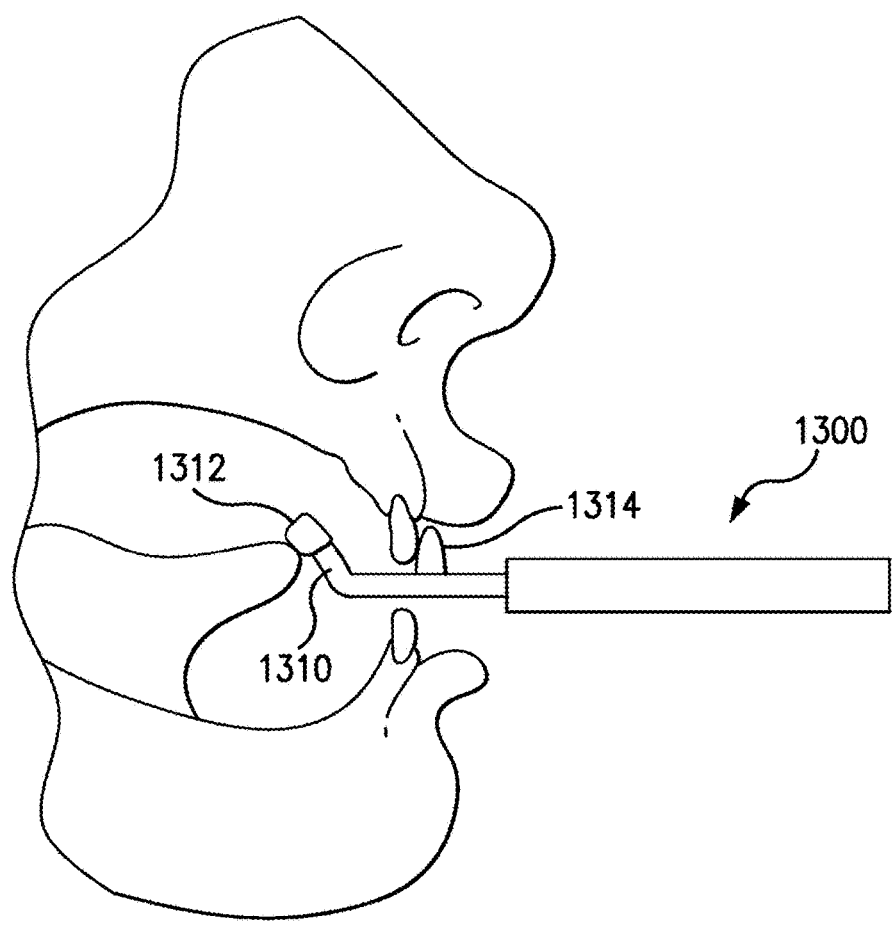
FIG. 12 shows an exemplary device in use for teaching the Japanese, Korean and Chinese L and R.

FIG. 12 shows an exemplary device 1300 used in an exemplary method for teaching the Japanese, Korean and Chinese L and R. Device 1300 includes a head 1310 having a node 1312 at which one or more sensors (not shown) may be disposed. Device 1300 may also include an optional tooth stop 1314 that guides node 1312 to a position in the vicinity of where the desired sound would be in the speaker's mouth. Sensors may be placed at or near node 1312 to indicate successful pronunciation of the Japanese, Korean and Chinese L and R. Sensors may optionally also be placed at or near tooth stop 1314 to indicate proper positioning of device 1300 in the speaker's mouth.

L Phoneme

Figure 13:
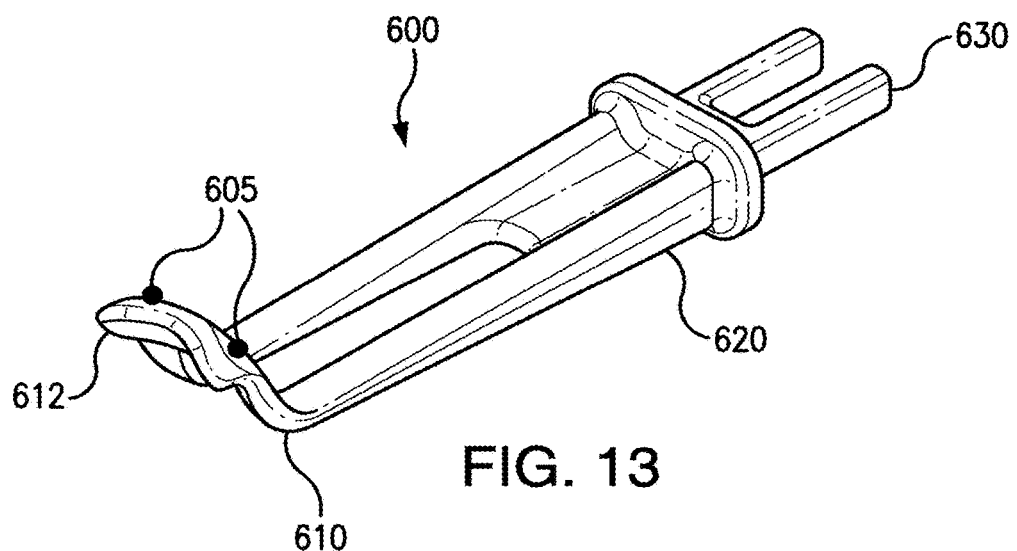
FIGS. 13 and 13A show top perspective and front views, respectively, of an exemplary device for teaching the correct production of the /l/ sound.
Figure 13A:
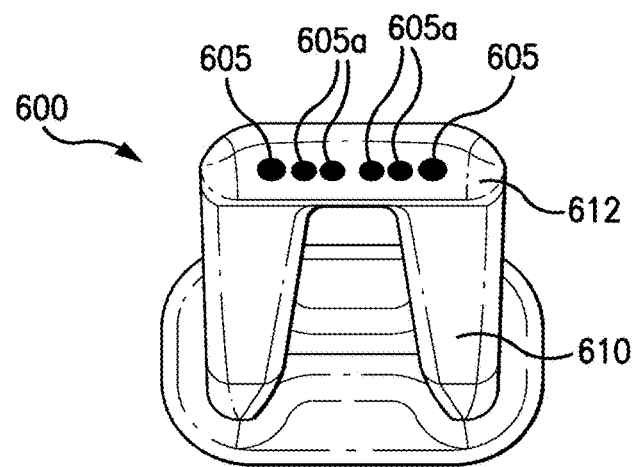

Referring now to FIGS. 13 and 13A, an exemplary device 600 is shown for teaching the correct production of the L sound. Device 600 may comprise an integral member or detachably engaged members including a head 610 and a handle 620. Handle 620 may house an onboard computer as described above and may also include structure for engagement with a computing device or system, for example, via a USB port or other connection. Exemplary structure is shown in FIG. 13 as a connector 630. It is understood, however, that any amenable structure may be employed that permits coupling of device 600 with one or more computing devices and communication of device 600 with various software applications. Alternatively, connector 630 may be replaced by gripping structure that enables a speaker or other user to grasp device 600 at a suitable distance from the speaker's mouth, as is known in the art.

Head 610 includes a node 612 having a tip upon which one or more sensors 605 may be disposed. Node 612 may have an inwardly-domed face that mimics the surface area of the tongue that contacts the alveolar ridge or teeth during normal sound production (see, for example, the /l/ node handle device described in co-owned U.S. Ser. No. 12/357, 239, the entire disclosure of which is incorporated by reference herein). Sensors 605 are desirably positioned so as to be parallel with the speaker's tongue tip during contact (see, for example, the locations of sensors 605 in FIGS. 13 and 13A). Sensors 605 as shown may include two individual sensors or may include two electrodes of one sensor. Alternative sensor locations 605a may be selected along node 612 for elective placement of sensors 605, which sensors are not limited to two sensors as shown. Sensors 605 as shown may be approximately 3 mm from the centerline with placement of accompanying electrodes in the middle of node 612.

Ch Phoneme

Figure 14:
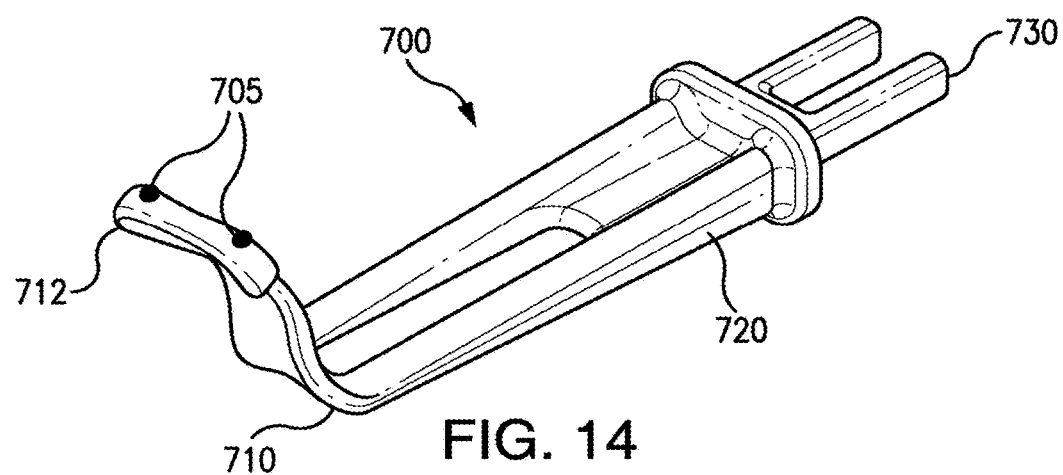
FIGS. 14 and 14A show top perspective and front views, respectively, of an exemplary device for teaching the correct production of the /ch/ sound.
Figure 14A:
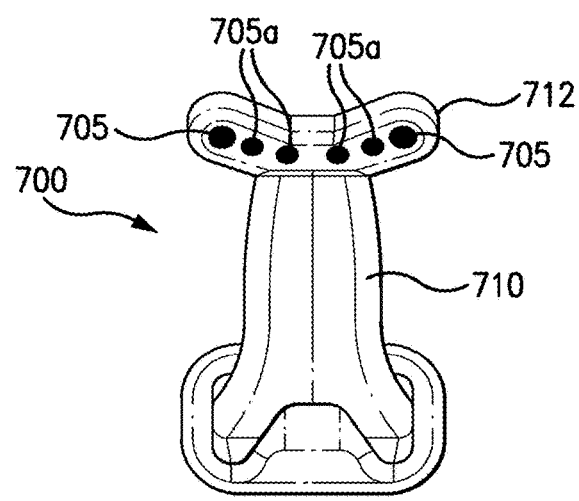

Referring now to FIGS. 14 and 14A, an exemplary device 700 is shown for teaching the correct production of the /ch/ sound. Device 700 may comprise an integral member or detachably engaged members including a head 710 and a handle 720. Handle 720 may house an onboard computer as described above and may also include structure for engagement with a computing device or system, for example, via a USB port or other connection. Exemplary structure is shown in FIG. 14 as a connector 730. Alternatively, connector 730 may be replaced by gripping structure that enables a speaker or other user to grasp device 700 at a suitable distance from the speaker's mouth, as is known in the art.

Head 710 includes a node 712 having a tip upon which one or more sensors 705 may be disposed. Node 712 is designed to remain in contact with the palate over a broad range of variation in anatomy, and sensors 705 are positioned appropriately (see, for example, the locations of sensors 705 in FIGS. 14 and 14A). Alternative sensor locations 705a may be selected along node 712 for elective placement of sensors 705, which sensors are not limited to two sensors as shown. Sensors 705 as shown may be approximately 3 mm from the centerline with placement of accompanying electrodes in the middle of node 712.

S and SH Phonemes

For the S and SH phonemes, sensors need to be placed in the tip of the node for sensing when lingual contact is made with the target.

Figure 15:
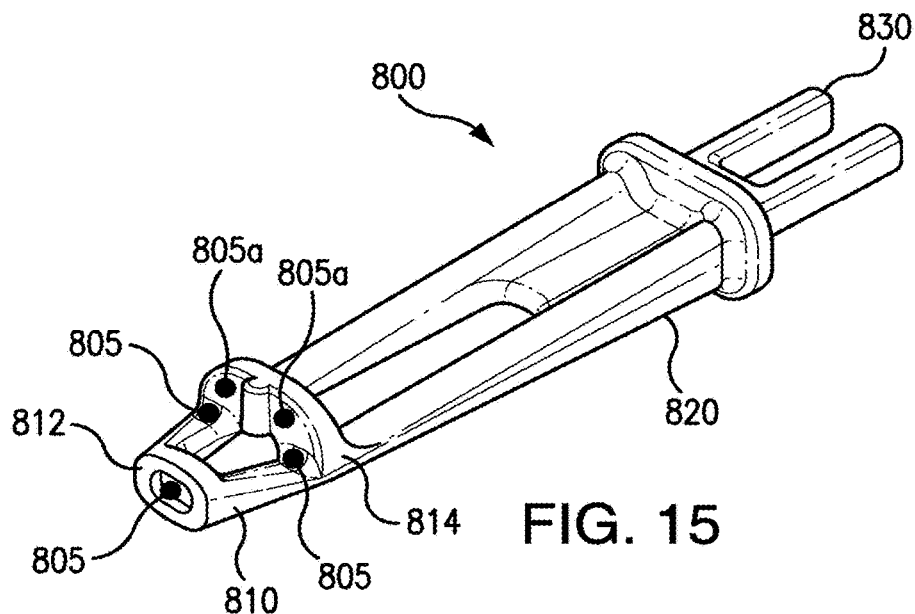
FIG. 15 shows a top perspective view of an exemplary device for teaching the correct production of the /s/ sound.

Referring now to FIG. 15, an exemplary device 800 is shown for teaching the correct production of the /s/ sound. Device 800 may comprise an integral member or detachably engaged members including a head 810 and a handle 820. Handle 820 may house an onboard computer as described above and may also include structure for engagement with a computing device or system, for example, via a USB port or other connection. Exemplary structure is shown in FIG. 15 as a connector 830 but may be complemented or replaced by gripping structure that enables a speaker or other user to grasp device 800 at a suitable distance from the speaker's mouth. Head 810 includes a node 812 having a tip upon which one or more sensors 805 may be disposed (see, for example, the locations of sensors 805 in FIG. 15). Device 800 may also include an optional tooth stop 814 that guides node 812 to a position in the vicinity of where the /s/ sound would be in the speaker's mouth (see also FIG. 5).

Figure 16:
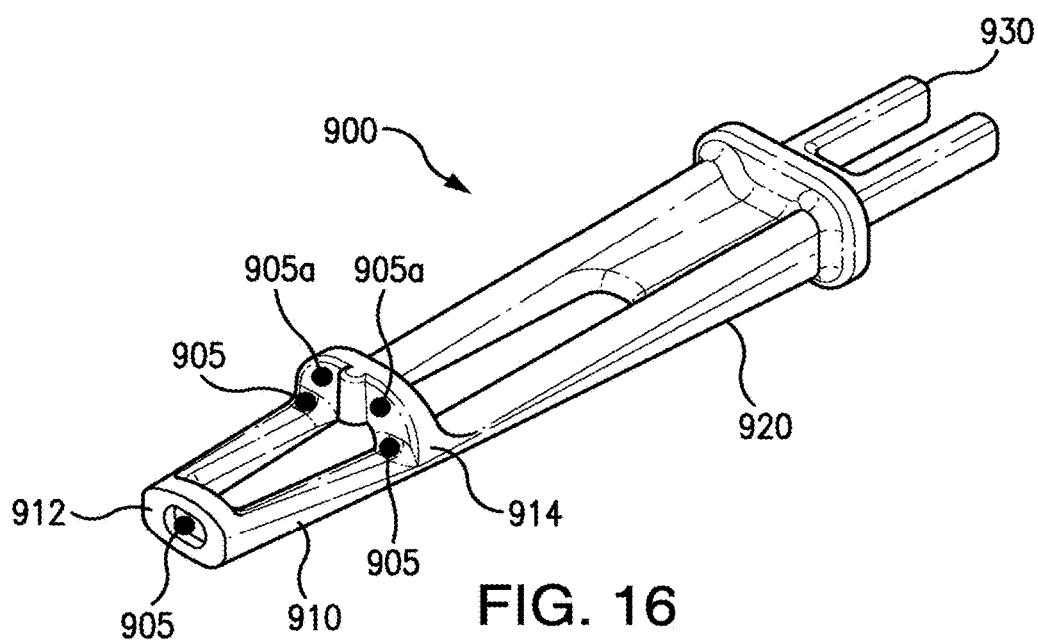
FIG. 16 shows a top perspective view of an exemplary device for teaching the correct production of the /sh/ sound.

Referring to FIG. 16, an exemplary device 900 is shown for teaching the correct production of the /sh/ sound. Device 900 may comprise an integral member or detachably engaged members including a head 910 and a handle 920 as described hereinabove with respect to device 800. Head 910 includes a node 912 having a tip upon which one or more sensors 905 may be disposed (see, for example, the locations of sensors 905 in FIG. 16). Like device 800, device 900 may also include an optional tooth stop 914 that guides node 912 to a position in the vicinity of where the /sh/ sound would be in the speaker's mouth (see also FIG. 5).

When using devices 800 and 900, correct pronunciation will be detected when the tongue is lightly touching the target. In one form of incorrect pronunciation, the sensor will detect when the speaker's tongue does not move forward enough to touch the target. In another form of incorrect pronunciation, the force sensor may determine when the speaker's tongue touches the sensor too hard (e.g., to produce "Thock" instead of "Sock"). Alternatively, a sensor located in optional sensor locations 805*a* (FIG. 15) and 805*a* (FIG. 16) can detect deflection of the respective device and thereby determine an incorrect pronunciation (i.e., a deflection means an incorrect pronunciation). In addition, the sensors can be used to detect correct positioning of the device, for example, by placing sensors at positions 805*a*, 905*a* to sense if the device is positioned up against the front teeth properly. An incorrect pronunciation where the tongue touches the target too hard may also be detected by the sensors in locations 805*a*, 905*a*, since the tongue will physically push the respective device off of the front teeth. All of these sensing locations may be populated with one sensor or by one or more sensor arrays.

The SH Sound

Figure 17:
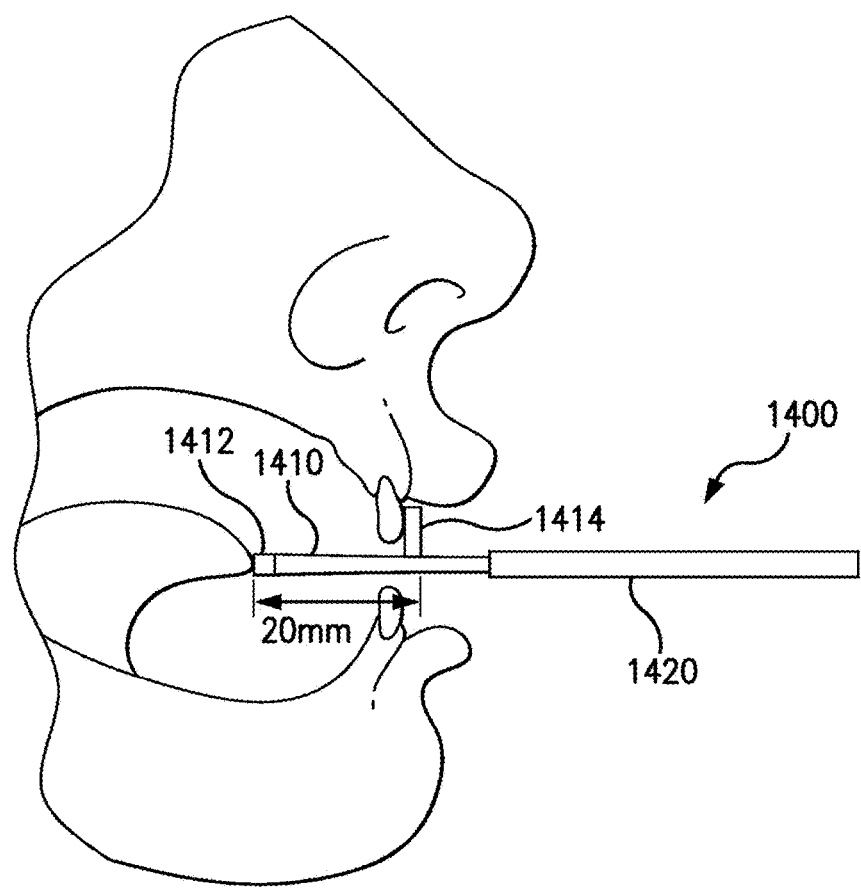
FIG. 17 shows an exemplary device in use for teaching the Chinese SH.

FIG. 17 shows an exemplary device 1400 used in an exemplary method for training the Chinese SH, which is slightly further back in the mouth than the English SH. Device 1400 includes a head 1410 having a node 1412 at which one or more sensors (not shown) may be disposed. Device 1400 may also include an optional tooth stop 1414 that guides node 1412 to a position in the vicinity of where the Chinese /sh/ sound would be in the speaker's mouth. Sensors may optionally be placed at or near tooth stop 1414 to indicate such position. Sensors may be also be placed at or near node 1412 to indicate successful pronunciation of the Chinese SH.

The F or V Sound

Figure 18:
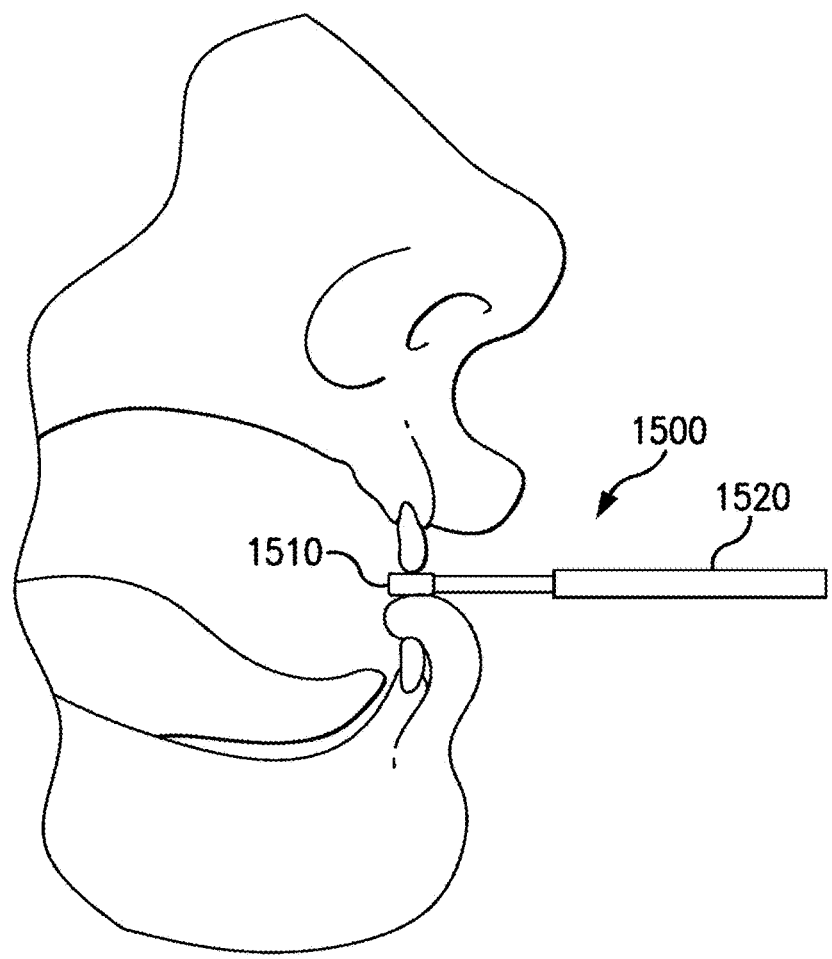
FIGS. 18 and 18A show an exemplary device in use for training the English /f/ or /v/ sound.

FIG. 18 shows an exemplary device 1500 used in an exemplary method for training the English /f/ or /v/ sound. These sounds may be very challenging for Chinese, Japanese, and Korean speakers who are learning to speak English. Device 1500 is shown with the tongue and teeth position to pronounce the English /f/ or /v/ sound.

Figure 18A:
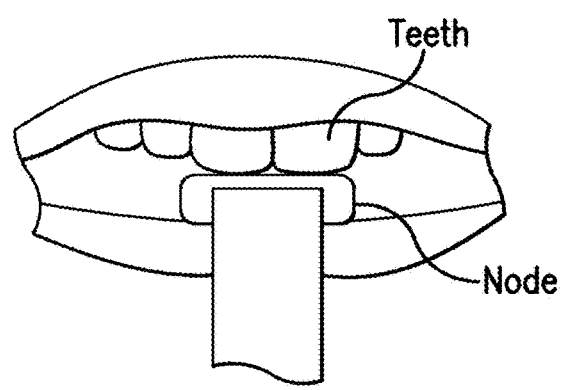

Device 1500 includes a head 1510 having a node 1512 at which one or more sensors (not shown) may be disposed. Sensors may optionally be placed at or near node 1512 to indicate successful pronunciation of the English /f/ or /v/. Such pronunciation is evidenced by the critical zone of contact between the teeth and the lips as shown in FIG. 18*a*. Device 1500 may have an optional tooth stop incorporated therewith.

The B or P Sound

Figure 19:
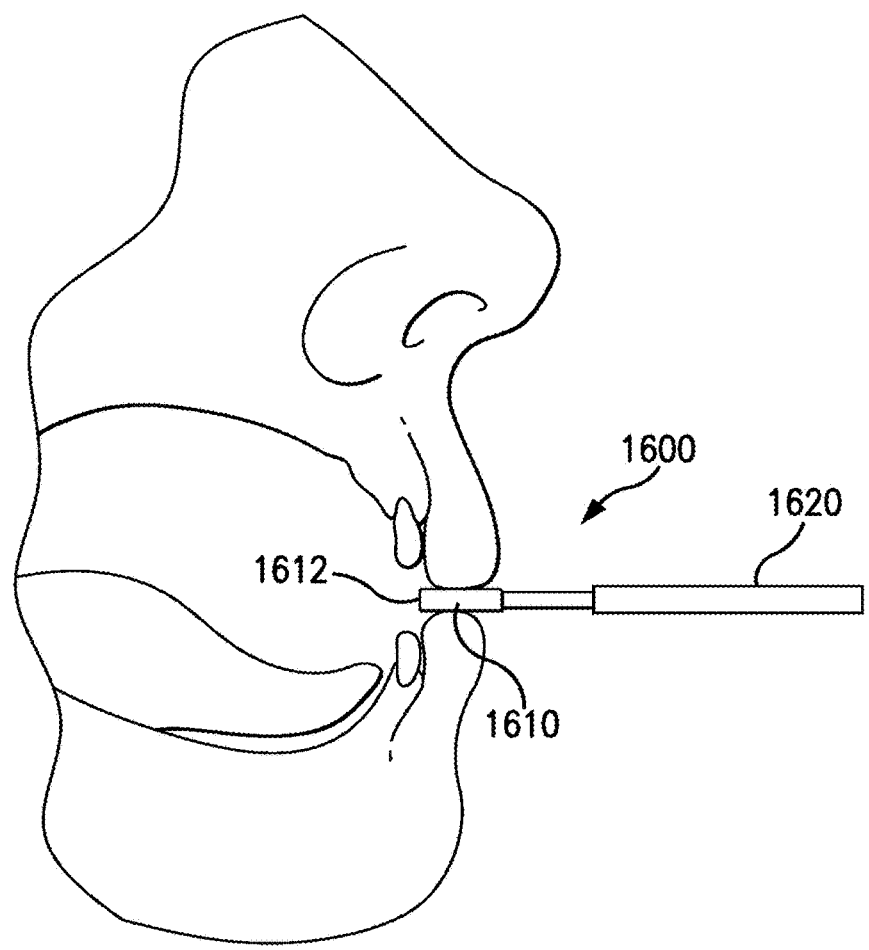
FIGS. 19 and 19A show an exemplary device in use for training the English /b/ or /p/ sound.

FIG. 19 shows an exemplary device 1600 used in an exemplary method for training the English /b/ or /p/ sound. These sounds may also be challenging for Chinese, Japanese, and Korean speakers who are learning to speak English. Device 1600 is shown with the lip position to pronounce the English /b/ or /p/ sound.

Figure 19A:
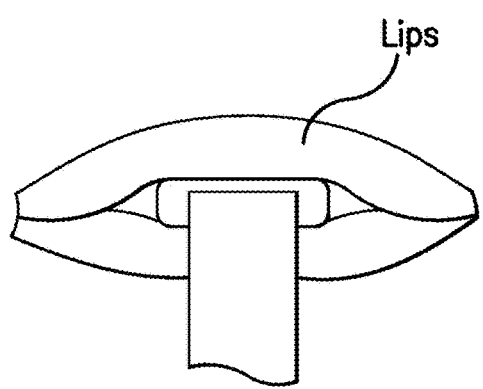

Device 1600 includes a head 1610 having a node 1612 at which one or more sensors (not shown) may be disposed. Sensors may optionally be placed at or near node 1612 to indicate successful pronunciation of the English /b/ or /p/. Such tactile cuing can aid with the production of these sounds, as evidenced by the critical zone of contact between the speaker's lips shown in FIG. 19*a*. Device 1600 may have an optional tooth stop incorporated therewith.

The TH Sound

Figure 20:
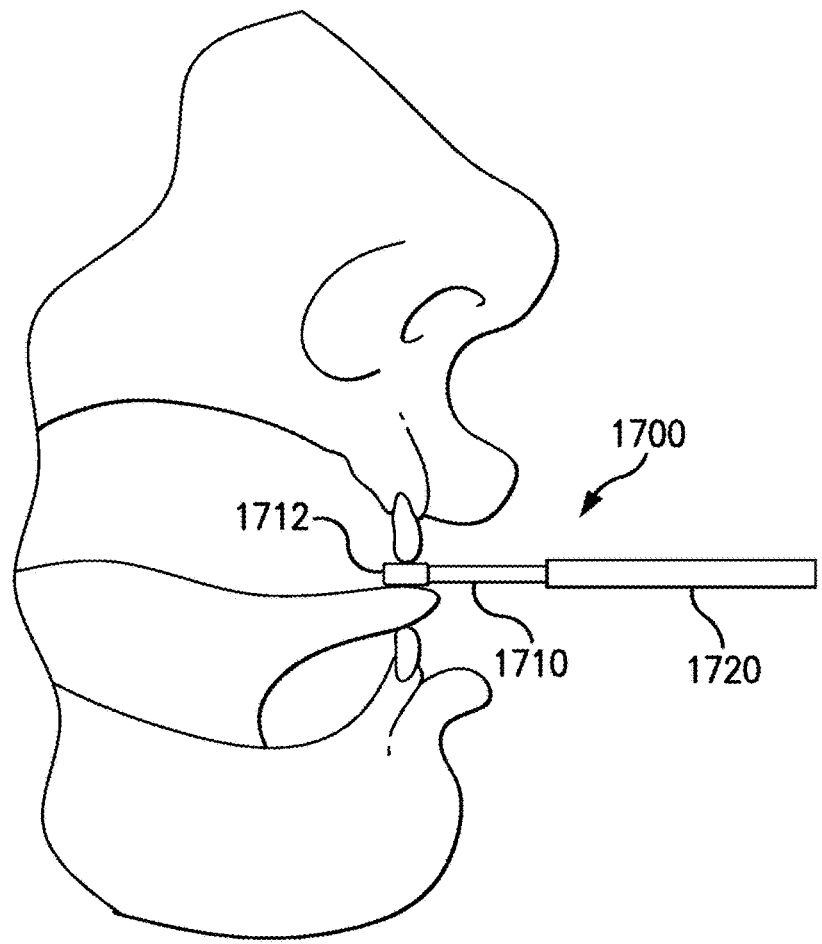
FIGS. 20 and 20A show an exemplary device in use for training the English /th/ sound.
Figure 20A:
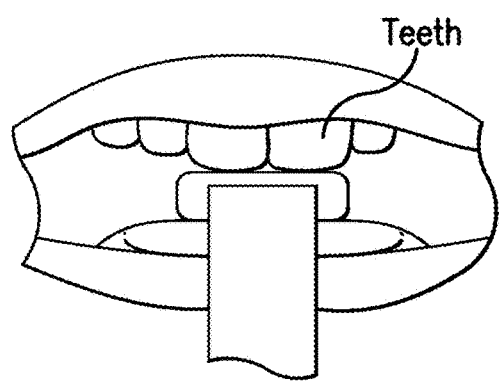

FIG. 20 shows an exemplary device 1700 used in an exemplary method for training the English /th/ sound. This is another sound that may be challenging for Chinese, Japanese, and Korean speakers who are learning to speak English. Device 1700 is shown with the tongue and teeth position to pronounce the English /th/ sound.

Device 1700 includes a head 1710 having a node 1712 at which one or more sensors (not shown) may be disposed. Sensors may optionally be placed at or near node 1712 to indicate successful pronunciation of the English /th/. Such tactile and/or sensory cuing can aid with the production of this sound, as evidenced by the critical zone of contact of the teeth with the tongue shown in FIG. 19*a*. Device 1700 may have an optional tooth stop incorporated therewith.

K and G Sound—a Flexible Embodiment for Different Sized Oral Anatomy

Figure 21:
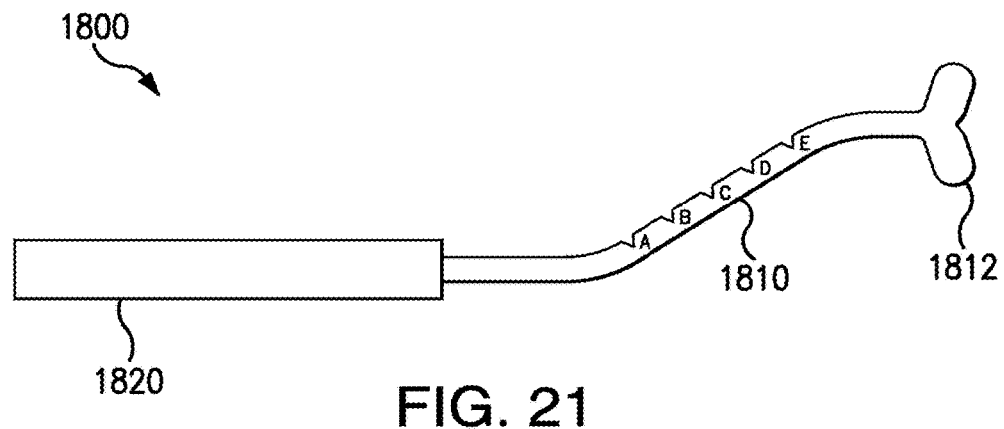
FIG. 21 shows an exemplary device for training the /k/ and /g/ sounds.

Mouth sizes vary dramatically and the distance from the upper dentition to the point in the mouth where the tongue and palate make contact can vary dramatically from patient to patient. FIG. 21 therefore shows an exemplary device 1800 used in an exemplary method for registering the location of the point of contact required for the /k/ and /g/ sounds. Only a single device is needed to train the production of these sounds on various mouth sizes.

Device 1800 includes a head 1810 having a node 1812 at which one or more sensors (not shown) may be disposed and a handle 1820. One or more notches (shown in FIG. 21 as exemplary notches A, B, C, D and E) may be provided intermediate handle 1820 and node 1812 to enable the positioning of node 1812 at various depths within the speaker's mouth. Sensors may optionally be placed at or near node 1812 to indicate successful contact of the node with the palate. Sensors may also be placed in one or more notches to indicate a proper fit of the device in the speaker's oral cavity. Sensors provided at the node and the notches may collaboratively indicate a relative positioning therebetween and thereby aid with the production of the /k/ and /g/ sounds.

Figure 21A:
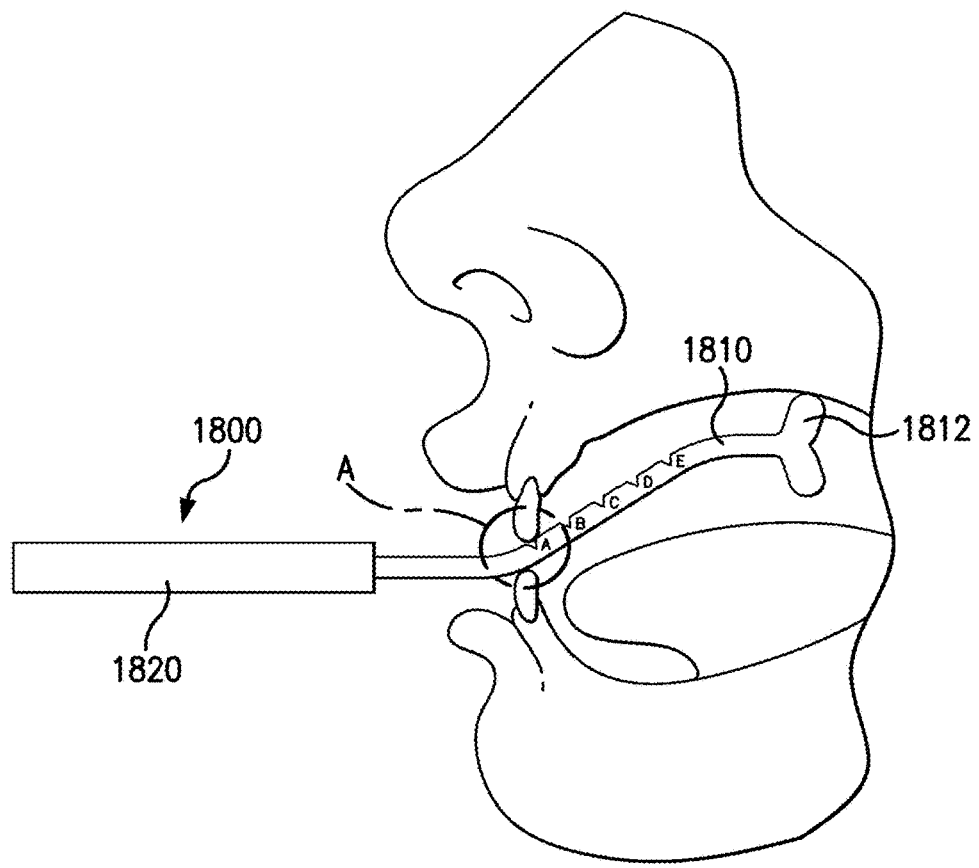
FIG. 21A shows the device of FIG. 21 in use for training the /k/ and /g/ sounds.

As an example of use of exemplary device 1800, FIG. 21A shows a notch A in registry with a speaker's tooth where the speaker is an adult. If the speaker is an adolescent, device 1800 may be inserted into the speaker's mouth so that notch C is in registry with the speaker's tooth. If the speaker is a young child, device may be inserted into the speaker's mouth so that notch E is in registry with the speaker's tooth. It is understood that the notches shown herein are by way of illustration, and that such notches may be replaced by other recesses differing in number and geometry. Alternatively, one or more protrusions may be used in place of or in combination with one or more recesses. The protrusions and/or recesses may be labeled with visual and/or tactile indicia showing recommended use of the device within recommended age ranges and mouth sizes.

Other Sounds

Additionally, the intra-oral tactile feedback devices and methods described herein may also be applied to non-English language speech sounds that are materially similar in place or manner of articulation. Other languages may include, but are not limited to, Chinese, Spanish, Hindi/Urdu, Arabic, Portuguese, Russian, Japanese, German, and French.

For example, the methods and devices described herein in connection with the English /t/ and /d/ sounds (alveolar stop consonants) may be used in connection with similar speech sounds in Chinese, Spanish, Hindi/Urdu, Arabic, Portuguese, Russian, Japanese, German and French.

The methods and devices described herein in connection with the English /l/ sound (an alveolar liquid consonant) may be used in connection with similar speech sounds in Chinese, Spanish, Hindi, Arabic, Portuguese, Russian, German, and French, but not Japanese.

The methods and devices described herein in connection with the English /τΣ/ (ch) and /δZ/ (j) sounds (alveolar affricate consonants), may be used in connection with similar speech sounds in Chinese, Spanish (not /δZ/), Hindi/Urdu, Russian (not /δZ/), and German (not /δZ/), but not Arabic, Portuguese, or French.

The methods and devices described herein in connection with the English /s/ and /z/ sounds (alveolar sibilant fricative consonants) may be used in connection with similar speech sounds in Chinese (not /z/), Spanish, Hindi/Urdu, Arabic, Portuguese, Russian, Japanese, German, and French.

The methods and devices described herein in connection with the English /Σ/ (sh) and /Z/ (zh) sounds (post-alveolar sibilant fricative consonants) may be used in connection with similar speech sounds in Hindi/Urdu, Portuguese, Russian, German, and French, but not Chinese (correlate articulated more posteriorly), Spanish, Arabic, or Japanese.

The methods and devices described herein in connection with the English /g/ and /k/ sounds (velar stop consonants) may be used in connection with similar speech sounds in Chinese (not /g/), Spanish, Hindi/Urdu, Arabic (not /g/), Portuguese, Russian, Japanese, German, and French. In addition, though not present in English, German contains the velar fricative /x/. Intra-oral tactile biofeedback targeting the velar stop consonants /k/ and /g/ may also be applied to the velar fricative consonant /x/.

The methods and devices described herein in connection with the English /y/ and /j/ sounds (a palatal glide) may be used in connection with similar speech sounds in Chinese, Spanish, Hindi/Urdu, Arabic, Portuguese, Russian, Japanese, German, and French.

The methods and devices described herein in connection with the English /r/ sound (a retroflexed and/or retracted rhotic) may be used in connection with similar speech sounds in Chinese and Hindi/Urdu, but not Spanish, Arabic, Portuguese, Russian, Japanese, German, or French.

Intra Oral Tactile Feedback Combined with Lip Manipulation and Positioning

Figure 22:
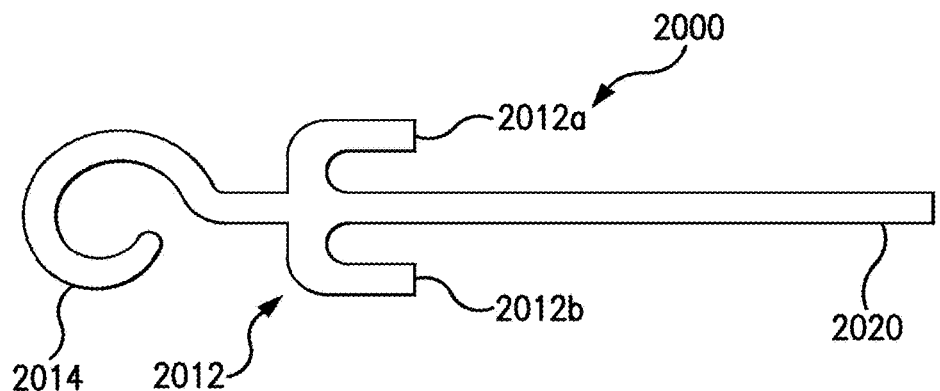
FIG. 22 shows an exemplary device for training the /r/ sound by proper orientation of the speaker's tongue and lips.

The devices and method described herein may also incorporate one or more methods of intra-oral tactile biofeedback to stimulate a specific phoneme, not only to train correct tongue placement but also to reinforce proper lip configuration. FIG. 22 shows an exemplary device 2000 used in an exemplary method for training the /r/ sound, wherein both the tongue and the lips are oriented correctly. Device 2000 may comprise an integral member or detachably engaged members including a head 2010 and a handle 2020. Handle 2020 may house an onboard computer and/or may include structure for engagement with a computing device, as described above.

Figure 22A:
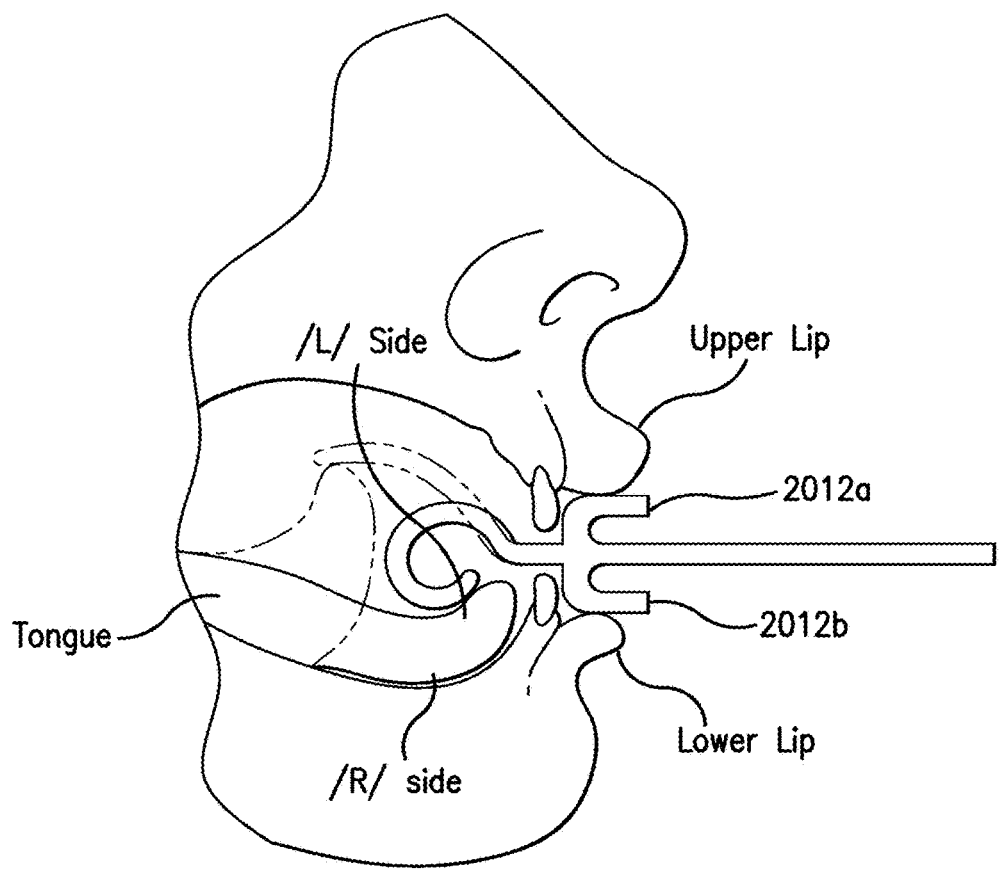
FIG. 22A shows the exemplary device of FIG. 22 in use for training the /r/ sound.

Head 2010 includes a node 2012 at or near which one or more sensors (not shown) may be disposed. Node 2012 is shown herein as a generally arcuate member having an upper arch 2012*a* for contact with a speaker's upper lip and lower arch 2012*b* for contact with a speaker's lower lip when device 2000 is inserted into a speaker's oral cavity. In the case of the /r/ sound, rounding of the lips can be cued as shown in FIG. 22A. It is understood that node 2012 may assume other geometries and features amenable for successful practice of this exemplary embodiment. Such geometries may be amenable to ensuring proper lip position during production of other sounds.

Head 2010 further includes a coil 2014 that is unwound when a correct pronunciation is made, but does not unwind when an incorrect pronunciation is made. Sensors may optionally be placed at or near node 2012 and/or coil 2014 to indicate successful pronunciation of the /r/. Additional sensors may be placed at or along upper arch 2012*a* and/or lower arch 2012*b* to indicate proper lip positioning prior to, and during, sound production.

Figure 23:
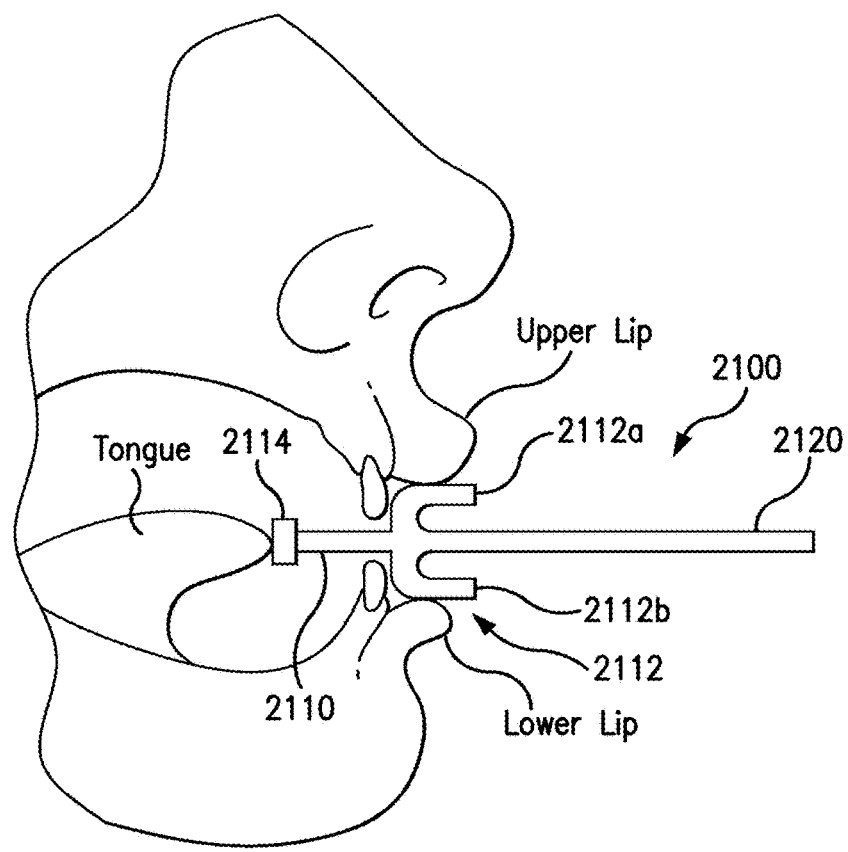
FIG. 23 shows an exemplary device in use for training the /sh/ sound by proper orientation of the speaker's tongue and lips.

Another exemplary device 2100 may be provided as shown in FIG. 23 for use in an exemplary method for training the /sh/ sound by training and reinforcing both tongue and lip positioning. Device 2100 may comprise an integral member or detachably engaged members including a head 2110 and a handle 2120. Handle 2120 may house an onboard computer and/or may include structure for engagement with a computing device, as described above.

Head 2110 includes a node 2112 at or near which one or more sensors (not shown) may be disposed. Node 2112 is shown herein as generally an arcuate member having an upper arch 2112*a* for contact with a speaker's upper lip and lower arch 2112*b* for contact with a speaker's lower lip when device 2100 is inserted into a speaker's oral cavity. In the case of the /sh/ sound, curvature of the upper and lower lips into a "fish face" encourages correct pronunciation and can therefore be cued by device 2100 as shown. It is understood that node 2112 may assume other geometries and features amenable for successful practice of this exemplary embodiment. Such geometries may be amenable to ensuring proper lip position during production of other sounds.

Head 2110 further includes a tongue stop 2114 that provides a target for guidance of the speaker's tongue before and during sound production. Sensors may optionally be placed at or near node 2112 and/or tongue stop 1014 to indicate successful pronunciation of the /sh/. Additional sensors may be placed at or along upper arch 2112a and/or lower arch 2112b to indicate proper lip positioning prior to, and during, sound production.

Figure 24:
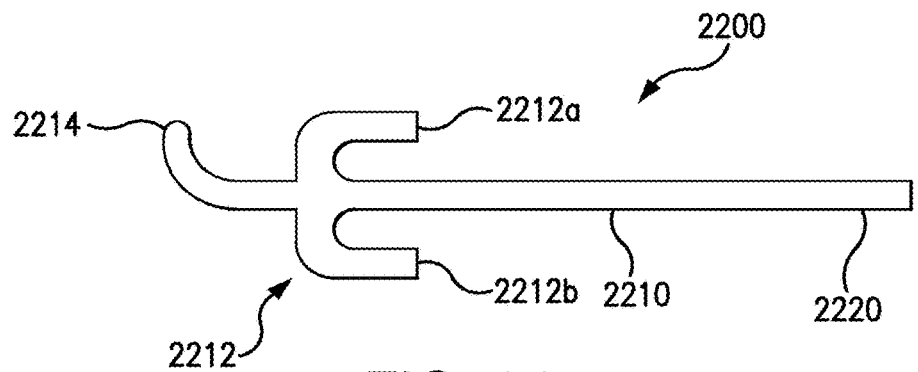
FIG. 24 shows an exemplary device for training the /l/ sound by proper orientation of the speaker's tongue and lips.

Another exemplary device 2200 may be provided as shown in FIG. 24 for use in an exemplary method for training the /l/ sound by training and reinforcing both tongue and lip positioning. Device 2200 may comprise an integral member or detachably engaged members including a head 2210 and a handle 2220. Handle 2220 may house an onboard computer and/or may include structure for engagement with a computing device, as described above.

Figure 24A:
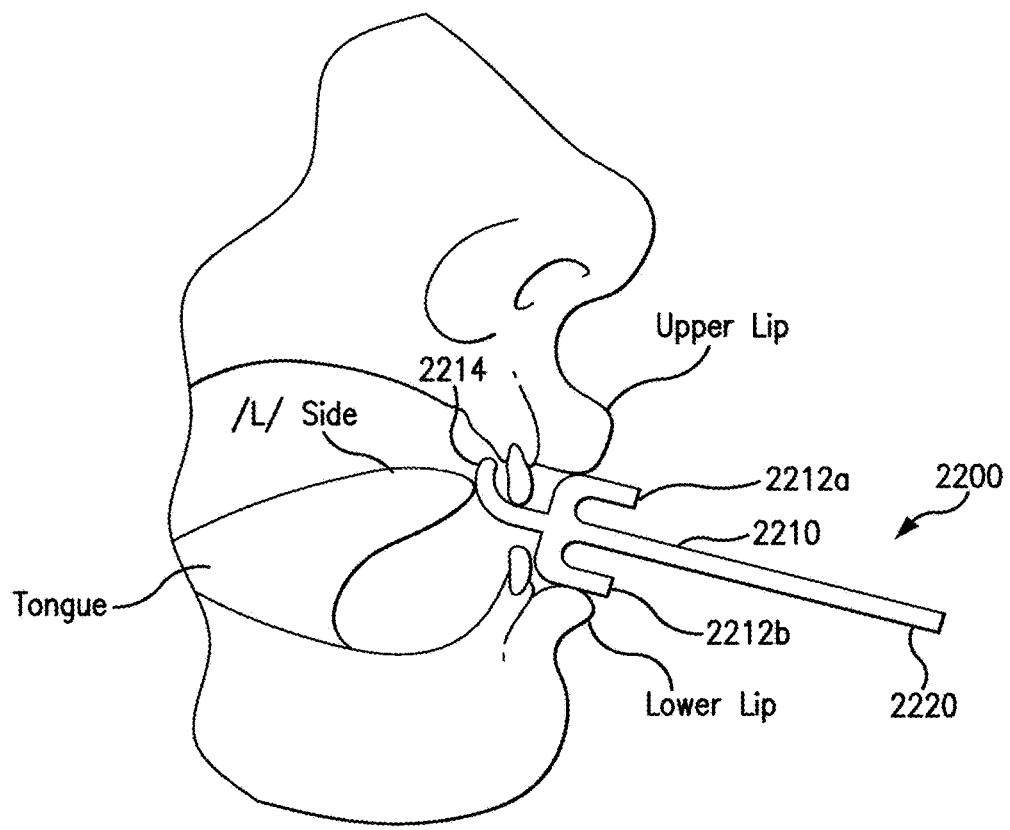
FIG. 24A shows the exemplary device of FIG. 24 in use for training the /l/ sound.

Head 2210 includes a node 2212 at or near which one or more sensors (not shown) may be disposed. Node 2212 is shown herein as generally an arcuate member having an upper arch 2212a and lower arch 2212b for respective contact with a speaker's upper and lower lips when device 2200 is inserted into a speaker's oral cavity. In the case of the /l/ sound, the upper lip needs to be raised upward as cued by device 2200 as shown in FIG. 24a. It is understood that node 2212 may assume other geometries and features amenable for successful practice of this exemplary embodiment. Such geometries may be amenable to ensuring proper lip position during production of other sounds.

Head 2210 further includes a tongue stop 2214 that provides a target for guidance of the L side of the speaker's tongue. Sensors may optionally be placed at or near node 2212 and/or tongue stop 2214 to indicate successful pronunciation of the /l/ sound. Additional sensors may be placed at or along upper arch 2212a and/or lower arch 2212b to indicate proper lip positioning prior to, and during, sound production.

It is understood that specific embodiments of nodes 2012, 2112 and 2212 may be adapted to enable phoneme-specific articulatory facilitation (for example, to cue other tongue and lip postures to train and reinforce other sounds, including but not limited to the /ch/ sound, the /f/ and /v/ sounds and the /k/ and /g/ sounds). Such nodes may be adapted to train tongue position, movement, and shape corresponding to proper production of a specific speech sound. Further, such nodes demonstrate both static and dynamic tongue movements, thereby enabling arrangement of the nodes to provide successive tactile and sensory cues to help achieve one or more desired tongue movements.

Synthesis of Intra Oral Tactile Biofeedback Sensor Input for Accuracy Determination and Error Synthesis As a simple example using an exemplary device for the L-phoneme (such as exemplary device 600 shown and described herein), the word "Girl" is pronounced incorrectly as "Girw". The speaker's tongue would contact at least one sensor 605 when the word was pronounced "Girl" (see, for example, FIG. 5 for device 600 in use). Neither sensor 605 would be contacted by the speaker's tongue when the word was pronounced "Girw". A binary output of sensor contact "Y/N", for example, could be translated directly to user interface software.

False positives and negatives can be detected by matching specific patterns with spoken words when compared to those that are served on the software platform. For example, when saying the /n/ sound, if the L-phoneme device is in the mouth, the sensor may detect the "N" as an "L". For a word like "Lion", there may be two detections: one detection for "L" at the beginning of the word and one detection for "N" at the end of the word. In the event that a speaker pronounces "Lion" correctly, software applications can be implemented to interpret two contacts by the speaker's tongue as a correct pronunciation, with the first being the "L" and the second being the "N".

Audio Duration Input to Aid in Determination of Correct and Incorrect Sound

Another method of using sensors to determine a correct an incorrect pronunciation is the introduction of a microphone to aid in error recognition. The microphone could be an onboard microphone from tablet, smartphone, or laptop computer or an offboard microphone. A microphone and subsequent audio input is synchronized with the sensor so that a computer can match the duration of the audio input of a word with the intra-oral tactile bio-biofeedback from the sensor. In essence, it can determine if the detection came at the right time within the word or not. As an example, if a subject pronounces the word as "Wion" instead of "Lion", they did not pronounce the L correctly, but it is possible that the sensor would detect the pronunciation of "N" at the end of "lion".

Suppose the word "lion" was served as the next word in a practice exercise. If it is known that "Lion" takes between 0.5 and 1.2 seconds to pronounce, the software first can verify that the correct word was being pronounced. Next, if it was a 1.0 second audio sample, we can determine that the first 25% (in this case 0.25 seconds) of the audio sample was used to pronounce the "L" sound, the next 25% to pronounce the "I" sound, the next 25% to pronounce the "O" sound, and the final 25% the "N" sound. If the only detection that came from the sensor inside the mouth occurred from second 0.750 to 1.000, it is safe to assume that the "N" sound was pronounced correctly, but not the "L" sound, and thus that the pronunciation for "lion" was "wion" and therefore incorrect (see Table 1 below).

TABLE 1

| Sample of "LION" pronounced incorrectly as "WION": | | | | |
| --- | --- | --- | --- | --- |
| Time (ms) | 250 | 500 | 750 | 1000 |
| Sound | L | I | O | N |
| Sensor Binary Output | No | No | No | Yes |

Figure 25:
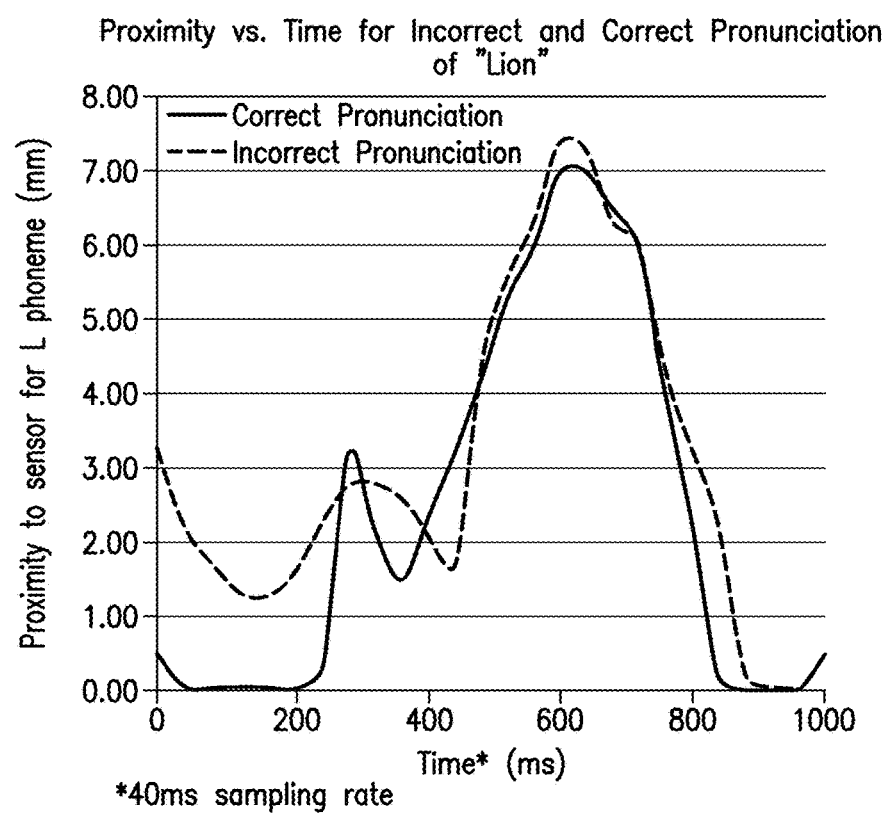
FIG. 25 shows an exemplary representation of the proximity of a speaker's tongue to a sensor on an exemplary L-phoneme device during pronunciation of the word "lion".

Proximity Profile Used to Aid in the Determination of a Correct Vs. Incorrect Sound or Word Another method of error or accuracy detection involves building a database of profiles of different intra oral tactile biofeedback sensor outputs that can be generated for specific words. Continuing to use the example of Lion, FIG. 25 shows the graph of the proximity to the sensor on the L-phoneme device during the pronunciation of the word "Lion". The two graphs show the difference between a correct and an incorrect pronunciation based on the tongue tip's proximity to the sensor. The incorrect pronunciation in this case was "Wion" instead of "Lion".

A database of profiles for correct and incorrect sound and word pronunciation can measure the proximity of the tip of the tongue to the intra-oral-tactile-biofeedback sensor for the various phonemes. This database can then be compared to the current sample that is being pronounced which can aid in the determination of a correct and an incorrect pronunciation.

Proximity Profile Used to Aid in Speaking and Communication

The proximity profile of an intra-oral-tactile biofeedback device with an onboard sensor can be used as a method to interpret speech simply through the movement of the tongue, but without the involvement of the vocal cords.

A person that is non-verbal may not be able to enunciate sounds, but may still be able to produce correct tongue and lip movements required for speech. By using an intra-oral tactile bio-feedback device with a proximity sensor on the node, a string of words and sentences can be interpreted through a computer. This string of sentences can then be communicated either through written text, or turned into speech through the use of text-to-speech converter. This technology could also be useful for other operations which require communication to occur in complete silence and potentially darkness, including but not limited to military and tactical applications, bird watching, surveillance, etc.

Software Applications and Diagnostic Teaching Methods

Online Exercises for Articulation Practice

Utilizing articulation exercises augments the success realized during the process of speech therapy and language learning. For example, different combinations of sounds and words may be repeated with the placement of "trouble" sounds within a word. Providing corresponding feedback to the speaker upon utterance of correct and incorrect sound pronunciation is an important feature of the learning process. Computer-based software programs operable with computing devices can be helpful in supporting this function.

In accordance with a further aspect of the presently disclosed invention, the sensors provided on the device nodes interface with a computing device that may include software for monitoring tongue contact with a respective node. A "computing device", which may be an electronic or computer-based apparatus, may include, but is not limited to, online, desktop, mobile and handheld devices and equivalents and combinations thereof.

Integrating multi-sensory information or cues during speech therapy and language learning may enhance the overall learning experience. Thus, software applications incorporated with such computing devices may also provide, among other things, real-time on-screen visualization of lingual contacts with the disclosed nodes (including those nodes disclosed herein and also those nodes disclosed in co-owned U.S. Pat. No. 8,740,622), graphical representation of auditory sound waves, "game" style positive reinforcement based on progress, data collection and statistical analysis, playback of recorded verbal reproductions as an indication of the status of patient speech productions and comprehensive arrays of pre-recorded model phoneme productions to encourage greater accuracy via imitation. As used herein, software applications may be "incorporated" when they are downloadable to or uploadable from one on more devices, pre-loaded onto one or more devices, distributable among one or more devices or distributable over a network and any complement and equivalent thereof.

With reference to FIGS. 26 to 30, a user can access a software application to initiate an interactive learning module. As used herein, a "user" may be a single user or a group of users and may include speakers, patients, therapists, doctors, teachers, family members and any other person or organization that might take part in advancing a speaker's speaking and language capacity. As used herein, the term "user" (or "user device" or "client device") can refer to any electronic apparatus configured for receiving control input and configured to send commands or data either interactively or automatically to other devices. The user device can be an instance of an online user interface hosted on servers as retrieved by a user. As used herein, the term "process" or "method" may refer to one or more steps performed at least by one electronic or computer-based apparatus.

Figure 26:
FIGS. 26 to 28 show exemplary screenshots of a user interface for a software application in which speakers interact with devices to derive sensor data indicative of pronunciation proficiency.
Figure 27:
Figure 28:
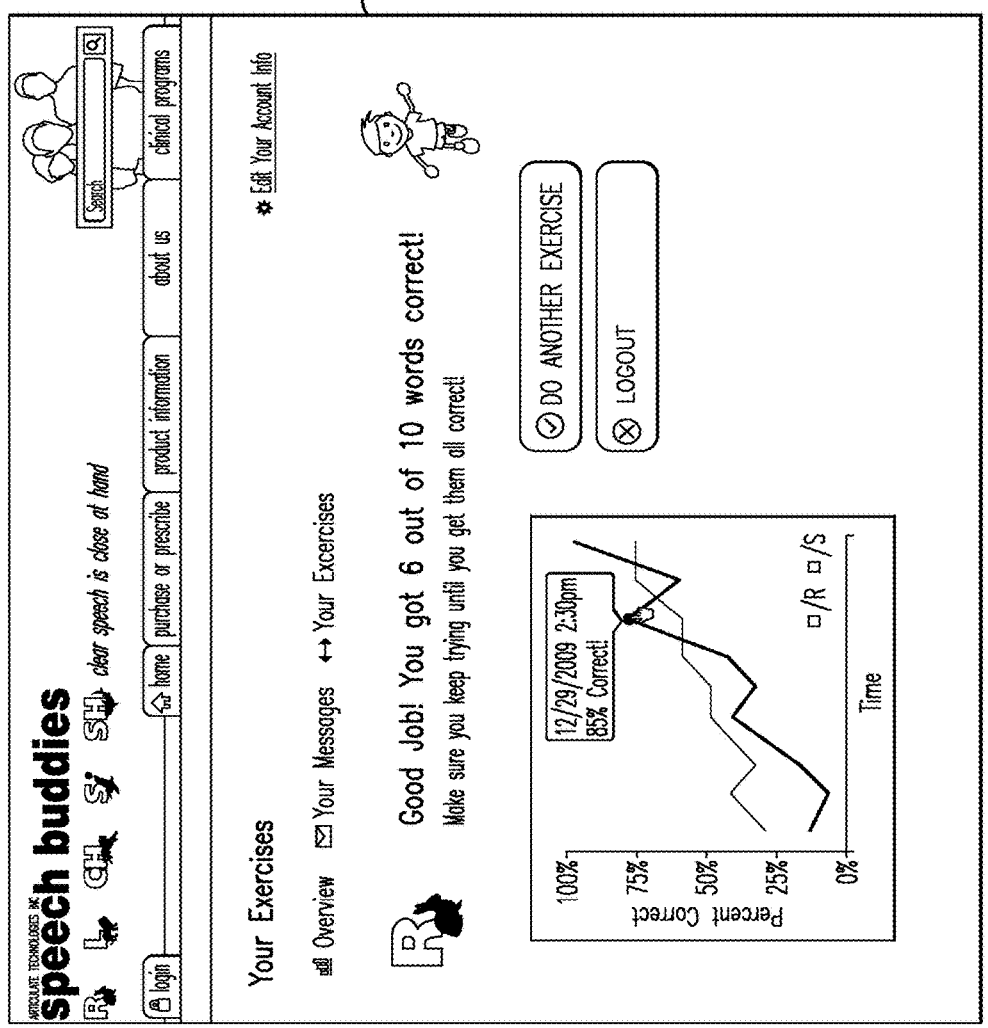

FIG. 26 shows an exemplary screenshot 3000 of a software application in which a word is shown. In this case, the target sound is the /r/ sound, although it is understood that any sound or sounds may comprise the target. FIG. 27 shows an exemplary screenshot 4000 with the target sound being employed in target words in a sentence. In this case, the target words are "rabbits", "carrots", "garden" and "really". During an exercise, the speaker will utter the displayed words and/or sentences with a device inserted in the speaker's oral cavity. After completion of a word sentence, or a battery of words or sentences, the sensors disposed on the device indicate the speaker's accuracy. This accuracy may be represented graphically, and may be represented in real-time or near real-time, as shown in the exemplary screenshot 5000 of FIG. 28. The graphical representation may represent accuracy for an individual exercise or may also represent the speaker's performance in many different types of exercises. One or more buttons may be provided that enable the user to perform additional exercises or to logout of the software application. Although a line graph is shown in FIG. 28, it is understood that any graphical representation may be employed, including but not limited to bar graphs, pie charts and the like.

Audio feedback may replace or complement such graphical representations of accuracy. Speech can be recorded on a computer or mobile device and played back in order to aid in the learning process. A sound bite can be parsed in different segments and played back in sequence or out of order.

Also, a computer of mobile device with an integrated camera may use video recording and/or still shots of a subject to conduct speech therapy or other services. Such photography may be time stamped and analyzed for tongue, lip and/or throat movements during speaking exercises. Data from these additional visual cues may also be included in any graphical representation to assist in diagnoses of ongoing physical or language impediments.

Figure 29:
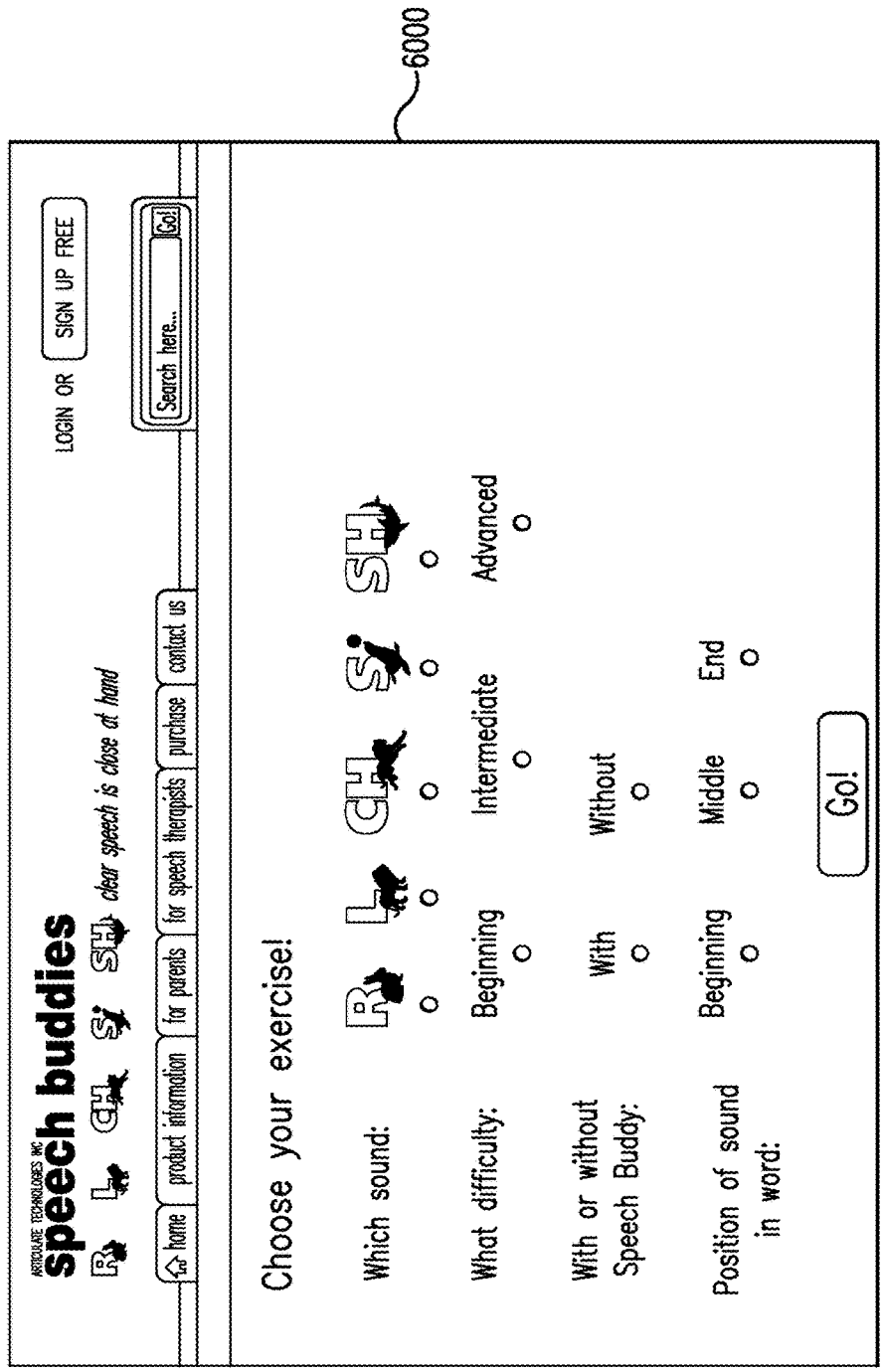
FIG. 29 shows an exemplary screenshot of a user interface for a software application that enables the user to customize one or more speaking exercises.

FIG. 29 shows an exemplary screenshot 6000 in which a software application enables the user to customize one or more exercises. In the example shown in FIG. 29, the user may select from a variety of exercise options. For instance, different types of words can be selected for articulation practice, and those words may include target sounds in different word positrons. Also, the exercises may be performed with or without the intraoral tactile biofeedback devices in the speaker's mouth. Other options may be available that are contemplated herein, including but not limited to multiple choice exercises and visual and audio cues. As an example of the latter, a picture of a bird may be shown without the word "bird", or a bird call may be played. The speaker can be prompted to say the word "bird" in response to display of the bird picture or transmission of the bird call. This type of exercise customization may be particularly helpful in not only improving speech and language abilities but also in reinforcing mental associations among words, images and/or sounds (for instance, with patients recovering from brain trauma).

Figure 30:
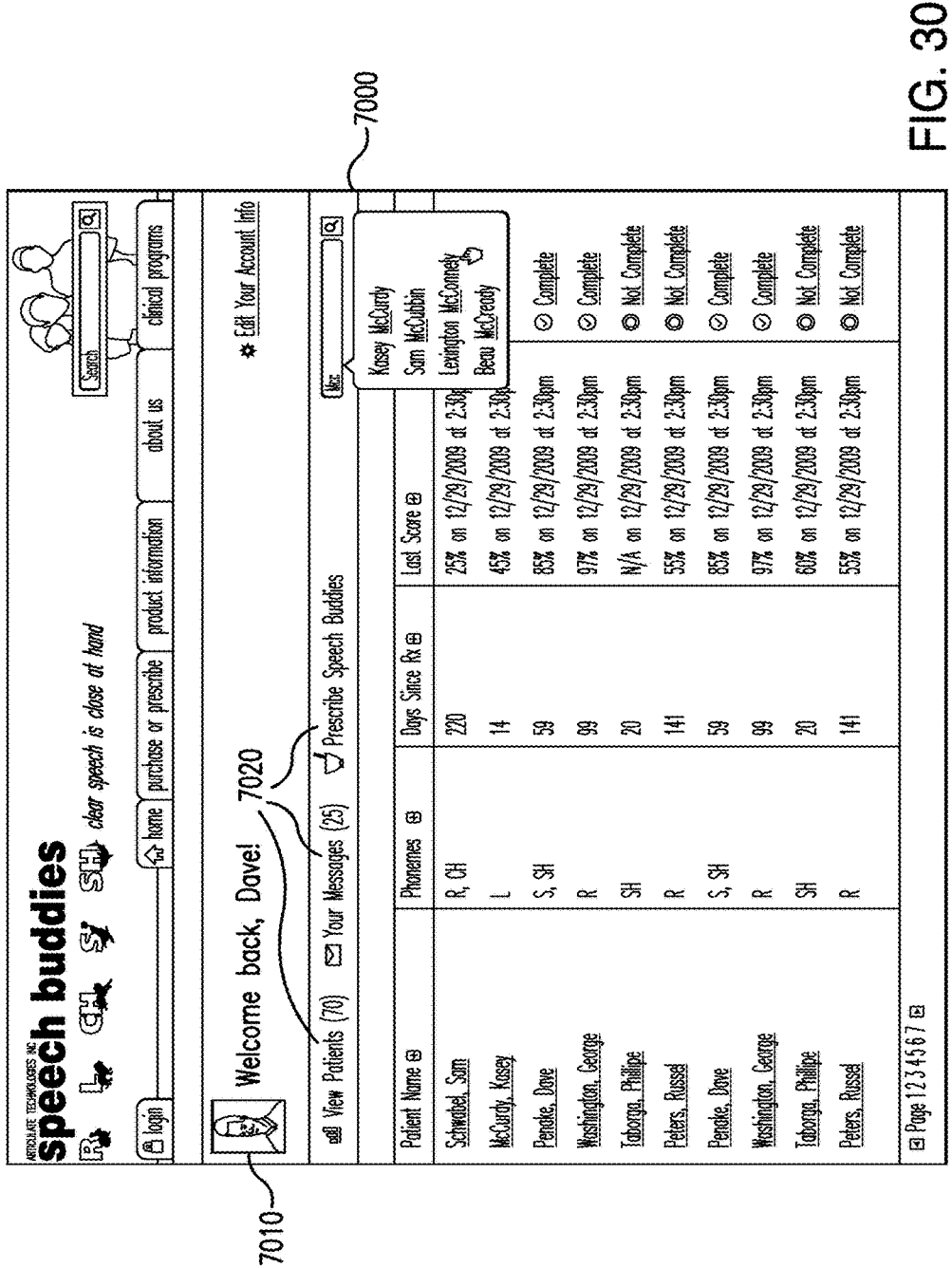
FIG. 30 shows an exemplary screenshot of an exemplary practitioner dashboard.

FIG. 30 shows an exemplary practitioner dashboard 700 in which a language teacher, speech therapist or parent (the exemplary "practitioner" 7010) can monitor the accuracy and results of practice of a number of students/patients/children simultaneously. Practitioner dashboard 7000 may include one or more buttons 7020 that facilitate the practitioner's interaction with multiple speakers. As shown here, practitioner 7010 has access to a list of patients and each patient's progress in learning particular sounds (although such displayed information is not limited to what is shown and other information may be displayed and/or accessible via one or more links or buttons). Each practitioner user may modify his/her dashboard profile to allow others to view the practitioner's profile and may further modify the extent to which certain categories of other practitioners can view the profile. The practitioner may not allow other practitioners to view his/her profile at all, or may only allow limited access to the profile in certain situations (for instance, if the practitioner is working on a team of multidisciplinary practitioners and caregivers when working with a particular patient). The dashboard may also include other functions such as a calendar function in which a calendar shows the practitioner's scheduled appointments and treatment sessions. The practitioner may be able to follow a designated entity (e.g., a particular speaker, etc.) and elect to receive notifications of any update to the entity status, thereby ensuring that practitioners and speakers have the most up-to-date data.

Social Networking for Practitioners and Speakers

A user (including any speaker, practitioner or family member) can also initiate a social networking method for building an online presence in a collaborative social networking system, which may be a site or website. The method of having a social network specifically designed around the relationship between practitioners and speakers includes unique architecture. Such architecture can promote the flow of information and recommendations from practitioners to speakers, as well as between practitioners and speakers. For instance, healthcare providers can give blanket recommendations simultaneously to many patients who would benefit from the same information. Patients can discuss and synthesize the recommendation that they may have received from the same doctor, and perhaps obtain second and third opinions if desired. Also, speech therapists or physical therapists can prescribe specific sets of exercise to multiple patients at once to practice that day. The same architecture applies for the relationships among teachers and students, in that homework and lessons can be communicated in this format. Specific safeguards could be used in the event that non-identifying patient/student information needs to be used to communicate sensitive information.

There are several forms in which this architecture can take shape. The simplest architecture is where a practitioner has a relationship with the practitioner's own patients or clients. In another instance, the practitioner can communicate with other practitioners as well as their own patients. In yet another instance, the practitioners can communicate with not only their patients, and other practitioners, but also other patients. These "other" patients may or may not be affiliated with other practitioners.

Figure 31:
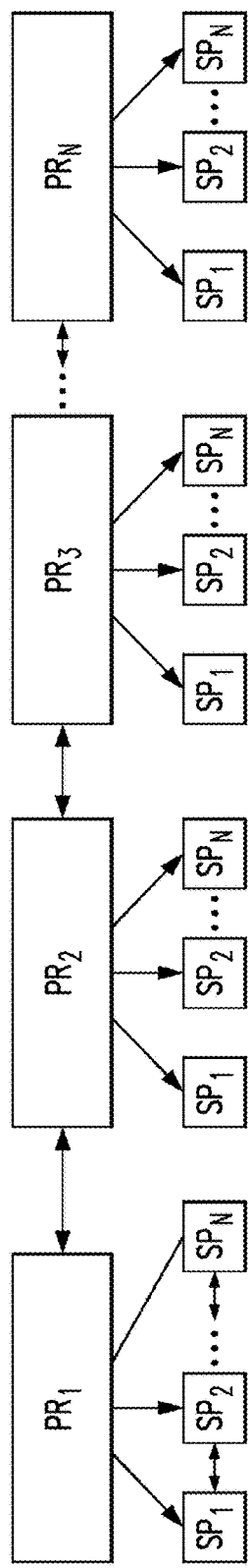
FIG. 31 shows an exemplary social network supported by a platform that enables intercommunication among multiple practitioners and multiple speakers.
Figure 32:
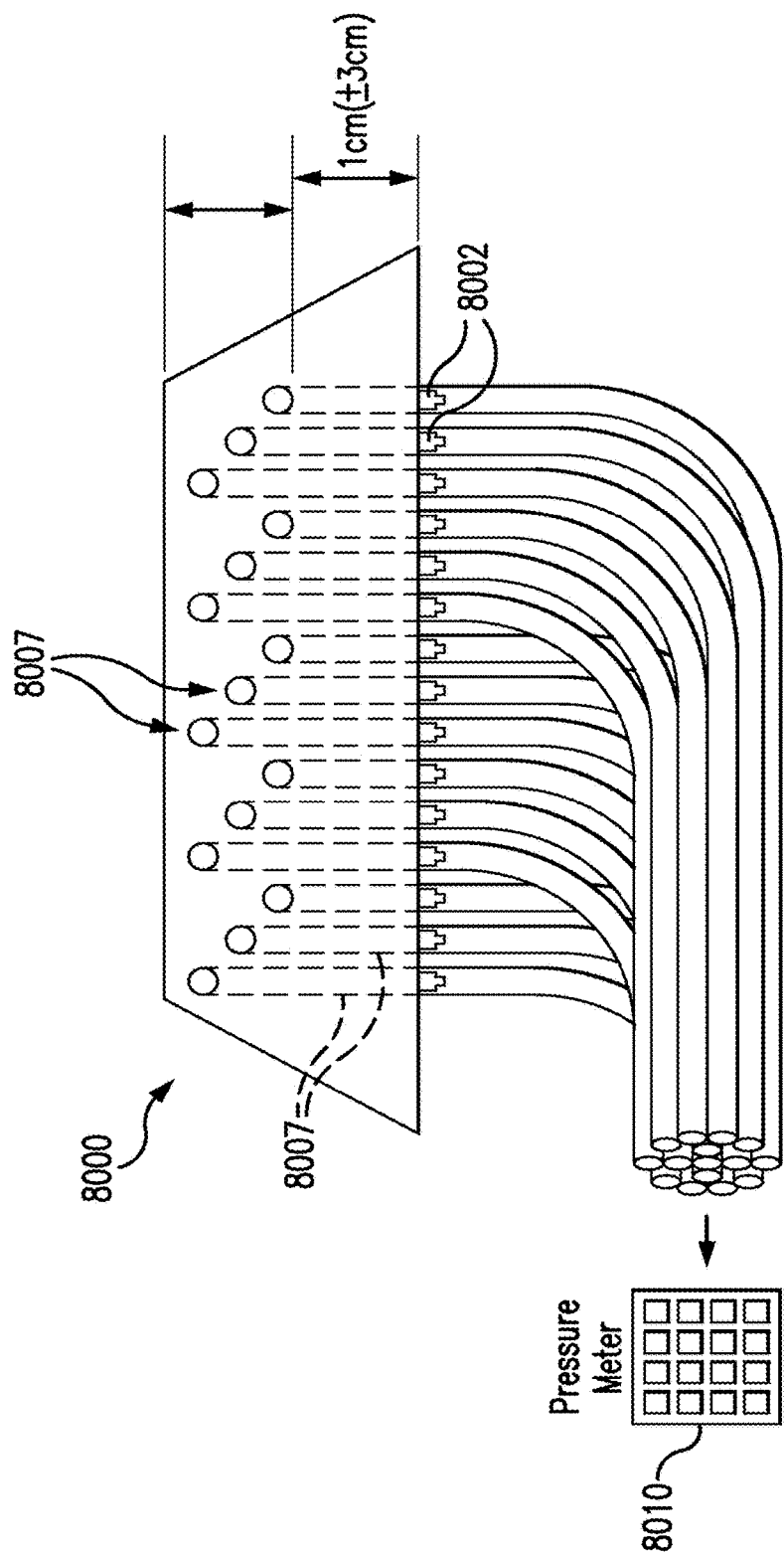
FIGS. 32-33 show an exemplary device for measuring pressure to determine breast feeding quality.
Figure 33:
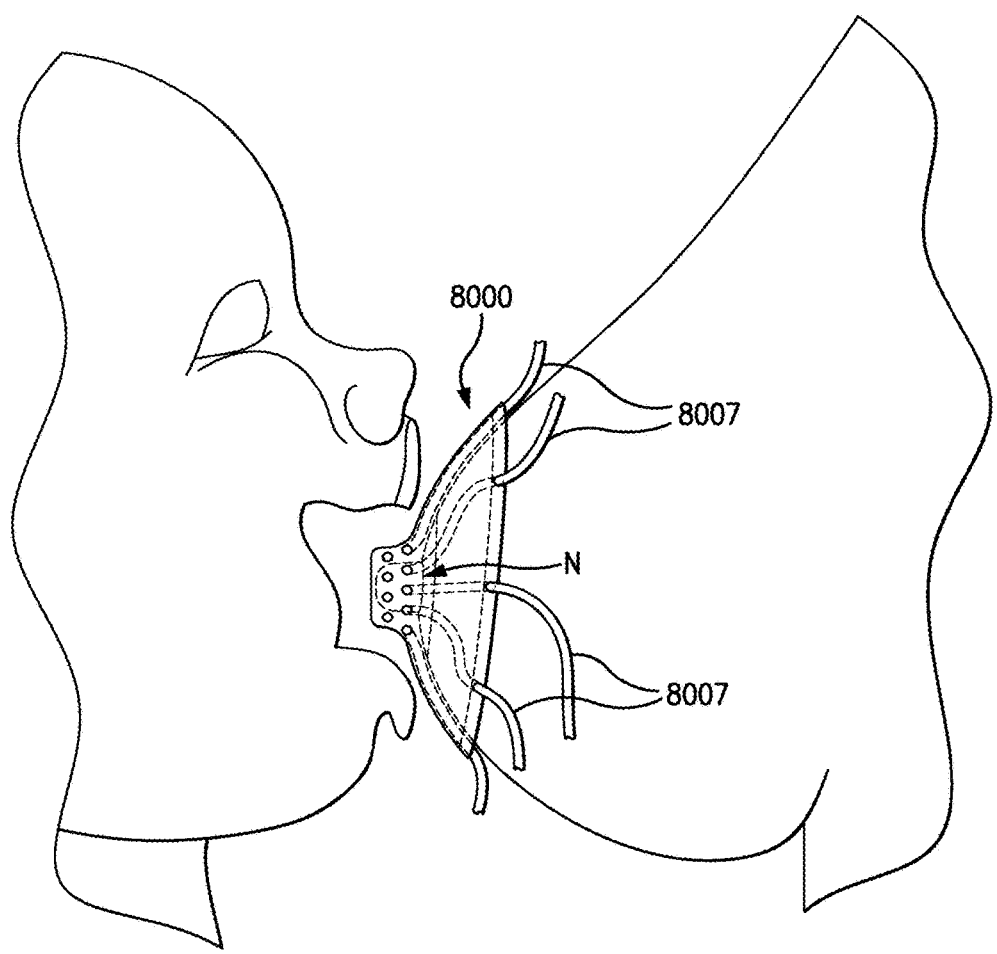

FIG. 31 shows an exemplary social network where practitioners $PR_1$ to $PR_N$ (such as healthcare providers, therapists, teachers, family members and caregivers) can communicate with their own speakers $SP_1$ to $SP_N$. In this example, the practitioners can also communicate with one another and/or with other speakers. For example, $PR_1$ may ask $PR_3$ for a consult with respect to one of speakers that $PR_1$ treats or teaches. In another example, PR1 to $PR_{N\,may}$ be parents of speakers who desire collaboration with one another not only in performing and assessing exercises but also in providing an elective support network.

A user may access a collaborative social networking system via a log-in that may be immediately presented or may be accessible from another web page or from a mobile application. New users can create, and registered users can modify, a preference profile that can include attributes such as age, gender, skill set, current training and learning goals, although the collaborative social networking system is not limited to these attributes. Also, new users may able to create, and registered users to modify, an avatar that will virtually represent the user on the collaborative social networking system. Such an application might be desirable in multi-user virtual environments ("MUVEs"), including 3-D virtual environments, that allow users to assume a virtual identity and interact through that identity with other users who have also assumed virtual identities. Users can indicate, and registered users can modify, the users' willingness to receive invitations to speaking sessions and invitations to join exercise teams (for example, wherein teams compete in speaking exercises and compare scores to encourage learning by competition). The collaborative social networking system may also support an application for users to acquire "points" or "credits" for participation in exercises. Accumulation of "credits" can encourage speakers to practice more often and at higher difficulty levels.

In order to treat or train various classes of consonant sounds in accordance with the methods and devices described herein, a therapist must be able to cue various tongue positions during the production of speech sound. To be able to cue the various tongue positions for the proper production of different speech sounds, a therapist may need to employ various node configurations to provide the proper tactile feedback. Thus, in accordance with another aspect of the invention, provided is a kit containing one or more devices for providing the proper tactile feedback for the production of a plurality of speech sounds.

General Speech Diagnostic Test

The methods, devices and systems described herein may be used in connection with one or more generalized diagnostic tests (GDT) that can help determine the type of speaking disorder exhibited by a speaker. Diagnoses are typically performed by a Speech Language Pathologist (SLP) over the course of a lengthy question and answer process. Through a simple, shorter diagnostic questionnaire, it is possible to determine with quite some accuracy the specific diagnosis for an individual. This GDT can be completed by the speaker or by a caregiver (such as a parent) without the oversight of an expert. It can be administered in electronic and digital formats over wireless networks such as the internet, on mobile devices or in hard copy.

EXAMPLE

Sample inputs to the GDT can be the following:

Sample Inputs

1. What age is your child?
    a. Slider bar 1-18
2. What sex is your child?
    a. Male
    b. Female
3. What stage in speaking is your child
    a. Just some sounds
    b. Just some words
    c. Short phrases
    d. Can speak fluently
4. Select which categories you think more accurately describes your child's speaking challenge: (they can select multiple)

| a) Speech Challenge | b) Language Challenge | c) Fluency Challenge |
|---|---|---|
| Description:<br>Trouble making specific sounds, words, or patterns consistently. Frequently omits, substitutes or incorrectly pronounces specific sounds | Description:<br>Difficultly in understanding and or sharing thoughts completely. Grammar, full sentences, and correct verb tenses are challenging. | Description:<br>Has trouble with speech flow of rhythm. Stutters or Clutters words. |
| Examples:<br>Wabbit vs rabbit<br>Thock vs sock<br>Tup vs cup<br>Das vs gas<br>Poon vs spoon | Examples:<br>I goed to the park.<br>I keeped the ball.<br>I breaked toy.<br>Or simply not understanding your speech very well | Examples:<br>"W- w- w- where are you going?"<br>"I'll meet you - um um you know like around six o'clock."<br>"I-think-you . . . need-to-listen-to-me . . . a-little-more-carefully" |
| Audio Sample: | Audio Sample: | Audio Sample: |

5. If 4A Yes—Select which category more accurately describes your child's speaking challenge: (they can select multiple)

| Articulation Challenge | Phonological Challenge |
|---|---|
| Description:<br>Trouble making specific sounds or words consistently. Frequently omits, substitutes or incorrectly pronounces specific sounds | Description:<br>Trouble with sound patterns or two consonants in the beginning of words. Trouble switching between sounds in front of mouth and back of mouth |
| Examples:<br>Wabbit vs rabbit<br>"thock" vs. "sock"<br>"sicken" vs. "chicken"<br>"wesson" vs. "lesson" | Examples:<br>(Consonants at the beginning)<br>Poon vs spoon<br>Boken vs Broken<br>(Front vs back of mouth)<br>Tup vs cup<br>Das vs gas |
| Audio Sample:<br>Provide an Audio Sample | Audio Sample:<br>Provide an Audio Sample |

6. If 4B Yes—Select which category more accurately describes your child's speaking challenge: (they can select multiple)
    a. Your child has trouble understanding others (Receptive Language Challenge)
    b. Your child has trouble expressing him or herself (Expressive Language Challenge)
7. If 4C Yes—Select which category more accurately describes your child's speaking challenge: (they can select multiple
    a. Stutterers "W-w-w-where are you going?"
    b. Clutters Sounds—"I-think-you . . . need-to-listen-to-me . . . a-little-more-carefully"
8. At what age did you first notice your child's Speech disorder
    a. Slider bar 1-18
9. Does your child have any diagnosed development challenges (check all that apply)
    a. None that I know ore
    b. Autism
    c. Asperger's
    d. Downs Syndrome
    e. Apraxia
    f. Cleft Palate
    g. Other (please describe) _____
10. What (if any) speech therapy is your child involved in (check all that apply)
    a. Nothing yet
    b. Speech therapy in school
    c. Speech therapy in private clinic or hospital
    d. Been working on it at home
11. On a scale of 1 to 10 and compared to your child's friends his/her age, how difficult is it to understand your child?
12. On a scale of 1 to 10, how frustrated/distressed is your child because of his/her speaking challenge?
13. On a scale of 1 to 10, how much is your child's speaking challenge affecting his/her performance in school?
14. (In the event the diagnostic is performed on the computer, short audio samples can be recorded the following represent sample audio samples to determine severity of R distortion)
    a. Repeat these 5 Sounds: R, Ra, Re, Ri, Ro Ru
    b. Repeat these Words: Row, Rug, Rack, Ray, Ring, Area, Corrupt, Caring, Arrow, Hurry, More, Year, Appear, Liar. Gear
    c. Repeat these 10 Sentences:
        i. We RAN to the post office to mail the package.
        ii. It takes a lot of time to PRACTICE the piano.
        iii. My parents took us for a ride in the CAR.
        iv. I need to stop READING with the lights off OR I will HURT my eyes.
        v. REBEL forces overtook the empire to take back the galaxy.
        vi. The ROAD home is closed!
        vii. I READ the NEWSPAPER at night
        viii. I have never met anyone from PEORIA, Ill.
        ix. Can I BORROW YOUR net to try and catch BUTTERFLIES?
        x. RAINBOWS are RARELY seen.
15. (To determine the difference between articulation and phonological disorders the following questions can be asked as an example)
    a. Q: Say "Rabbit" Answer: Child said 1) Rabbit, 2) Wabbit, 3) Yabbit
    b. Say "Spoon" Answer: Child said 1) Spoon, 2) Poon, 3) Thoon Sample Outputs
Probable Disorder Type (and prevalence)
Probable Severity
Suggested treatment type (types of exercises, frequency, single group, setting, etc)
Graph of Average Duration of treatment Diagnosis given inputs
Show Graph of Average Cost based on diagnosis given inputs Speaking and Language Learning Kits In order to train various classes of sounds for a wide variety of speakers in accordance with the methods, devices and systems described herein, a speaker or practitioner might need to cue various tongue positions during the production of speech sounds. To cue the various tongue oppositions, a speaker or practitioner may need to employ one or more of the nodes described herein (which may be complemented by one or more of the nodes disclosed by co-owned U.S. application Ser. No. 12/357,239) to provide proper tactile biofeedback. Therefore, one or more kits may be provided containing one more different nodes for providing the proper tactile biofeedback for the production of a wide range of speech sounds. A kit of this type may include a plurality of devices with device being configured to facilitate proper production of a particular speech sound and/or a particular set of speech sounds. Each kit may include a single handle having a plurality of different heads interchangeable therewith. The kit may alternatively have multiple handles (for example, of varying lengths and aesthetic appearances) in combination with one or more head to enable interchangeability with a large range of speakers.

One or more kits may include, along with one ore more handles and one or more heads, accompanying interactive software applications that may be downloaded on a desktop or uploaded from a remote site onto a mobile device. Instructions for use of the software applications may also be included in the kit along with resources for accessing any social networking platforms that provide the speaker with an interface for collaboration with other practitioners and speakers.

The kit may also include a mobile device having the software applications pre-loaded for ready use by the speaker and/or practitioner. Detection by a mobile or computing device of a waveform of a correct or incorrect pronunciation can be linked to the software application via coupling (which may be wireless) with any of the tactile biofeedback devices disclosed herein.

Other Applications a. Lactation

The concepts taught herein are not limited to the speech therapy and language learning methods described herein. For example, methods and devices incorporating the teachings herein may be contemplated for systems of measuring the suckling ability of infants. Measuring characteristics that are important in breastfeeding (or bottle feeding) can provide much needed information to doctors and mothers. Some characteristics that can be measured in a quantitative fashion using nodes and sensors include fixing (the quality of the seal created around nipple), sucking (the quantity of fluid transported into the infant's mouth) and rhythm (the consistency of the sucking action). Alternatively, all the information could be synthesized in a non-quantitative summary or indicator for the patient (e.g., "good", "medium", "bad").

A measurement of pressure differential may be made between the atmosphere and within the mouth with the lips as the barrier for the pressure gradient. Also a pressure differential can be created in an air gap in the upper roof of the mouth which is sealed off by the tongue (this action is comparable to the pronunciation of /t/ sound, for example). Exemplary embodiments may resemble a pacifier device, and incorporate a pressure sensor and display. Other exemplary embodiments may resemble a nipple, a finger or another shape that does not resemble an anatomical structure. Such a device enables the subject to create a seal around the lips and simulate the pressure differential that would occur breast or bottle feeding. Also, the rhythm of the sucking can be measured via these pressure sensors and translated into a quantitative or qualitative fashion.

Figure 34:
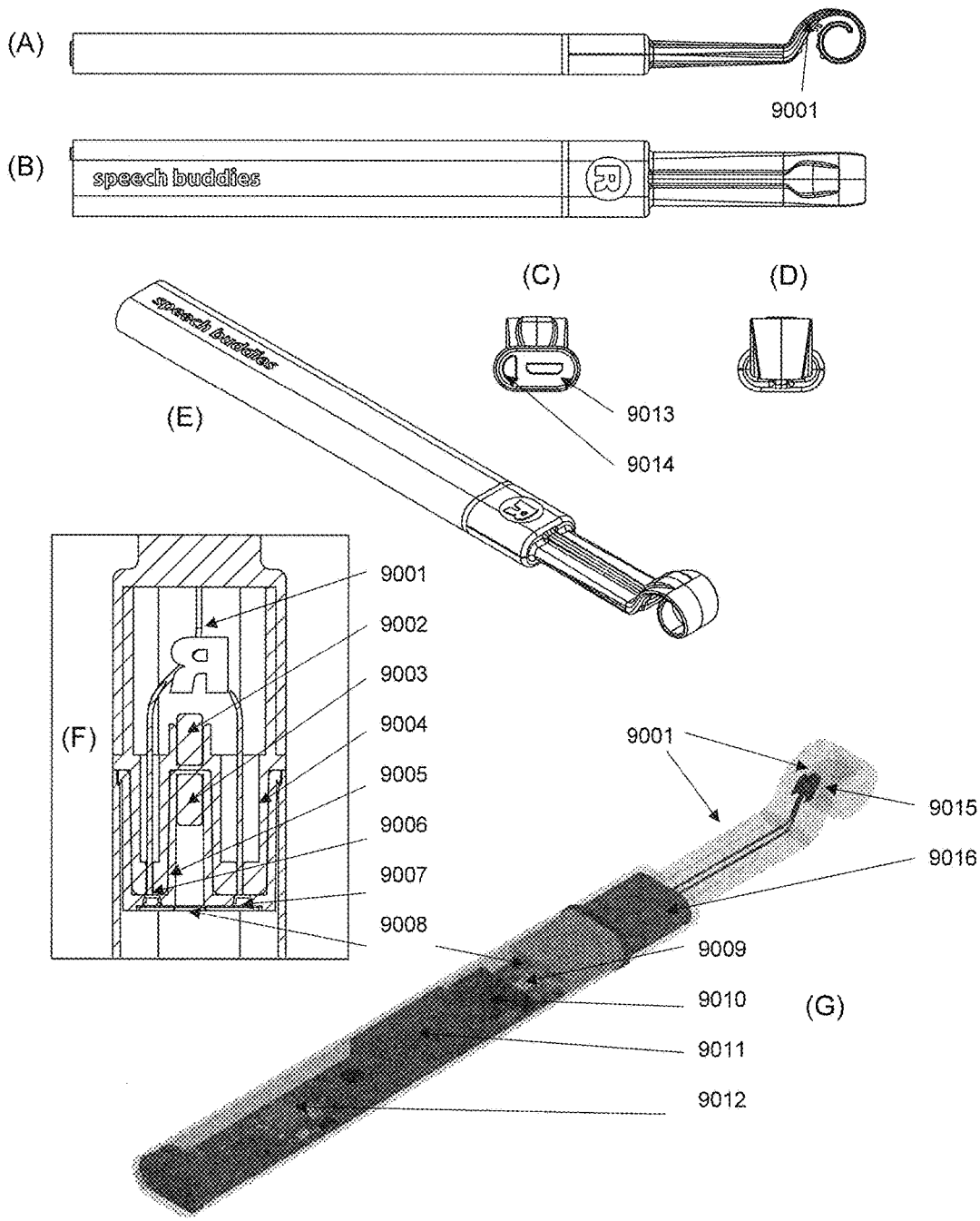
FIG. 34 shows a handle and tip assembly that uses two plastic fiber optic segments that are linked with an optical detector and optical emitter, wherein A is a side perspective view of the assembly, B is a top view thereof, C is a rear view thereof, D is a front view thereof, E is a perspective view thereof, F is a cross-section view thereof, and G is a view wherein outer components are shown in phantom to better illustrate the inner components.
Figure 35:
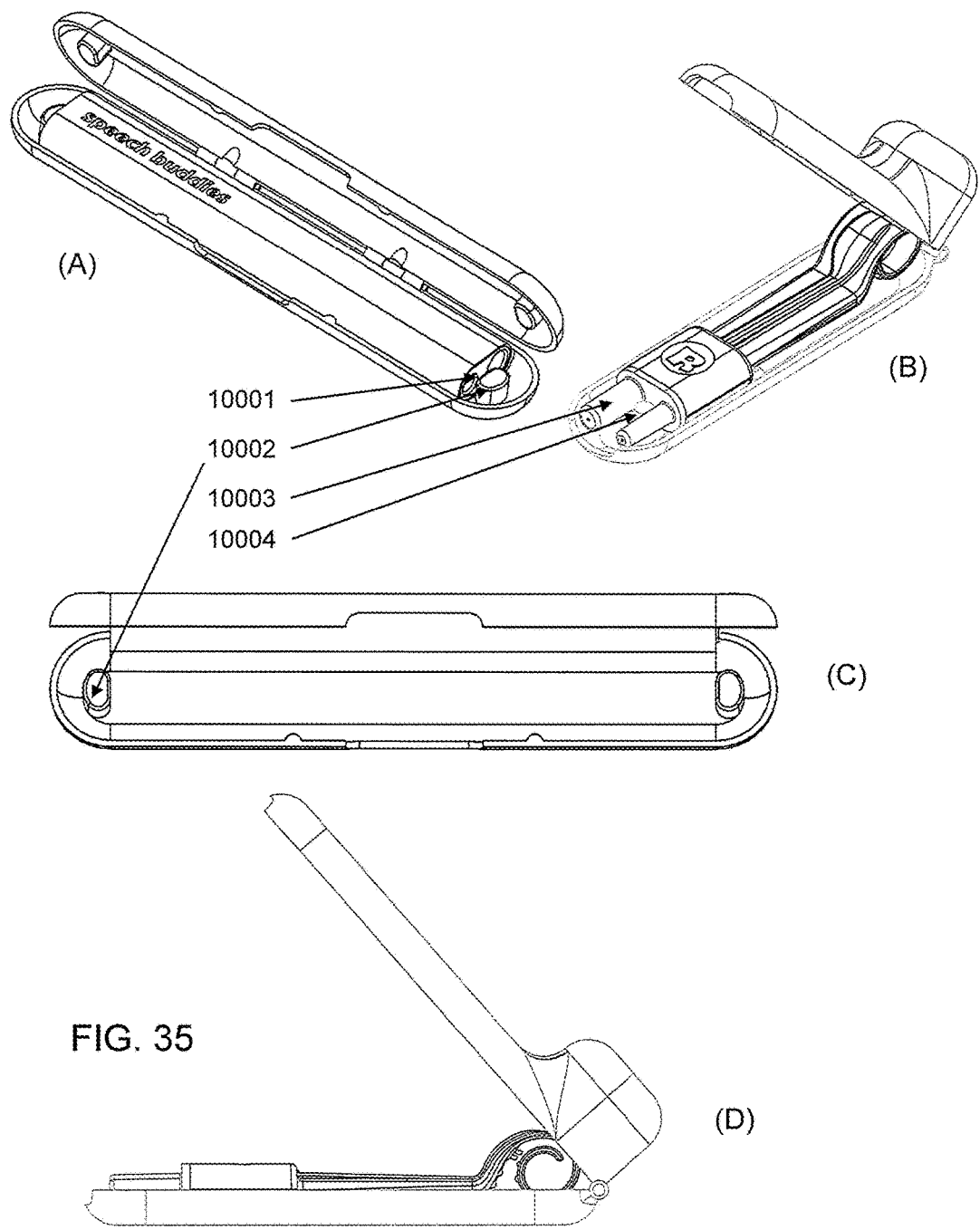
FIG. 35 shows cases for both the handle and tip components, wherein A is a perspective view of the first case in an open position, B is a perspective view of a second case in an open position, C is a side view of the first case in the open position and D is a side view of the second case in the open position.

The exemplary device shown in FIGS. 34 and 35 is an assembly that uses two plastic fiber optic segments 9001 that are linked with an optical detector 9006 and emitter 9007. This acts in placing the optical sensor on the tip of the device. FIGS. 34 A, B, C, D, E, F and G show the side, top, back, front, opaque isometric, sectional view of the mating tip and handle, and the transparent isometric assembly views, respectively. One magnet 9002 is embedded in the male 9004 connector for the tip of the device, while another magnet 9003 is embedded in the female 9005 end of the connector which is attached to the handle and electronics assembly. The handle portion contains the electronic components including a flexible printed circuit board 9008 which mates the detector 9006 and emitter 9007 directly to the plastic optical fibers 9001 of the tip. The electronics also contain a microphone 9009, a weight 9010, a battery 9011, a low energy Bluetooth processer 9012, a light pipe with colored light emitting diode and on/off button 9014, and a micro USB connector 9013. In this embodiment, both one piece of hard plastic with holes in it near the nodes 9015 and another piece of hard plastic, which constitutes the male end of the connector on the tip, hold the two plastic fiber optics 0.4 mm apart during over molding or injection molding of a soft plastic over the optics and hard plastics. This manufacturing process protects the plastic fiber optics from contaminants, light, and physical damage by embedding them in the softer plastic of the tip. The magnets are used to keep the tip and handle assembly together firmly during use of the device, but enable the handle and tip to be separated for cleaning, storage or installation of another tip onto the handle.

FIG. 35 shows cases for both the assembly and tip components. This figure clearly shoes the female connector in the handle 10001 and the male connector on the tip 10003. In this embodiment the connector has two elements of different diameter to ensure that the plastic fibers are always connected to the appropriate optical emitter and optical detector and not reversed. The case for the handle has a magnet 10002 on each side to ensure closure, and the case for the tip has a magnet 10004 to ensure closure as well. FIGS. 35A, B, C and D show the isometric view of the handle and open case, the isometric view of the tip and open case, the side view of the handle and case, and the side view of the tip and case, respectively.

FIG. 36A shows how data from both a microphone and an optical sensor are used to determine correct and incorrect pronunciations when the device is used by a patient. FIG. 36B shows a graphical user interface for a smart phone which prompts the user to pronounce a specific sound, consonant or word, the phone then receives data from a nearby Bluetooth processor which resides in the device handle, and subsequently displays on the graphical user interface if the word has been pronounced correctly or not. FIG. 36A shows the tip for the "R" phoneme being used by a patient. Data from the optical sensor 11001 shows if the tongue is unrolling the target coil, or touching the target or not. Data from the microphone 11002 can detect when a sound, syllable, or word is being pronounced. The onboard computer looks at both the microphone and optical sensor data together 11003 and if they correspond to an expected algorithm, it can accurately predict correct pronunciation 11004. A correct pronunciation of the English word "rabbit" is shown at time point 11005 as an optical detection, from unrolling of the coil, happens right at the initiation of enunciation. An incorrect pronunciation of the English word "rabbit" is shown at time point 11006 where no optical detection or coil unwinding occurs to match the acoustic detection which happened after word prompting. This same data synthesis shown in FIG. 36A can be used for sensors detecting tongue position and movement for other consonant phonemes including but not limited to /b/, /d/, /f/, /g/, /h/, /j/, /k/, /l/, /m/, /n/, /p/, /r/, /s/, /t/, /v/, /w/, /y/, /z/, /θ/ and /ð/, /Σ/ (sh), /Z/ (ζη), /τΣ/ (ch), /δZ/ (j), and /wh/, as well as vowel phonemes including but not limited to /a/, /e/, /i/, /o/, /u/, /ā/, /ē/, /ī/, /ō/, /ū/, /oo/, /o͞o/, /ow/, /oy/, /a(r)/, /ā(r)/, /i(r)/, /o(r)/, /u(r)/.

b. Oral Articulator Assessment

Methods and devices incorporating the teachings herein may also be contemplated for systems of measuring the movement and function of oral articulators, including the lips, tongue, cheeks, jaw, pharynx, larynx, soft palate and epiglottis. Such measurements may assist in the assessment and treatment of speech, voice, swallowing and other disorders. The exemplary methods and devices described below may be interchangeably provided in one or more kits to provide a fully diagnostic and modular tool for assessing multiple speakers.

i. Jaw Assessment

For example, the measurement of jaw strength, speed, and range of motion are important diagnostic characteristics for both assessment and treatment applications. Jaw range of motion can be described as 1) the rotational motion of jaw, such as in opening and closing of the jaw, 2) side to side motion of the jaw, and 3) the front to back motion of the jaw. For rotational motion, both the measurement of opening of the jaw as well as closing of the jaw is desirable. For the side to side and front to back motions, both directions of range of motion are desirable measures. The movement can be quantified in several types of measures: 1) force, 2) acceleration, 3) velocity, and 4) displacement (position). The measurement of these characteristics can be measured in a number of ways. They can be measured via a force sensor, pressure sensor, a displacement sensor, and a time sensor. Displacement as a function of time can help measure velocity, acceleration and force. Force can be measured through a pressure sensor which measures pressure as a function of the surface area under pressure. These attributes can also culminate in measuring a non-quantitative value of jaw coordination.

In an exemplary embodiment, force is measured with the jaw moving (or attempting to move) against a fixed or changing resistance. A sensor is compressed between the top and bottom teeth so that jaw measurements can be made. The sensor can include one or more of a force sensor and displacement sensor (with the latter measuring deformation of a material. In another exemplary embodiment, movement and force of the jaw opening can be measured. In addition, the force that can be generated by the jaw against a fixed sensor can also be measured. The sensor may be rigidly attached to another body such as a table or a doctor holding a device having sensors incorporated thereon.

ii. Tongue Assessment

The measurement of tongue strength, speed and range of motion are also important diagnostic characteristics for both assessment and treatment. The tongue is a single muscle which is controlled by many muscles and governed by a range of complex innervation patterns. It therefore exhibits a vast range of motion. The tongue can be broken down into different components, including the tip, the mid-section and the base, each of which has its own unique range of motion. Each of these components can move in the following fashion 1) up and down (superior/inferior) 2) side to side (lateral/medial) 3) forward and backwards (anterior/posterior), and 4) curling rotational (pitch, yaw, and roll). The tongue tip, mid-section and base all act as separate units and each segment has 6 degrees of freedom as per the three axes mentioned above. Assuming that there are 3 separate segments of the tongue each of which have 6 degrees of freedom, this results in 18 degrees of freedom for the system.

Measuring this movement and function of the tongue can be critical to the assessment and treatment of speech, voice, swallowing, and other disorders. A device that can easily measure these movements from a basic cardinal 4 degree of freedom (up/down, left/right, forward backward, axial) is critical, as is one that can measure the more discrete degrees of freedom from correct positioning is important as well. Measures would include: 1) Force, 2) acceleration, 3) velocity, and 4) displacement (position).

iii. Lip Assessment

Measurement of lip strength and precision is also an important measure for speech, voice, and other disorders. Common positions that the lips need to assume during speech include: inversion of the lips (for the /m/ sound), opening of the lips (for the /r/ sound), pursing of the lips (for the /sh/ sound), etc. Lip movement can be measured in several ways: 1) Force, 2) acceleration, 3) velocity, 4) displacement (position), 5) ability to hold a posture (such as S, R, CH, L, etc.), 6) ability to break a posture and 7) ability to assume a posture.

The measurement of these characteristics can be performed through a number of device embodiments. They can be measured via a force sensor, pressure sensor, a displacement sensor, and a time sensor. In an exemplary embodiment, the lips may squeeze upon a force or pressure sensor to measure the force of the lips. The sensor can be an electrical resistive sensor or a sensor that measures displacement. In another exemplary embodiment, the opening force of one or both of the upper and lower opening lips can be measured. In yet another exemplary embodiment, an array of sensors can be used on a device that measures lip coordination by measuring the exact location of contact of specific portions of the lips. This array of sensors can effectively measure qualitatively if the lips have engaged into the correct position for the desired sound, pose or exercise.

iv. Cheek Assessment

The measurement of movement and function of the cheek is another useful diagnostic and therapeutic approach in diagnosing and treating a variety of speech, voice, swallowing and related disorders. The buccinator muscles control what are more commonly known as cheek muscles. The orbicularis oris muscle is comprised of four muscles and it surrounds the lips. It is a sophisticated muscle that not only helps to control the lips but also the features surrounding the lips leading to the cheeks. The buccinator and orbicularis oris muscle function can be measured by displacement, force, velocity and acceleration of a given point on the skin.

v. Measurement of Teeth and Mouth Sizes

The measurement of teeth and mouth sizes can be beneficial for the recommendation of specific speech, medical or dental treatment or therapeutic regiments. A standard sizing of teeth and anatomical sizing can be achieved through a series of dental templates made out of ceramic, plastic, metal film, or wood. These sizes can be a series of sizes that vary both with and length and depth simultaneously. This template of can also be structured to vary width, length or depth independently. Alternative variables outside of length, width, and depth can be used within the scheme such as tooth width. Additionally depth can have measurements at multiple points within the oral cavity to determine the depth. Sensors disposed on the templates may provide a mapping of the speaker's oral cavity, including a mapping of areas where the teeth and or mouth experience stress (e.g., during speaking, breathing, chewing, etc.).

Results and Conclusions

Tactile biofeedback can be combined and integrated in alternate exemplary embodiments to link to other elements of language learning and thereby provide a holistic solution to traditional speech therapy and language learning methods.

The methods and devices taught herein are not limited for use with any one type of patient or student, and may be successfully employed beyond patients experiencing speech and/or language impairments. Such methods and devices are equally useful across a spectrum of physical and developmental disabilities as well as rehabilitation from a physical and/or psychological trauma. Such conditions may include, but are not limited to, autism, traumatic brain injuries (for example, those experienced with vehicle accidents, sports injuries, etc.), visual and/or hearing impairment (whether or not treated, such as with cochlear implants for hearing deficiencies), emotional instability (which may or may not be brought on by speech and language difficulties), developmental delay and other impairments to physical, psychological and/or emotional wellbeing. The disclosed methods and devices are also amenable for use with students having limited strength and requiring controlled breathing techniques, for example, those patients and students having cardiopulmonary problems (e.g., chronic asthma), epilepsy, etc.

Not all sound substitutions and omissions are speech errors and may instead be related to a feature of a dialect or accent. For those learners not suffering from any of the aforementioned maladies, such learners can benefit from use of the disclosed methods and devices to improve speech delivery and inflection, for example, for acting, public speaking or for learning a non-native language.

The methods and devices taught herein enable easy and effective collaboration among professionals, speakers, family members and caretakers as part of a multidisciplinary team. For example, using the devices and methods herein, real-time (or near real-time) tracking of a speaker's progress may be realized by speech pathologists, audiologists, nurses, occupational therapists and surgeons all consulting on a single speaker's case. Family members may also easily track a loved one's progress and/or assist in ongoing treatment or education of a family member (these results may be shared among family members who may not live in proximity to one another). Adults using this technology can use it in conjunction with speech therapists, linguistics and language teachers (including but not limited to English teachers) on their own, in school or in a medical facility. A skilled SLP is not required to successfully execute the methods taught herein.

The methods and devices taught herein are amenable for use with existing written materials and in conjunction with software, or additional written materials and/or software may be prepared to complement these methods and devices without deviating from the successful practice thereof. Friends and colleagues may assist one another in a digital environment, for example, by using these methods and devices on a social platform and enabling collaborative correction and positive reinforcement. For example, if one colleague has superior elocution, that colleague's speech sounds can be recorded and used as a baseline for proper speech against which other colleagues may be evaluated for training. Such an application might be desirable, for example, in multinational businesses requiring cross-border communication.

The dimensions and values disclosed herein are not to be understood as being strictly limited to the exact numerical values recited. Instead, unless otherwise specified, each such dimension is intended to mean both the recited value and a functionally equivalent range surrounding that value as well as equivalent units of that value. For example, a dimension disclosed as "40 mm" is intended to mean "about 40 mm" as well as "1.58 inches". The disclosure of such dimensions and values, however, shall not preclude use of any of disclosed devices having dimensions and values outside of the prescribed ranges.

Every document cited herein, including any cross-referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While the invention has been described in a preferred form, it will be understood that changes, additions, and modifications may be made to the respective articles forming the invention. Accordingly, no limitation should be imposed on the scope of this invention, except as set forth in the accompanying claims.

What is claimed is:

1. A method of teaching a user to pronounce a particular sound, which comprises:

providing at least two sound training devices, wherein each sound training device comprises a node support and one or more nodes for indicating proper positioning of the user's tongue for accurate pronunciation of the particular sound, with the node support configured and dimensioned (a) to provide tactile feedback to the user at its respective node location(s) on the node support with the feedback signaling proper positioning of the tongue for accurate pronunciation of the particular sound, and (b) to limit intrusiveness in the user's mouth while providing sufficient strength to support the one or more nodes;

providing at least one of the one or more nodes with at least one sensor mounted thereon, with the at least one sensor being no larger than the at least one nodes and being positioned and dimensioned for sensing lingual contact of the user's tongue with or near the at least one nodes, providing a signal based such contact, and transmitting the signal to a computer; and providing each sound training device with registration features for positioning each sound training device in an appropriate location in the user's oral cavity such that the user's tongue is able to freely navigate to contact the one or more nodes and be positioned for making the particular sound with the location being dependent on the particular sound to be made, wherein, when the tongue is so positioned, the sound training device provides tactile feedback to the user to assist in proper and accurate pronunciation of the particular sound, and wherein the computer includes software that monitors contact of the tongue with the at least one sensor that is mounted on the one or more nodes to provide interactive feedback including one or more of:
real time on-screen visualization of lingual contacts with the one or more nodes;
positive reinforcement based on progress, data collection or statistical analysis;
playback of recorded verbal reproductions;
an indication of the status of patient speech productions; and
pre-recorded phoneme productions greater accuracy via imitation;
wherein the at least two sound training devices are selected from the group consisting of:
a first device comprising a node configured to be positioned in a medial location inferior to the user's palate to provide tactile feedback for the proper tongue position corresponding to the /r/ sound;
a second device comprising a node configured to be positioned in a location on the user's alveolar ridge to provide tactile feedback for the proper tongue position corresponding to the /l/, /t/, or /d/ sound;
a third device comprising a pair of nodes configured to be positioned in lateral posterior locations on either side of the user's palate to provide tactile feedback for the proper tongue position corresponding to the /k/ or /g/ sound;
a fourth device comprising a pair of nodes configured to be positioned in lateral anterior locations on either side of the user's palate to provide tactile feedback for the proper tongue position corresponding to the /i/ sound;
a fifth device comprising a node configured to be positioned in an anterior location inferior to the user's palate to provide tactile feedback for the proper tongue position corresponding to the /s/, /z/, /Σ/ (sh), or /Z/ (ζη) sounds; and
a sixth device comprising a node configured to be positioned in an anterior location on the user's palate to provide tactile feedback for the proper tongue position corresponding to the /τΣ/ (ch) or /δZ/ (j) sound,
wherein the sound training devices are provided in a kit that includes one or more handles for holding each sound training device, such that the insertion of a sound training device in the user's oral cavity enables the registration features to automatically place the at least one sensor in correspondence with proper lingual positions for production of the at least one target sound.

2. The method of claim 1, which further comprises:
operatively associating the at least one sensor of the sound training device to detect whether the user's tongue correctly contacts with an intended target and to provide biofeedback in real time to inform the user's of pronunciation accuracy of the at least one target sound;
connecting the at least one sound training device to a network in communication with the computer running at least one pronunciation evaluation application thereon; and
providing the real time biofeedback to the user of tongue target contact and positioning so that the speaker can learn correct pronunciation of the at least one target sound.

3. The method of claim 2, further including providing a platform comprising:
a server in communication with the network-connected sound training device, the server configured to perform actions comprising at least one of:
accessing at least one of: an intraoral biofeedback system for training and enhancing a user's pronunciation, and a social networking system;
building and accessing a database of profiles of sensor outputs that can be generated for intended target sounds; and
uploading at least one of: user profile data and data corresponding to one or more general diagnostic tests for storage on the database.

4. The method of claim 3, wherein the platform further comprises a network interface for performing at least one of:
communicating over a network;
facilitating communication between the at least one sound training device and the computer;
generating one or more representations of the user's pronunciation accuracy; and
an engine configured to perform at least one of:
comparing a sample sound to the database of profiles; and
determining the pronunciation accuracy for providing feedback to the user.

5. The method of claim 4, wherein the engine is further configured to generate a notification that notifies the user with updated user profile data and updated data corresponding to the general diagnostic tests.

6. The method of claim 3, wherein the intraoral biofeedback computer software is provided as a software tool configured for mobile applications.

7. The method of claim 1, wherein each sound training device in the kit has a separate handle associated with it for holding the sound training device during use.

8. The method of claim 1, wherein the at least one sensor includes: one or more of an optical sensor, a force sensing resistor, a bridge sensor, a capacitive sensor, a strain gauge sensor, a sensor array and any equivalent and combination thereof.

9. The method of claim 1, wherein the method further comprises comparing a sample sound's tactile profile to a database of profiles to determine pronunciation accuracy for providing feedback to the user.

10. The method of claim 1, wherein the one or more handles in the kit is a common handle that can be used for separately and sequentially holding each sound training device in the kit.

11. The method of claim 10, wherein both the common handle and the head of the at least one sound training device include a magnet therein for detachable engagement with one another.

12. The method of claim 1, wherein the kit includes multiple devices that have separate handles or that are selectively interchangeable with a common handle to detect pronunciation accuracy of the different target sounds when the user's tongue contacts one or more targets in the user's oral cavity for proper positioning of a user's tongue to train at least one target sound through tactile feedback to the user, with the locating being dependent on the target sound being trained; and wherein the target sound is selected from /b/, /h/, /m/, /n/, /p/, /v/, /w/, /θ/ /ð/, /wh/, /a/, /e/, /i/, /o/, /u/, /ā/, /ē/, /ī/, /ō/, /ū/, /oo/, /o͞o/, /ow/, /oy/, /a(r)/, /ā(r)/, /i(r)/, /o(r)/, or /u(r)/.

13. The method of claim 12, wherein the kit further comprises one or more interactive software applications loadable onto the computer.

14. The method of claim 13, wherein the kit further comprises instructions for use of the software applications that include instructions for accessing a platform that provide the user with an interface for collaboration with others over a social network.

15. The method of claim 13, wherein the kit further comprises a mobile device having the software applications pre-loaded thereon.

16. The method of claim 1, which further comprises prompting the user to make the particular speech sound by contacting the at least one of the one or more nodes with his or her tongue after positioning the sound training device and the at least one of the one or more nodes is in a location in the user's oral cavity corresponding to the appropriate lingual position for the particular speech sound.

17. The method of claim 1, wherein the at least one of the one or more nodes is configured in a spring or coil shape, or supported on a slide that allows the at least one of one or more nodes to move in response to pressure applied by the user's tongue.

18. The method of claim 1, wherein the user is hearing impaired, suffers from acquired apraxia of speech, developmental apraxia of speech, or dysarthria.

19. The method of claim 1, wherein the user is learning to speak sounds that are foreign to his or her native language.

20. The method of claim 1, wherein the sound training device includes fiber optic segments that are operably linked with an optical detector and emitter to assist in placement of the sensor in the user's mouth.

* * * * *